United States Patent
Ishino et al.

(10) Patent No.: US 9,447,388 B2
(45) Date of Patent: Sep. 20, 2016

(54) DNA POLYMERASES

(75) Inventors: Yoshizumi Ishino, Fukuoka (JP);
Takeshi Yamagami, Fukuoka (JP);
Hiroaki Matsukawa, Fukuoka (JP);
Takashi Uemori, Otsu (JP); Takehiro Sagara, Otsu (JP)

(73) Assignees: KYUSHU UNIVERSITY, NATIONAL UNIVERSITY CORPORATION, Fukuoka-shi (JP); TAKARA BIO INC., Kusatsu-shi (JP)

( * ) Notice: Subject to any disclaimer, the term of this patent is extended or adjusted under 35 U.S.C. 154(b) by 347 days.

(21) Appl. No.: 14/232,174

(22) PCT Filed: Jul. 12, 2012

(86) PCT No.: PCT/JP2012/067791
§ 371 (c)(1),
(2), (4) Date: May 2, 2014

(87) PCT Pub. No.: WO2013/008877
PCT Pub. Date: Jan. 17, 2013

(65) Prior Publication Data
US 2014/0322793 A1    Oct. 30, 2014

(30) Foreign Application Priority Data

Jul. 12, 2011  (JP) ................................ 2011-153410

(51) Int. Cl.
*C12N 9/12* (2006.01)
*C12N 1/00* (2006.01)
(Continued)

(52) U.S. Cl.
CPC ............... *C12N 9/1252* (2013.01); *C12N 1/00* (2013.01); *C12N 1/20* (2013.01); *C12N 15/63* (2013.01); *C12P 19/34* (2013.01); *C12Y 207/07007* (2013.01); *Y02P 20/52* (2015.11)

(58) Field of Classification Search
None
See application file for complete search history.

(56) References Cited

U.S. PATENT DOCUMENTS 8,735,120 B2 * 5/2014 Reichert ............. C12N 9/1252
435/183
8,735,121 B2 * 5/2014 Reichert ............. C12N 9/1252
435/183

(Continued)

FOREIGN PATENT DOCUMENTS

JP  2006-101791 A  4/2006
JP  2006-204267 A  8/2006

(Continued)

*Primary Examiner* — Robert Mondesi
*Assistant Examiner* — Richard Ekstrom
(74) *Attorney, Agent, or Firm* — Birch, Stewart, Kolasch & Birch, LLP

(57) ABSTRACT

Provided are various novel DNA polymerases. Provided is a DNA polymerase comprising an amino acid sequence modified from the amino acid sequence of SEQ ID NO: 8 by inserting nine amino acids "-$A_{737}$-$A_{738}$-$A_{739}$-$A_{740}$-$A_{741}$-$A_{742}$-$A_{743}$-$A_{744}$-$A_{745}$-" between the amino acid residue at position 736 and the amino acid residue at position 737, wherein:

$A_{737}$ is an amino acid residue having a non-polar aliphatic side chain;
$A_{738}$ is an amino acid residue having a non-polar aliphatic side chain;
$A_{739}$ is an amino acid residue having a positively charged side chain;
$A_{740}$ is an amino acid residue having a positively charged side chain;
$A_{741}$ is an amino acid residue having a non-polar aliphatic side chain;
$A_{742}$ is an amino acid residue having a non-polar aliphatic side chain;
$A_{743}$ is any given amino acid residue;
$A_{744}$ is an amino acid residue having a positively charged side chain; and
$A_{745}$ is an amino acid residue having a non-polar aliphatic side chain).

14 Claims, 9 Drawing Sheets

(51) Int. Cl.
*C12N 1/20* (2006.01)
*C12N 15/63* (2006.01)
*C12P 19/34* (2006.01)

(56) References Cited

U.S. PATENT DOCUMENTS

2011/0281305 A1\* 11/2011 Bourn ................. C12N 9/1241
                                                                                435/91.2

2014/0030765 A1\* 1/2014 Schafer ................. C12N 9/1252
                                                                                435/91.2
2014/0363875 A1\* 12/2014 Ishino ................... C12N 9/1252
                                                                                435/194

FOREIGN PATENT DOCUMENTS

JP            4193997 B1    10/2008
WO   WO 2009155464 A2 \* 12/2009   ........... C12N 9/1252

\* cited by examiner

FIG. 5

Taq WT nucleotide sequence (2499bp)     SEQ ID NO: 7

ATGAGGGGGATGCTGCCCCTCTTTGAGCCCAAGGGCCGGGTCCTCCTGGTGGACGGCCACCACCTGGCCTACCGCACCTT
CCACGCCCTGAAGGGCCTCACCACCAGCCGGGGGGAGCCGGTGCAGGCGGTCTACGGCTTCGCCAAGAGCCTCCTCAAGG
CCCTCAAGGAGGACGGGGACGCGGTGATCGTGGTCTTTGACGCCAAGGCCCCCTCCTTCCGCCACGAGGCCTACGGGGGG
TACAAGGCGGGCCGGGCCCCCACGCCGGAGGACTTTCCCCGGCAACTCGCCCTCATCAAGGAGCTGGTGGACCTCCTGGG
GCTGGCGCGCCTCGAGGTCCCGGGCTACGAGGCGGACGACGTCCTGGCCAGCCTGGCCAAGAAGGCGGAAAAGGAGGGCT
ACGAGGTCCGCATCCTCACCGCCGACAAAGACCTTTACCAGCTCCTTTCCGACCGCATCCACGTCCTCCACCCCGAGGGG
TACCTCATCACCCCGGCCTGGCTTTGGGAAAAGTACGGCCTGAGGCCCGACCAGTGGGCCGACTACCGGGCCCTGACCGG
GGACGAGTCCGACAACCTTCCCGGGGTCAAGGGCATCGGGGAGAAGACGGCGAGGAAGCTTCTGGAGGAGTGGGGGAGCC
TGGAAGCCCTCCTCAAGAACCTGGACCGGCTGAAGCCCGCCATCCGGGAGAAGATCCTGGCCCACATGGACGATCTGAAG
CTCTCCTGGGACCTGGCCAAGGTGCGCACCGACCTGCCCCTGGAGGTGGACTTCGCCAAAAGGCGGGAGCCCGACCGGGA
GAGGCTTAGGGCCTTTCTGGAGAGGCTTGAGTTTGGCAGCCTCCTCCACGAGTTCGGCCTTCTGGAAAGCCCCAAGGCCC
TGGAGGAGGCCCCCTGGCCCCCGCCGGAAGGGGCCTTCGTGGGCTTTGTGCTTTCCCGCAAGGAGCCCATGTGGGCCGAT
CTTCTGGCCCTGGCCGCCGCCAGGGGGGGCCGGGTCCACCGGGCCCCCGAGCCTTATAAAGCCCTCAGGGACCTGAAGGA
GGCGCGGGGGCTTCTCGCCAAAGACCTGAGCGTTCTGGCCCTGAGGGAAGGCCTTGGCCTCCCGCCCGGCGACGACCCCA
TGCTCCTCGCCTACCTCCTGGACCCTTCCAACACCACCCCCGAGGGGGTGGCCCGGCGCTACGGCGGGGAGTGGACGGAG
GAGGCGGGGGAGCGGGCCGCCCTTTCCGAGAGGCTCTTCGCCAACCTGTGGGGGAGGCTTGAGGGGGAGGAGAGGCTCCT
TTGGCTTTACCGGGAGGTGGAGAGGCCCCTTTCCGCTGTCCTGGCCCACATGGAGGCCACGGGGGTGCGCCTGGACGTGG
CCTATCTCAGGGCCTTGTCCCTGGAGGTGGCCGAGGAGATCGCCCGCCTCGAGGCCGAGGTCTTCCGCCTGGCCGGCCAC
CCCTTCAACCTCAACTCCCGGGACCAGCTGGAAAGGGTCCTCTTTGACGAGCTAGGGCTTCCCGCCATCGGCAAGACGGA
GAAGACCGGCAAGCGCTCCACCAGCGCCGCCGTCCTGGAGGCCCTCCGCGAGGCCCACCCCATCGTGGAGAAGATCCTGC
AGTACCGGGAGCTCACCAAGCTGAAGAGCACCTACATTGACCCCTTGCCGGACCTCATCCACCCCAGGACGGGCCGCCTC
CACACCCGCTTCAACCAGACGGCCACGGCCACGGGCAGGCTAAGTAGCTCCGATCCCAACCTCCAGAACATCCCCGTCCG
CACCCCGCTTGGGCAGAGGATCCGCCGGGCCTTCATCGCCGAGGAGGGGTGGCTATTGGTGGCCCTGGACTATAGCCAGA
TAGAGCTCAGGGTGCTGGCCCACCTCTCCGGCGACGAGAACCTGATCCGGGTCTTCCAGGAGGGGCGGGACATCCACACG
GAGACCGCCAGCTGGATGTTCGGCGTCCCCCGGGAGGCCGTGGACCCCCTGATGCGCCGGGCGGCCAAGACCATCAACTT
CGGGGTCCTCTACGGCATGTCGGCCCACCGCCTCTCCCAGGAGCTAGCCATCCCTTACGAGGAGGCCCAGGCCTTCATTG
AGCGCTACTTTCAGAGCTTCCCCAAGGTGCGGGCCTGGATTGAGAAGACCCTGGAGGAGGGCAGGAGGCGGGGGTACGTG
GAGACCCTCTTCGGCCGCCGCCGCTACGTGCCAGACCTAGAGGCCCGGGTGAAGAGCGTGCGGGAGGCGGCCGAGCGCAT
GGCCTTCAACATGCCCGTCCAGGGCACCGCCGCCGACCTCATGAAGCTGGCTATGGTGAAGCTCTTCCCCAGGCTGGAGG
AAATGGGGGCCAGGATGCTCCTTCAGGTCCACGACGAGCTGGTCCTCGAGGCCCCAAAAGAGAGGGCGGAGGCCGTGGCC
CGGCTGGCCAAGGAGGTCATGGAGGGGGTGTATCCCCTGGCCGTGCCCCTGGAGGTGGAGGTGGGGATAGGGGAGGACTG
GCTCTCCGCCAAGGAGTGA

Taq WT amino acid sequence (832 amino acids)     SEQ ID NO: 8

MRGMLPLFEPKGRVLLVDGHHLAYRTFHALKGLTTSRGEPVQAVYGFAKSLLKALKEDGDAVIVVFDAKAPSFRHEAYGG
YKAGRAPTPEDFPRQLALIKELVDLLGLARLEVPGYEADDVLASLAKKAEKEGYEVRILTADKDLYQLLSDRIHVLHPEG
YLITPAWLWEKYGLRPDQWADYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWPPPEGAFVGFVLSRKEPMWAD
LLALAAARGGRVHRAPEPYKALRDLKEARGLLAKDLSVLALREGLGLPPGDDPMLLAYLLDPSNTTPEGVARRYGGEWTE
EAGERAALSERLFANLWGRLEGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTKLKSTYIDPLPDLIHPRTGRL
HTRFNQTATATGRLSSSDPNLQNIPVRTPLGQRIRRAFIAEEGWLLVALDYSQIELRVLAHLSGDENLIRVFQEGRDIHT
ETASWMFGVPREAVDPLMRRAAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARMLLQVHDELVLEAPKERAEAVA
RLAKEVMEGVYPLAVPLEVEVGIGEDWLSAKE

FIG. 6

Taq Exo⁻ nucleotide sequence  SEQ ID NO: 9

ATGAGGGGGATGCTGCCCCTCTTTGAGCCCAAGGGCCGGGTCCTCCTGGTGGACGGCCACCACCTGGCCTACCGCACCTT
CCACGCCCTGAAGGGCCTCACCACCAGCCGGGGGGAGCCGGTGCAGGCGGTCTACGGCTTCGCCAAGAGCCTCCTCAAGG
CCCTCAAGGAGGACGGGGACGCGGTGATCGTGGTCTTTGACGCCAAGGCCCCCTCCTTCCGCCACGAGGCCTACGGGGGG
TACAAGGCGGGCCGGGCCCCCACGCCGGAGGACTTTCCCCGGCAACTCGCCCTCATCAAGGAGCTGGTGGACCTCCTGGG
GCTGGCGCGCCTCGAGGTCCCGGGCTACGCGGCGGCCGACGTCCTGGCCAGCCTGGCCAAGAAGGCGGAAAAGGAGGGCT
ACGAGGTCCGCATCCTCACCGCCGCCAAAGCCCTTTACCAGCTCCTTTCCGACCGCATCCACGTCCTCCACCCCGAGGGG
TACCTCATCACCCCGGCCTGGCTTTGGGAAAAGTACGGCCTGAGGCCCGACCAGTGGGCCGACTACCGGGCCCTGACCGG
GGACGAGTCCGACAACCTTCCCGGGGTCAAGGGCATCGGGGAGAAGACGGCGAGGAAGCTTCTGGAGGAGTGGGGGAGCC
TGGAAGCCCTCCTCAAGAACCTGGACCGGCTGAAGCCCGCCATCCGGGAGAAGATCCTGGCCCACATGGACGATCTGAAG
CTCTCCTGGGACCTGGCCAAGGTGCGCACCGACCTGCCCCTGGAGGTGGACTTCGCCAAAAGGCGGGAGCCCGACCGGGA
GAGGCTTAGGGCCTTTCTGGAGAGGCTTGAGTTTGGCAGCCTCCTCCACGAGTTCGGCCTTCTGGAAAGCCCCAAGGCCC
TGGAGGAGGCCCCCTGGCCCCCGCCGGAAGGGGCCTTCGTGGGCTTTGTGCTTTCCCGCAAGGAGCCCATGTGGGCCGAT
CTTCTGGCCCTGGCCGCCGCCAGGGGGGGCCGGGTCCACCGGGCCCCCGAGCCTTATAAAGCCCTCAGGGACCTGAAGGA
GGCGCGGGGGCTTCTCGCCAAAGACCTGAGCGTTCTGGCCCTGAGGGAAGGCCTTGGCCTCCCGCCCGGCGACGACCCCA
TGCTCCTCGCCTACCTCCTGGACCCTTCCAACACCACCCCCGAGGGGGTGGCCCGGCGCTACGGCGGGGAGTGGACGGAG
GAGGCGGGGAGCGGGCCGCCCTTTCCGAGAGGCTCTTCGCCAACCTGTGGGGGAGGCTTGAGGGGAGGAGAGGCTCCT
TTGGCTTTACCGGGAGGTGGAGAGGCCCCTTTCCGCTGTCCTGGCCCACATGGAGGCCACGGGGGTGCGCCTGGACGTGG
CCTATCTCAGGGCCTTGTCCCTGGAGGTGGCCGAGGAGATCGCCCGCCTCGAGGCCGAGGTCTTCCGCCTGGCCGGCCAC
CCCTTCAACCTCAACTCCCGGGACCAGCTGGAAAGGGTCCTCTTTGACGAGCTAGGGCTTCCCGCCATCGGCAAGACGGA
GAAGACCGGCAAGCGCTCCACCAGCGCCGCCGTCCTGGAGGCCCTCCGCGAGGCCCACCCCATCGTGGAGAAGATCCTGC
AGTACCGGGAGCTCACCAAGCTGAAGAGCACCTACATTGACCCCTTGCCGGACCTCATCCACCCCAGGACGGGCCGCCTC
CACACCCGCTTCAACCAGACGGCCACGGCCACGGGCAGGCTAAGTAGCTCCGATCCCAACCTCCAGAACATCCCCGTCCG
CACCCCGCTTGGGCAGAGGATCCGCCGGGCCTTCATCGCCGAGGAGGGGTGGCTATTGGTGGCCCTGGACTATAGCCAGA
TAGAGCTCAGGGTGCTGGCCCACCTCTCCGGCGACGAGAACCTGATCCGGGTCTTCCAGGAGGGGCGGGACATCCACACG
GAGACCGCCAGCTGGATGTTCGGCGTCCCCCGGGAGGCCGTGGACCCCCTGATGCGCCGGGCGGCCAAGACCATCAACTT
CGGGGTCCTCTACGGCATGTCGGCCCACCGCCTCTCCCAGGAGCTAGCCATCCCCTTACGAGGAGGCCCAGGCCTTCATTG
AGCGCTACTTTCAGAGCTTCCCCAAGGTGCGGGCCTGGATTGAGAAGACCCTGGAGGAGGGCAGGAGGCGGGGGTACGTG
GAGACCCTCTTCGGCCGCCGCCGCTACGTGCCAGACCTAGAGGCCCGGGTGAAGAGCGTGCGGGAGGCGGCCGAGCGCAT
GGCCTTCAACATGCCCGTCCAGGGCACCGCCGCCGACCTCATGAAGCTGGCTATGGTGAAGCTCTTCCCCAGGCTGGAGG
AAATGGGGGCCAGGATGCTCCTTCAGGTCCACGACGAGCTGGTCCTCGAGGCCCCAAAAGAGAGGGCGGAGGCCGTGGCC
CGGCTGGCCAAGGAGGTCATGGAGGGGGTGTATCCCCTGGCCGTGCCCCTGGAGGTGGAGGTGGGGATAGGGGAGGACTG
GCTCTCCGCCAAGGAGTGA

Taq Exo⁻ amino acid sequence  SEQ ID NO: 10

MRGMLPLFEPKGRVLLVDGHHLAYRTFHALKGLTTSRGEPVQAVYGFAKSLLKALKEDGDAVIVVFDAKAPSFRHEAYGG
YKAGRAPTPEDFPRQLALIKELVDLLGLARLEVPGYAAADVLASLAKKAEKEGYEVRILTAAKALYQLLSDRIHVLHPEG
YLITPAWLWEKYGLRPDQWADYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWPPPEGAFVGFVLSRKEPMWAD
LLALAAARGGRVHRAPEPYKALRDLKEARGLLAKDLSVLALREGLGLPPGDDPMLLAYLLDPSNTTPEGVARRYGGEWTE
EAGERAALSERLFANLWGRLEGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTKLKSTYIDPLPDLIHPRTGRL
HTRFNQTATATGRLSSSDPNLQNIPVRTPLGQRIRRAFIAEEGWLLVALDYSQIELRVLAHLSGDENLIRVFQEGRDIHT
ETASWMFGVPREAVDPLMRRAAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARMLLQVHDELVLEAPKERAEAVA
RLAKEVMEGVYPLAVPLEVEVGIGEDWLSAKE

FIG. 7

Taq 9aa nucleotide sequence            SEQ ID NO: 11

ATGAGGGGGATGCTGCCCCTCTTTGAGCCCAAGGGCCGGGTCCTCCTGGTGGACGGCCACCACCTGGCCTACCGCACCTT
CCACGCCCTGAAGGGCCTCACCACCAGCCGGGGGAGCCGGTGCAGGCGGTCTACGGCTTCGCCAAGAGCCTCCTCAAGG
CCCTCAAGGAGGACGGGGACGCGGTGATCGTGGTCTTTGACGCCAAGGCCCCCTCCTTCCGCCACGAGGCCTACGGGGGG
TACAAGGCGGGCCGGGCCCCCACGCCGGAGGACTTTCCCCGGCAACTCGCCCTCATCAAGGAGCTGGTGGACCTCCTGGG
GCTGGCGCGCCTCGAGGTCCCGGGCTACGAGGCGGACGACGTCCTGGCCAGCCTGGCCAAGAAGGCGGAAAAGGAGGGCT
ACGAGGTCCGCATCCTCACCGCCGACAAAGACCTTTACCAGCTCCTTTCCGACCGCATCCACGTCCTCCACCCCGAGGGG
TACCTCATCACCCCGGCCTGGCTTTGGAAAAGTACGGCCTGAGGCCCGACCAGTGGGCCGACTACCGGGCCCTGACCGG
GGACGAGTCCGACAACCTTCCCGGGGTCAAGGGCATCGGGGAGAAGACGGCCGAGGAAGCTTCTGGAGGAGTGGGGGAGCC
TGGAAGCCCTCCTCAAGAACCTGGACCGGCTGAAGCCCGCCATCCGGGAGAAGATCCTGGCCCACATGGACGATCTGAAG
CTCTCCTGGGACCTGGCCAAGGTGCGCACCGACCTGCCCCTGGAGGTGGACTTCGCCAAAAGGCGGGAGCCCGACCGGGA
GAGGCTTAGGGCCTTTCTGGAGAGGCTTGAGTTTGGCAGCCTCCTCCACGAGTTCGGCCTTCTGGAAAGCCCCAAGGCCC
TGGAGGAGGCCCCCTGGCCCCGCCGGAAGGGGCCTTCGTGGGCTTTGTGCTTTCCCGCAAGGAGCCCATGTGGGCCGAT
CTTCTGGCCCTGGCCGCCGCCAGGGGGGGCCGGGTCCACCGGGCCCCCGAGCCTTATAAAGCCCTCAGGGACCTGAAGGA
GGCGCGGGGCTTCTCGCCAAAGACCTGAGCGTTCTGGCCCTGAGGGAAGGCCTTGGCCTCCCGCCGGCGACGACCCCA
TGCTCCTCGCCTACCTCCTGGACCCTTCCAACACCACCCCGAGGGGGTGGCCCGGCGCTACGGCGGGGAGTGGACGGAG
GAGGCGGGGAGCGGGCCGCCCTTTCCGAGAGGCTCTTCGCCAACCTGTGGGGGAGGCTTGAGGGGGAGGAGAGGCTCCT
TTGGCTTTACCGGGAGGTGGAGAGGCCCCTTTCCGCTGTCCTGGCCCACATGGAGGCCACGGGGGTGCGCCTGGACGTGG
CCTATCTCAGGGCCTTGTCCCTGGAGGTGGCCGAGGAGATCGCCCGCCTCGAGGCCGAGGTCTTCCGCCTGGCCGGCCAC
CCCTTCAACCTCAACTCCCGGGACCAGCTGGAAAGGGTCCTCTTTGACGAGCTAGGGCTTCCCGCCATCGGCAAGACGGA
GAAGACCGGCAAGCGCTCCACCAGCGCCGCCGTCCTGGAGGCCCTCCGCGAGGCCCACCCCATCGTGGAGAAGATCCTGC
AGTACCGGGAGCTCACCAAGCTGAAGAGCACCTACATTGACCCCTTGCCGGACCTCATCCACCCCAGGACGGGCCGCCTC
CACACCCGCTTCAACCAGACGGCCACGGCCACGGGCAGGCTAAGTAGCTCCGATCCCAACCTCCAGAACATCCCCGTCCG
CACCCCGCTTGGGCAGAGGATCCGCCGGGCCTTCATCGCCGAGGAGGGTGGCTATTGGTGGCCCTGGACTATAGCCAGA
TAGAGCTCAGGGTGCTGGCCCACCTCTCCGGCGACGAGAACCTGATCCGGGTCTTCCAGGAGGGGCGGGACATCCACACG
GAGACCGCCAGCTGGATGTTCGGCGTCCCCCGGGAGGCCGTGGACCCCCTGATGCGCCGGGCGGCCAAGACCATCAACTT
CGGGGTCCTCTACGGCATGTCGGCCCACCGCCTCTCCCAGGAGCTAGCCATCCCTTACGAGGAGGCCCAGGCCTTCATTG
AGCGCTACTTTCAGAGCTTCCCCAAGGTGCGGGCCTGGATTGAGAAGACCCTGGAGGAGGGCAGGAGGCGGGGGTACGTG
GAGACCCTCTTCGGCCGCCGCCGCTACGTGCCAGACCTAGAGGCCCGGGGCCCGCGCCGGGCGCCGCGTCGTCTGGTGAA
GAGCGTGCGGGAGGCGGCCGAGCGCATGGCCTTCAACATGCCCGTCCAGGGCACCGCCGCCGACCTCATGAAGCTGGCTA
TGGTGAAGCTCTTCCCCAGGCTGGAGGAAATGGGGGCCAGGATGCTCCTTCAGGTCCACGACGAGCTGGTCCTCGAGGCC
CCAAAAGAGAGGGCGGAGGCCGTGGCCCGGCTGGCCAAGGAGGTCATGGAGGGGGTGTATCCCCTGGCCGTGCCCCTGGA
GGTGGAGGTGGGGATAGGGGAGGACTGGCTCTCCGCCAAGGAGTGA

Taq 9aa amino acid sequence            SEQ ID NO: 12

MRGMLPLFEPKGRVLLVDGHHLAYRTFHALKGLTTSRGEPVQAVYGFAKSLLKALKEDGDAVIVVFDAKAPSFRHEAYGG
YKAGRAPTPEDFPRQLALIKELVDLLGLARLEVPGYEADDVLASLAKKAEKEGYEVRILTADKDLYQLLSDRIHVLHPEG
YLITPAWLWEKYGLRPDQWADYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWPPPEGAFVGFVLSRKEPMWAD
LLALAAARGGRVHRAPEPYKALRDLKEARGLLAKDLSVLALREGLGLPPGDDPMLLAYLLDPSNTTPEGVARRYGGEWTE
EAGERAALSERLFANLWGRLEGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTKLKSTYIDPLPDLIHPRTGRL
HTRFNQTATATGRLSSSDPNLQNIPVRTPLGQRIRRAFIAEEGWLLVALDYSQIELRVLAHLSGDENLIRVFQEGRDIHT
ETASWMFGVPREAVDPLMRRAAKTINFGVLYGMSAHRLSQELAIPYEEAQAFIERYFQSFPKVRAWIEKTLEEGRRRGYV
ETLFGRRRYVPDLEARGPRRAPRRLVKSVREAAERMAFNMPVQGTAADLMKLAMVKLFPRLEEMGARMLLQVHDELVLEA
PKERAEAVARLAKEVMEGVYPLAVPLEVEVGIGEDWLSAKE

FIG. 8

Taq Exo⁻ + 9aa nucleotide sequence                                       SEQ ID NO: 26

```
ATGAGGGGGATGCTGCCCCTCTTTGAGCCCAAGGGCCGGGTCCTCCTGGTGGACGGCCACCACCTGGCCTACCGCACCTT
CCACGCCCTGAAGGGCCTCACCACCAGCCGGGGGGAGCCGGTGCAGGCGGTCTACGGCTTCGCCAAGAGCCTCCTCAAGG
CCCTCAAGGAGGACGGGGACGCGGTGATCGTGGTCTTTGACGCCAAGGCCCCCTCCTTCCGCCACGAGGCCTACGGGGGG
TACAAGGCGGGCCGGGCCCCCACGCCGGAGGACTTTCCCCGGCAACTCGCCCTCATCAAGGAGCTGGTGGACCTCCTGGG
GCTGGCGCGCCTCGAGGTCCCGGGCTACGCGGCGGCCGACGTCCTGGCCAGCCTGGCCAAGAAGGCGGAAAAGGAGGGCT
ACGAGGTCCGCATCCTCACCGCCGCCAAAGCCCTTTACCAGCTCCTTTCCGACCGCATCCACGTCCTCCACCCCGAGGGG
TACCTCATCACCCCGGCCTGGCTTTGGGAAAAGTACGGCCTGAGGCCCGACCAGTGGGCCGACTACCGGGCCCTGACCGG
GGACGAGTCCGACAACCTTCCCGGGGTCAAGGGCATCGGGGAGAAGACGGCGAGGAAGCTTCTGGAGGAGTGGGGGAGCC
TGGAAGCCCTCCTCAAGAACCTGGACCGGCTGAAGCCCGCCATCCGGGAGAAGATCCTGGCCCACATGGACGATCTGAAG
CTCTCCTGGGACCTGGCCAAGGTGCGCACCGACCTGCCCCTGGAGGTGGACTTCGCCAAAAGGCGGGAGCCCGACCGGGA
GAGGCTTAGGGCCTTTCTGGAGAGGCTTGAGTTTGGCAGCCTCCTCCACGAGTTCGGCCTTCTGGAAAGCCCCAAGGCCC
TGGAGGAGGCCCCCTGGCCCCCGCCGGAAGGGGCCTTCGTGGGCTTTGTGCTTTCCCGCAAGGAGCCCATGTGGGCCGAT
CTTCTGGCCCTGGCCGCCGCCAGGGGGGCCCGGGTCCACCGGGCCCCCGAGCCTTATAAAGCCCTCAGGGACCTGAAGGA
GGCGCGGGGGCTTCTCGCCAAAGACCTGAGCGTTCTGGCCCTGAGGGAAGGCCTTGGCCTCCCGCCCGGCGACGACCCCA
TGCTCCTCGCCTACCTCCTGGACCCTTCCAACACCACCCCCGAGGGGGTGGCCCGGCGCTACGGCGGGGAGTGGACGGAG
GAGGCGGGGGAGCGGGCCGCCCTTTCCGAGAGGCTCTTCGCCAACCTGTGGGGGAGGCTTGAGGGGGAGGAGAGGCTCCT
TTGGCTTTACCGGGAGGTGGAGAGGCCCCTTTCCGCTGTCCTGGCCCACATGGAGGCCACGGGGGTGCGCCTGGACGTGG
CCTATCTCAGGGCCTTGTCCCTGGAGGTGGCCGAGGAGATCGCCCGGCCTCGAGGCCGAGGTCTTCCGCCTGGCCGGCCAC
CCCTTCAACCTCAACTCCCGGGACCAGCTGGAAAGGGTCCTCTTTGACGAGCTAGGGCTTCCCGCCATCGGCAAGACGGA
GAAGACCGGCAAGCGCTCCACCAGCGCCGCCGTCCTGGAGGCCCTCCGCGAGGCCCACCCCATCGTGGAGAAGATCCTGC
AGTACCGGGAGCTCACCAAGCTGAAGAGCACCTACATTGACCCCTTGCCGGACCTCATCCACCCCAGGACGGGCCGCCTC
CACACCCGCTTCAACCAGACGGCCACGGCCACGGGCAGGCTAAGTAGCTCCGATCCCAACCTCCAGAACATCCCCGTCCG
CACCCCGCTTGGGCAGAGGATCCGCCGGGCCTTCATCGCCGAGGAGGGTGGCTATTGGTGGCCCTGGACTATAGCCAGA
TAGAGCTCAGGGTGCTGGCCCACCTCTCCGGCGACGAGAACCTGATCCGGGTCTTCCAGGAGGGGCGGGACATCCACACG
GAGACCGCCAGCTGGATGTTCGGCGTCCCCCGGGAGGCCGTGGACCCCCTGATGCGCCGGGCGGCCAAGACCATCAACTT
CGGGGTCCTCTACGGCATGTCGGCCCACCGCCTCTCCCAGGAGCTAGCCATCCCTTACGAGGAGGCCCAGGCCTTCATTG
AGCGCTACTTTCAGAGCTTCCCCAAGGTGCGGGCCTGGATTGAGAAGACCCTGGAGGAGGGCAGGAGGCGGGGGTACGTG
GAGACCCTCTTCGGCCGCCGCCGCTACGTGCCAGACCTAGAGGCCCGGGGCCCGCGCCGGGCGCCGCGTCGTCTGGTGAA
GAGCGTGCGGGAGGCGGCCGAGCGCATGGCCTTCAACATGCCCGTCCAGGGCACCGCCGCCGACCTCATGAAGCTGGCTA
TGGTGAAGCTCTTCCCCAGGCTGGAGGAAATGGGGGCCAGGATGCTCCTTCAGGTCCACGACGAGCTGGTCCTCGAGGCC
CCAAAAGAGAGGGCGGAGGCCGTGGCCCGGCTGGCCAAGGAGGTCATGGAGGGGGTGTATCCCCTGGCCGTGCCCCTGGA
GGTGGAGGTGGGGATAGGGGAGGACTGGCTCTCCGCCAAGGAGTGA
```

Taq Exo⁻ + 9aa amino acid sequence                                          SEQ ID NO: 14

```
MRGMLPLFEPKGRVLLVDGHHLAYRTFHALKGLTTSRGEPVQAVYGFAKSLLKALKEDGDAVIVVFDAKAPSFRHEAYGG
YKAGRAPTPEDFPRQLALIKELVDLLGLARLEVPGYAAADVLASLAKKAEKEGYEVRILTAAKALYQLLSDRIHVLHPEG
YLITPAWLWEKYGLRPDQWADYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWPPPEGAFVGFVLSRKEPMWAD
LLALAAARGGRVHRAPEPYKALRDLKEARGLLAKDLSVLALREGLGLPPGDDPMLLAYLLDPSNTTPEGVARRYGGEWTE
EAGERAALSERLFANLWGRLEGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTKLKSTYIDPLPDLIHPRTGRL
HTRFNQTATATGRLSSSDPNLQNIPVRTPLGQRIRRAFIAEEGWLLVALDYSQIELRVLAHLSGDENLIRVFQEGRDIHT
ETASWMFGVPREAVDPLMRRAAKTINFGVLYGMSAHRLSQELAIPYEEAQAFIERYFQSFPKVRAWIEKTLEEGRRRGYV
ETLFGRRRYVPDLEARGPRRAPRRLVKSVREAAERMAFNMPVQGTAADLMKLAMVKLFPRLEEMGARMLLQVHDELVLEA
PKERAEAVARLAKEVMEGVYPLAVPLEVEVGIGEDWLSAKE
```

→ Large unit
→ middle unit
→ small unit

➡ Large unit
➡ middle unit

DNA POLYMERASES

TECHNICAL FIELD

The present invention relates to novel DNA polymerases. The DNA polymerases of this invention are particularly useful for PCR.

BACKGROUND ART

DNA polymerases are enzymes that can synthesize new DNA strands along template DNA strands in vitro. DNA polymerases can synthesize new DNA strands from a template DNA, an oligonucleotide used as a primer, and four types of deoxynucleotides (dATP, dGTP, dCTP, and dTTP). DNA polymerases are also used in many genetic engineering techniques, including nucleotide sequencing and PCR.

Thermostability of polymerases is essential for PCR, and the current protocol of nucleotide sequencing generally uses the cycle sequencing method using a thermostable DNA polymerase as a standard technique. In order to find a thermostable enzyme, one would usually search enzymes produced by thermophilic microorganisms. Among thermophilic bacteria, those which proliferate at an optimum growth temperature of at least 80° C. are particularly referred to as "hyperthermophilic bacteria" and serve as excellent resources for thermostable enzymes. Taq DNA polymerases (also referred to as "Taq polymerases") which are currently widely used in PCR were originally isolated from the thermophilic eubacterium *Thermus aquaticus*.

Based on the similarity in amino acid sequences, DNA polymerases are categorized into seven groups: Families A, B, C, D, E, X and Y. Enzymes belonging to the same family basically exhibit very similar properties. The enzymes that are in practical use are those belonging to Families A and B.

Family A enzymes have superior performance in recognizing dideoxynucleotides as substrates and are most appropriate for nucleotide sequencing. Thus, the enzymes contained in currently commercially available sequencing kits are all those which belong to Family A and are derived from thermophilic eubacteria. In PCR, Family A and B enzymes are selectively used depending on the purpose.

Family B enzymes are not suitable for nucleotide sequencing because of poor incorporation of dideoxynucleotides but have 3'-5' exonuclease activity which is involved in the accuracy in synthesizing DNA strands according to the sequences of template strands during amplification, this family of enzymes produces less errors than Family A enzymes such as Taq polymerases without its exonuclease activity. The Family B enzymes that are commercialized are those derived from hyperthermophilic archaea. In order to perform PCR more accurately, it is advisable to use Family B enzymes, whereas in order to amplify long-chain DNA, Family A enzymes can be selected due to superior extensibility and superior DNA synthesis efficiency.

Comparison between the two DNA polymerases that are derived from bacteria belonging to the genus *Thermus* and which have been up to now widely used as PCR enzymes shows that Taq DNA polymerase only has weak reverse transcription activity, while Tth DNA polymerase (also referred to as "Tth polymerase") derived from *Thermus thermophilus* has significantly strong reverse transcription activity. This property of Tth polymerase is utilized in a simple RT-PCR technology in which a single enzyme is used in a single reaction tube to synthesize cDNA from mRNA by reverse transcription activity and then amplify the synthesized cDNA. Since optimum temperature of this enzyme is high, the enzyme makes it possible to perform a reverse transcription reaction at relatively high temperatures (around 60° C.) and is also effective for the reverse transcription of RNA which easily forms a three-dimensional structure, but the enzyme is not suitable for the synthesis of long cDNAs like those reaching as long as several kilo bases in length.

PCR is a gene analysis technology that is widely used throughout the world and as a routinely utilized technique. Accordingly, there is a need for a DNA polymerase that is more convenient, easier-to-use, and more reliable, and it is also desired to provide various DNA polymerases that can amplify various DNAs appropriately depending on the template to be used as well as purpose to be needed for the PCR such as extensibility, rapidity, and accuracy.

As regards modification of Taq polymerases, there have been hitherto reports stating that primers were designed based on the segments of an amino acid sequence highly conserved in Family A DNA polymerases, each of which contains an active site, gene fragments were amplified by PCR using DNA samples derived from hot spring soil as templates, and the corresponding segments of a wild-type Taq polymerase gene were substituted by the amplified fragments, whereby obtained were chimeric DNA polymerases with higher extension activity than Taq polymerase (Patent Documents 1 and 2). Another report showed that on the basis of metagenomic analysis and the three-dimensional structure information of DNA polymerases, one or more mutations were introduced that produce an increased the total electric charges of those of glutamic acid at position 742 and alanine at position 743 in an amino acid sequence of a Taq polymerase, whereby obtained was a modified Taq polymerase that is superior to the Taq polymerase in at least one of: primer extension activity; binding activity on a primer annealed to a template DNA; and PCR performance (Patent Document 3).

CITATION LIST

Patent Documents

Patent Document 1: Japanese Patent Application Publication No. JP 2006-101791
Patent Document 2: Japanese Patent Application Publication No. JP 2006-204267
Patent Document 3: Japanese Patent No. JP 4193997

SUMMARY OF INVENTION

Technical Problem

The present inventors made detailed comparison between the amino acid sequences of Taq polymerases and Tth polymerases, focusing on the difference in the properties associated with their amino acid sequence identity (about 80%) and reverse transcription activity. However, based on this comparison alone, it was difficult to predict on what the difference in their properties depends.

On the other hand, the inventors have accumulated the results of the study in which the properties of DNA polymerases derived from a diverse range of organisms are reflected as those of chimeric Taq polymerases by the following method: hot spring soil samples are collected from various places, DNAs are directly extracted from the samples, fragments of DNA polymerase genes possessed by various kinds of organisms contained in the samples are amplified by PCR based on the obtained DNAs (metagenomes), and the resulting fragments are recombined in vitro with the homologous regions of Taq polymerase genes, whereby chimeric enzymes are constructed. It is, of course, ideal that the gene obtained from a metagenome contain a full-length sequence, but many metagenomic DNAs extracted from environmental samples are often fragmented or damaged; thus, it is a very difficult task to obtain a full-length gene. Therefore, we constructed a study system in which a gene segment encoding an active center that significantly affects the activity of a DNA polymerase and peripheral regions thereof is obtained from a metagenome, and the obtained segment is recombined with the homologous region of a Taq polymerase gene to create a chimeric enzyme gene, so that it can be considered that the obtained gene fragment can directly affect the basic properties of a DNA polymerase.

We created a phylogenetic tree (not shown in the present application) by checking the results of determination of the activities of many chimeric Taq polymerases constructed as described above, against each other, and comparing the sequences of the gene fragments that are derived from metagenomic DNAs and which were recombined into wild-type Taq polymerases. As a result of predicting the factors that might change the activities of the chimeric Taq polymerases, we found the chimeric Taq polymerases 8-16, 18-7, 1-8, and 3-7 which have significantly strong reverse transcription activity as compared with the wild-type Taq polymerases.

First, we compared the sequences of 8-16, a Taq polymerase, and a Tth polymerase with each other but did not find any amino acid residue that is common between 8-16 and the Tth polymerase but is different between 8-16 and the Taq polymerase. However, among ten amino acid residues that are different between the Taq and Tth polymerases, there were three amino acid residues that are completely different in nature between these three polymerases. Thus, we focused on these three amino acid residues and decided to introduce mutations to them.

Next, we compared the sequence of 18-7 with each of the sequences of a Taq polymerase and a Tth polymerase to thereby search for an amino acid residue that is common between 18-7 and the Tth polymerase which both have reverse transcription activity but not common between 18-7 and the Taq polymerase, and, as a result, four amino acid residues were found. Among them, there was one amino acid residue that is greatly different in nature between 18-7/Tth polymerase and the Taq polymerase; thus, we decided to introduce a mutation to this amino acid residue.

Further, as regards 1-8 and 3-7, these chimeric polymerases have strong primer extension activity and reverse transcription activity, whereas there was a chimeric enzyme (1-20) that has almost the same sequence but is extremely weak in activity. We compared the sequences of the three enzymes: 1-8, 3-7 as well as 1-20 mentioned above, to find two amino acids that are completely inconsistent between these sequences. And we selected the one that is only inconsistent in 1-20 which is greatly different in activity, and decided to introduce a mutation to it.

The inventors also found that the above-mentioned mutants obtained by inserting the nine amino acids (GPRRAPRRL) into a certain segment of the Taq polymerase based on the metagenome information are weak in reverse transcription activity per se but have particularly excellent extensibility when used in reverse transcription reaction. The inventors thus created mutant DNA polymerases having presumably very useful properties, and completed the present invention.

The present invention provides the following:
[1] A DNA polymerase which is any one of (a1) to (c1) mentioned below:
(a1) a DNA polymerase comprising an amino acid sequence modified from the amino acid sequence of SEQ ID NO: 8 by inserting -$A_{737}$-$A_{738}$-$A_{739}$-$A_{740}$-$A_{741}$-$A_{742}$-$A_{743}$-$A_{744}$-$A_{745}$- between the amino acid residue at position 736 and the amino acid residue at position 737, wherein:
$A_{737}$ is an amino acid residue having a non-polar aliphatic side chain;
$A_{738}$ is an amino acid residue having a non-polar aliphatic side chain;
$A_{739}$ is an amino acid residue having a positively charged side chain;
$A_{740}$ is an amino acid residue having a positively charged side chain;
$A_{741}$ is an amino acid residue having a non-polar aliphatic side chain;
$A_{742}$ is an amino acid residue having a non-polar aliphatic side chain;
$A_{743}$ is any given amino acid residue;
$A_{744}$ is an amino acid residue having a positively charged side chain; and
$A_{745}$ is an amino acid residue having a non-polar aliphatic side chain;
(b1) a DNA polymerase comprising an amino acid sequence modified from the amino acid sequence of the DNA polymerase as recited in (a1), by substituting, deleting, inserting and/or adding one to nine amino acid residues which exclude the amino acid sequence inserted between an amino acid residue corresponding to position 736 and an amino acid residue corresponding to position 737; and
(c1) a DNA polymerase comprising an amino acid sequence that is modified from an amino acid sequence of a Family A DNA polymerase derived from a thermophilic eubacterium, by inserting -$A_{737}$-$A_{738}$-$A_{739}$-$A_{740}$-$A_{741}$-$A_{742}$-$A_{743}$-$A_{745}$- between amino acid residues corresponding to the amino acid residues at positions 736 and 737 in the amino acid sequence of SEQ ID NO: 8, and which has at least 80% sequence identity to the amino acid sequence of the DNA polymerase as recited in (a1);
[2] The DNA polymerase as recited in [1], wherein in the amino acid sequence -$A_{737}$-$A_{738}$-$A_{739}$-$A_{740}$-$A_{741}$-$A_{742}$-$A_{743}$-$A_{744}$-$A_{745}$- contained in the DNA polymerase of (a1):
$A_{737}$ is a glycine residue;
$A_{738}$ is a proline residue;
$A_{739}$ is an arginine residue;
$A_{740}$ is an arginine residue;
$A_{741}$ is an alanine residue;
$A_{742}$ is a proline residue;
$A_{743}$ is any given amino acid residue;
$A_{744}$ is an arginine residue; and
$A_{745}$ is a leucine residue;
[3] The DNA polymerase as recited in [1] or [2], wherein $A_{743}$ is an arginine residue, a lysine residue, a histidine residue, an alanine residue, a glutamine residue, a glutamic acid residue, or a threonine residue;
[4] The DNA polymerase as recited in any one of [1] to [3], wherein the DNA polymerase comprises the amino acid sequence represented by SEQ ID NO: 24;
[5] A polynucleotide which is any one of (A1) to (D1) mentioned below:
(A1) a polynucleotide comprising the nucleotide sequence of SEQ ID NO: 23;
(B1) a polynucleotide comprising a nucleotide sequence encoding the DNA polymerase as recited in any one of [1] to [4];

(C1) a polynucleotide that hybridizes under stringent conditions with a polynucleotide comprising a complementary sequence to the nucleotide sequence of the polynucleotide as recited in (A1), and which encodes a DNA polymerase (with the proviso that a segment inserted between an amino acid residue corresponding to position 736 and an amino acid residue corresponding to position 737 is the same, in terms of respective segmental elements, as the segment inserted between an amino acid residue corresponding to position 736 and an amino acid residue corresponding to position 737 in the DNA polymerase as recited in (a1) under [1]); and (D1) a polynucleotide that comprises a sequence at least 95% identical to the nucleotide sequence of the polynucleotide as recited in (A1), and which encodes a DNA polymerase (with the proviso that a segment inserted between an amino acid residue corresponding to position 736 and an amino acid residue corresponding to position 737 is the same, in terms of respective segmental elements, as the segment inserted between an amino acid residue corresponding to position 736 and an amino acid residue corresponding to position 737 in the DNA polymerase as recited in (a1) under [1]);

[6] A DNA polymerase which is any one of (a2) to (c2) mentioned below:

(a2) a DNA polymerases comprising an amino acid sequence modified from the amino acid sequence of SEQ ID NO: 8 by substituting at least one selected from the glutamic acid residue at position 117, the aspartic acid residue at position 119, the aspartic acid residue at position 142, and the aspartic acid residue at position 144 by an amino acid residue having a non-polar aliphatic side chain, and by inserting $-A_{737}-A_{738}-A_{739}-A_{740}-A_{741}-A_{742}-A_{743}-A_{745}-$ between the amino acid residue at position 736 and the amino acid residue at position 737, wherein:

$A_{737}$ is an amino acid residue having a non-polar aliphatic side chain;

$A_{738}$ is an amino acid residue having a non-polar aliphatic side chain;

$A_{739}$ is an amino acid residue having a positively charged side chain;

$A_{740}$ is an amino acid residue having a positively charged side chain;

$A_{741}$ is an amino acid residue having a non-polar aliphatic side chain;

$A_{742}$ is an amino acid residue having a non-polar aliphatic side chain;

$A_{743}$ is any given amino acid residue;

A744 is an amino acid residue having a positively charged side chain; and $A_{745}$ is an amino acid residue having a non-polar aliphatic side chain;

(b2) a DNA polymerase comprising an amino acid sequence modified from the amino acid sequence of the DNA polymerase as recited in (a2), by substituting, deleting, inserting and/or adding one to nine amino acid residues which exclude amino acid residues corresponding to positions 117, 119, 142 and 144 and the segment inserted between the amino acid residue at position 736 and the amino acid residue at position 737; and (c2) a DNA polymerase comprising a sequence that is at least 95% identical, and also identical in terms of the amino acid residues corresponding to positions 117, 119, 142 and 144 and the segment inserted between the amino acid residue at position 736 and the amino acid residue at position 737, to the amino acid sequence of the DNA polymerase as recited in (a2);

[7] The DNA polymerases as recited in [6], wherein in the amino acid sequence $-A_{737}-A_{738}-A_{739}-A_{740}-A_{741}-A_{742}-A_{743}-A_{744}-A_{745}-$ contained in the DNA polymerase of (a2):

$A_{737}$ is a glycine residue;
$A_{738}$ is a proline residue;
$A_{739}$ is an arginine residue;
$A_{740}$ is an arginine residue;
$A_{741}$ is an alanine residue;
$A_{742}$ is a proline residue;
$A_{743}$ is any given amino acid residue;
$A_{744}$ is an arginine residue; and
$A_{745}$ is a leucine residue;

[8] The DNA polymerase as recited in [6] or [7], wherein $A_{743}$ is an arginine residue, a lysine residue, a histidine residue, an alanine residue, a glutamine residue, a glutamic acid residue, or a threonine residue;

[9] The DNA polymerase as recited in any one of [6] to [8], wherein the DNA polymerase comprises the amino acid sequence represented by SEQ ID NO: 14;

[10] A polynucleotide which is any one of (A2) to (D2) mentioned below:

(A2) a polynucleotide comprising the nucleotide sequence of SEQ ID NO: 13;

(B2) a polynucleotide comprising a nucleotide sequence encoding the DNA polymerase as recited in any one of [6] to [9];

(C2) a polynucleotide that hybridizes under stringent conditions with a polynucleotide comprising a complementary sequence to the nucleotide sequence of the polynucleotide as recited in (A2), and which encodes a DNA polymerase (with the proviso that amino acid residues corresponding to positions 117, 119, 142 and 144 and a segment inserted between the amino acid residue at position 736 and the amino acid residue at position 737 are each the same as the amino acid residues corresponding to positions 117, 119, 142 and 144 and the segment inserted between the amino acid residue at position 736 and the amino acid residue at position 737 in the DNA polymerase as recited in (a1) under [6]); and (D2) a polynucleotide that comprises a sequence at least 95% identical to the nucleotide sequence of the polynucleotide as recited in (A2), and which encodes a DNA polymerase whose primer extension activity with DNA being used as a template is at least 4.00 kb/U·min (with the proviso that amino acid residues corresponding to positions 117, 119, 142 and 144 and a segment inserted between the amino acid residue at position 736 and the amino acid residue at position 737 are each the same as the amino acid residues corresponding to positions 117, 119, 142 and 144 and the segment inserted between the amino acid residue at position 736 and the amino acid residue at position 737 in the DNA polymerase as recited in (a2) under [6]);

[11] A recombinant vector comprising the polynucleotide as recited in [5] or [8];

[12] A transformant comprising the recombinant vector as recited in [11]; and

[13] A process for preparing the DNA polymerase as recited in any one of [1] to [4] and [6] to [9], the process comprising a step of culturing the transformant as recited in [12].

BRIEF DESCRIPTIONS OF DRAWINGS

Figure 1:
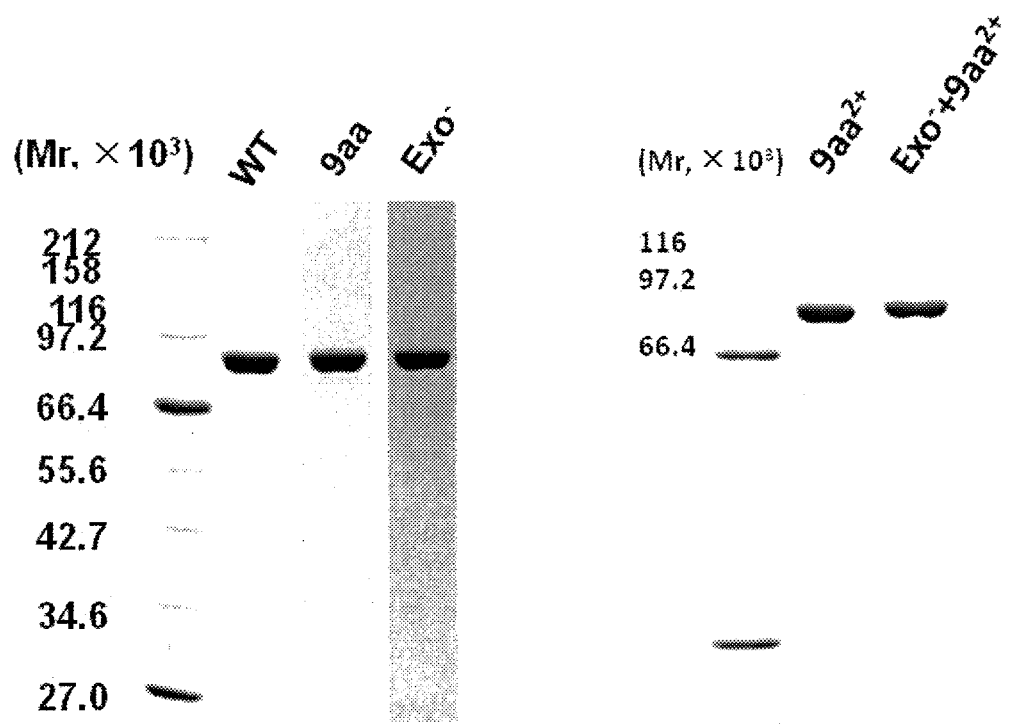
FIG. 1 shows a photograph of the SDS-PAGE gels concerning purification of Taq DNA polymerase mutants. The purity of each of the prepared Taq DNA polymerase mutants was confirmed by SDS-PAGE analysis (refer to Example 1).
Figure 2:
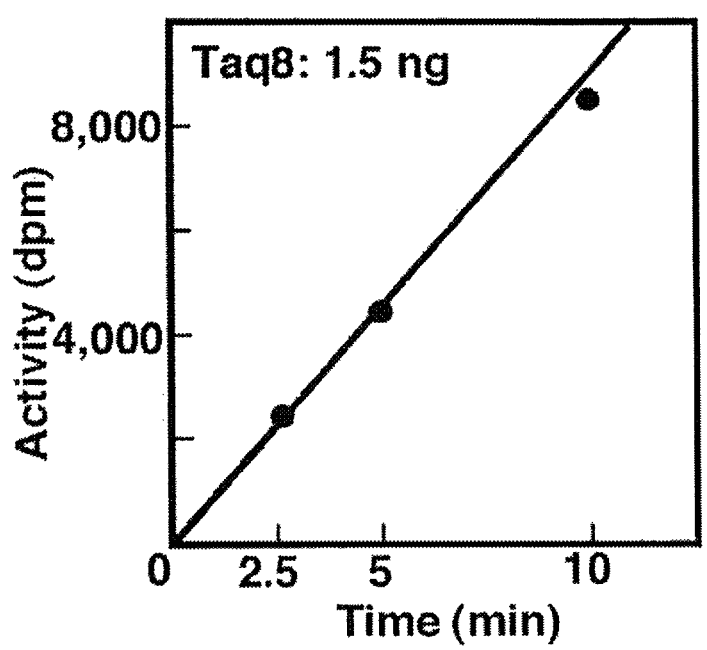
FIG. 2 shows a graph of an actual example of enzymatic activity determination by nucleotide incorporation assay (refer to Example 2). Under the conditions of this test, Taq showed an activity of $3.9 \times 10^5$ U/mg.
Figure 3:
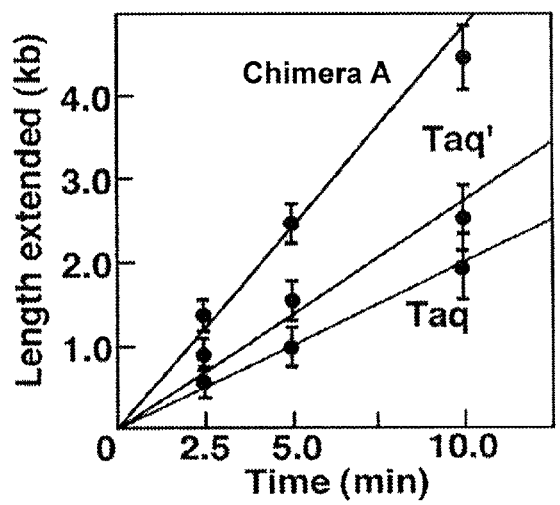

FIG. 3 shows an example of a graph for determining primer extension rate. With the amount of enzyme kept constant, a time course of primer extension reaction is taken and the extension rate can be determined by measuring the length of strand extended per unit time through alkaline agarose electrophoresis in a region where the plots lie on a straight line (refer to Example 2). Under the conditions of this test, Taq showed a rate of 4.67 kb/min/U, Taq' (Taq mutant) showed a rate of 6.67 kg/min/U, and Chimera A (the chimera created by recombining a segment of the Taq gene with a homologous region obtained from the metagenome) showed a rate of 11.20 kb/min/U.

Figure 4:
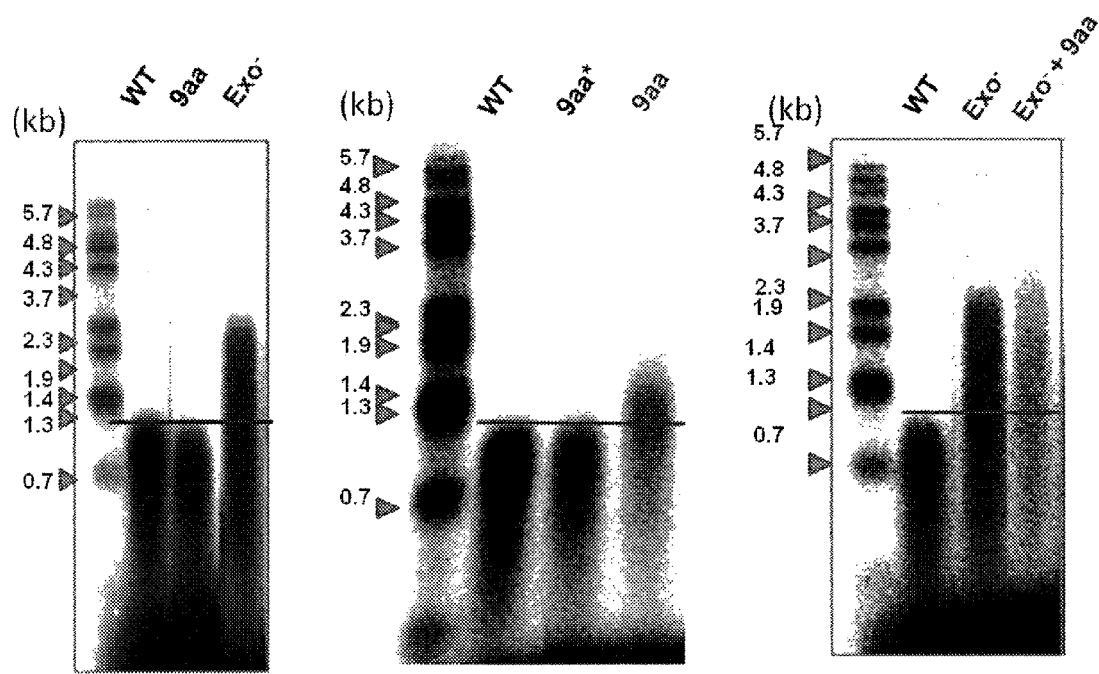

FIG. 4 shows a photograph of the alkaline agarose electrophoresis gels for comparing primer extension rates.

FIG. 5 shows the Taq WT amino acid sequence of SEQ ID NO: 8 and the Taq WT nucleotide sequence of SEQ ID NO: 7.

FIG. 6 shows the Taq Exo$^-$ amino acid sequence of SEQ ID NO: 10 and the Taq Exo$^-$ nucleotide sequence of SEQ ID NO: 9.

FIG. 7 shows the Taq 9aa amino acid sequence of SEQ ID NO: 12 and the Taq 9aa nucleotide sequence of SEQ ID NO: 11.

FIG. 8 shows the Taq Exo$^-$+9aa amino acid sequence of SEQ ID NO: 14 and the Taq Exo$^-$+9aa nucleotide sequence of SEQ ID NO: 13.

Figure 9:
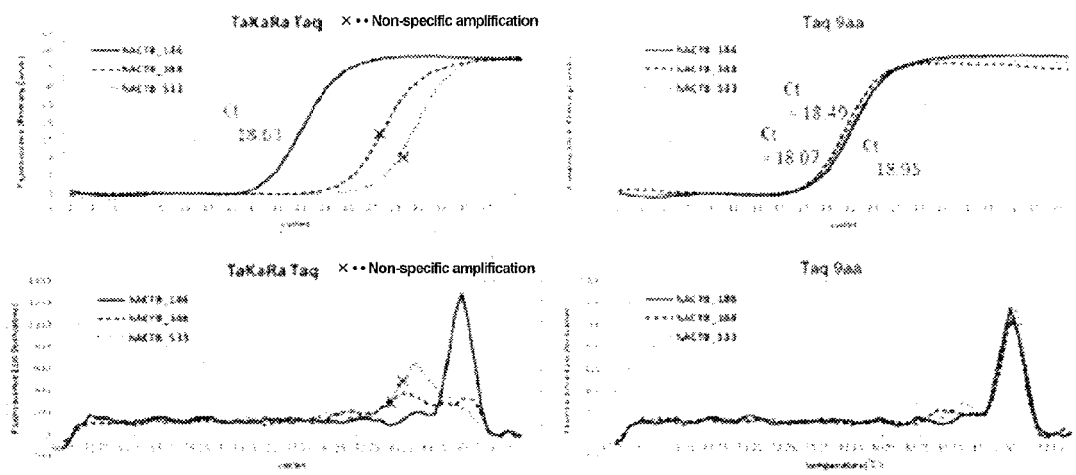

FIG. 9 shows the results of the real-time PCR performed in Example 3.

Figure 10:
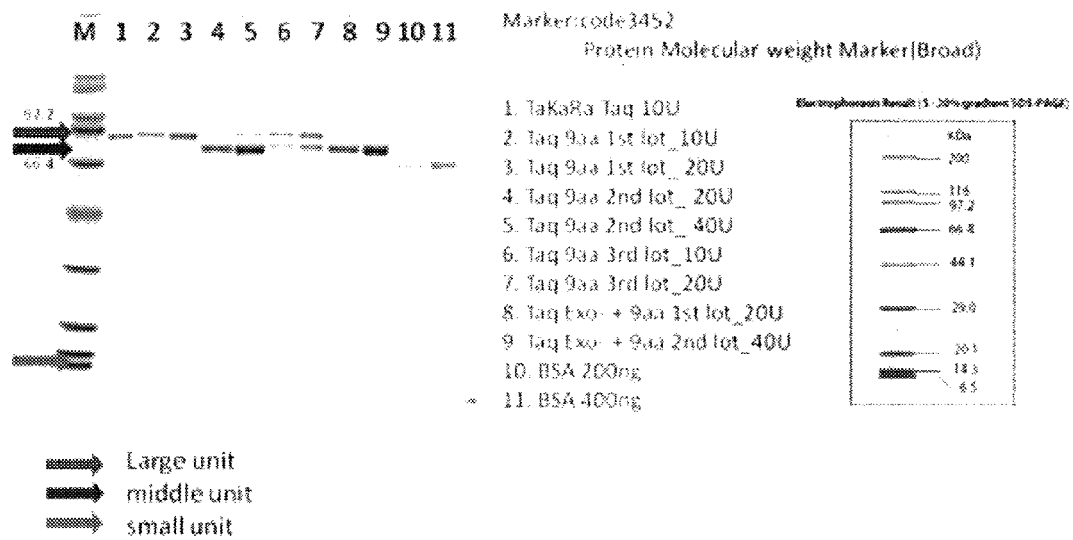

FIG. 10 shows a photograph of the SDS-PAGE gels obtained from the electrophoresis of the purified enzymes in Example 4.

Figure 11:
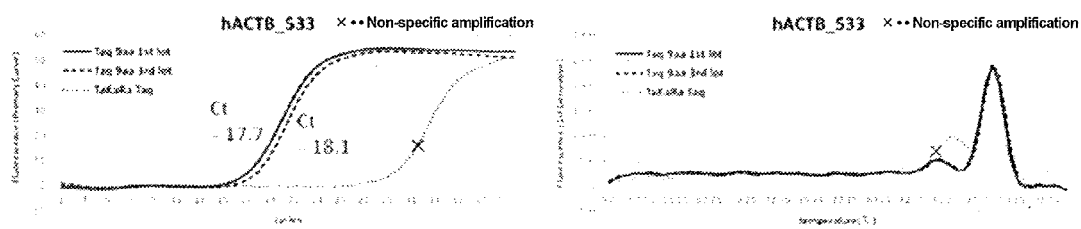

FIG. 11 shows the results of the real-time PCR performed in Example 5.

Figure 12:
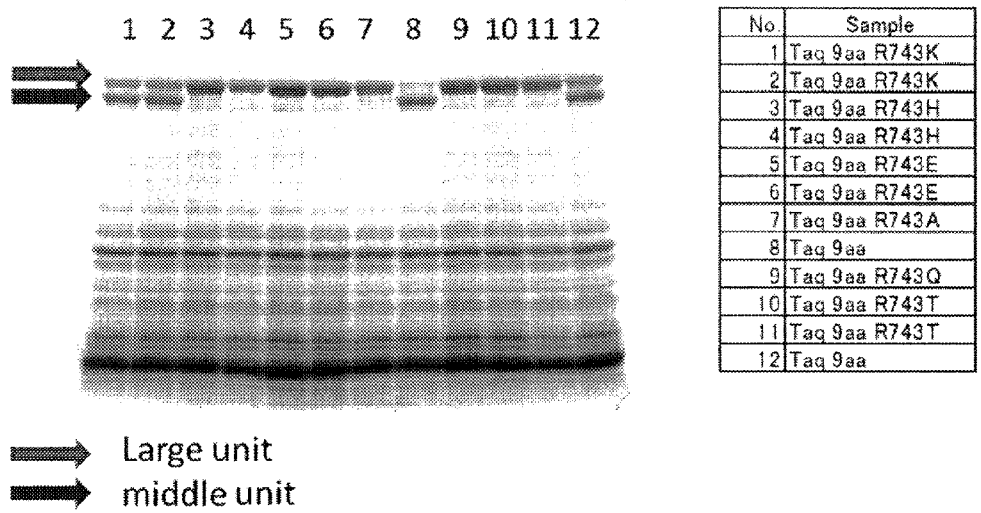

FIG. 12 shows a photograph of the SDS-PAGE gels obtained from the electrophoresis of the crudely purified DNA polymerase solutions in Example 8.

Figure 13:
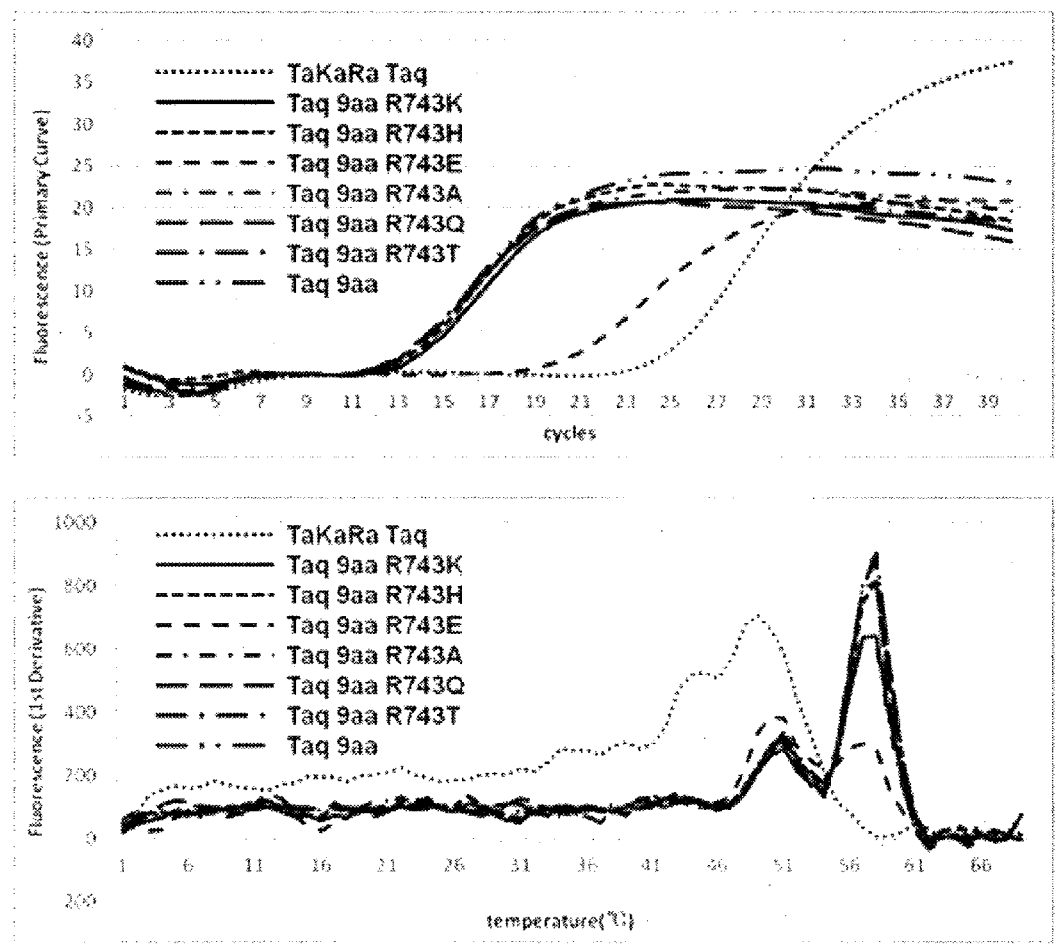

FIG. 13 shows the results of the real-time PCR performed in Example 8.

Figure 14:
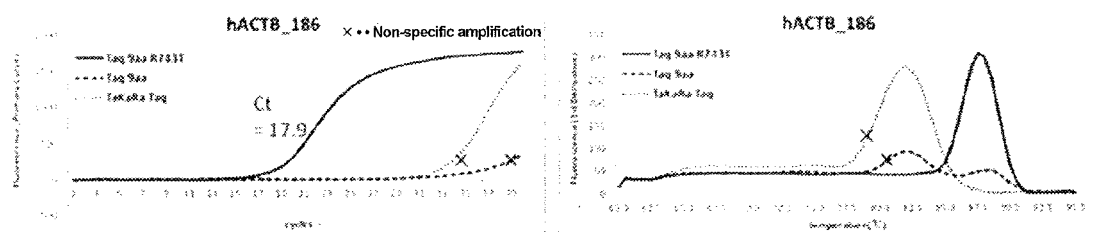

FIG. 14 shows the results of the real-time PCR performed in Example 9.

Figure 15:
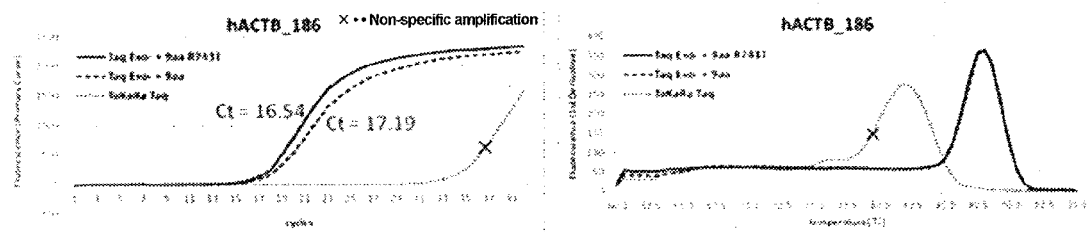

FIG. 15 shows the results of the real-time PCR performed in Example 9.

DESCRIPTION OF EMBODIMENTS

1. DNA Polymerases of the Present Invention

The present invention provides novel DNA polymerases, and more specifically mutants of Family A DNA polymerases derived from a thermophilic eubacterium.

1-1. Wild-Type Taq Polymerase and its Mutant Taq Exo$^-$ (Exo$^-$ WT)

The present inventors first made extensive studies for the purpose of creating a superior PCR enzyme by modifying a wild-type Taq polymerase, and as a result found that the mutants Taq Exo$^-$ (E117A, D119A, D142A, D144A), in which four amino acid residues presumably important for the 5'→3' exonuclease activity inherent in a Taq polymerase are converted together, are superior in extension activity to the wild-type Taq polymerase.

The amino acid sequence of the wild-type Taq polymerase and the nucleotide sequence encoding the same are respectively shown in SEQ ID NOs: 8 and 7 in the Sequence Listing which constitutes a part of the present specification. The amino acid sequence of Taq Exo$^-$ and the nucleotide sequence encoding the same are respectively shown in SEQ ID NOs: 10 and 9 in the Sequence Listing which constitutes a part of the specification.

In Taq Exo$^-$, all of the glutamic acid residue at position 117, the aspartic acid residue at position 119, the aspartic acid residue at position 142, and the aspartic acid residue at position 144 in the amino acid sequence of SEQ ID NO: 8 are substituted (SEQ ID NO: 10), but the homologues of said mutant, which have an amino acid sequence in which at least one, preferably two, more preferably three, selected from these residues are each independently substituted by an amino acid residue having a non-polar aliphatic side chain, preferably an amino acid residue selected from the group consisting of a glycine residue, an alanine residue, a valine residue, a leucine residue, an isoleucine residue, and a proline residue, and more preferably an alanine residue, can also be used in the present invention.

Taq Exo$^-$ and the homologues thereof have improved primer extension activity over wild-type Taq. More specifically, their primer extension activities with DNA being used as a template are all at least 4.00 kb/U·min, preferably at least 8.00 kb/U·min, and more preferably 9.00 kb/U*min.

1-2. Taq 9aa and Taq Exo$^-$+9aa (Exo$^-$+9aa)

On the basis of the above-mentioned wild-type Taq DNA (SEQ ID NO: 8) and Taq Exo$^-$ (SEQ ID) NO: 10), a mutant of the Taq DNA polymerase, as well as the information obtained by analyzing the metagenomes prepared from hot spring soil samples, the present inventors obtained a sequence found in some genes, which encodes the sequence presumably belonging to the same family as the Taq DNA, and constructed the mutant Taq 9aa in which nine amino acids (GPRRAPRRL (SEQ ID NO: 16)) are inserted in the wild-type Taq polymerase. Further, we found that Taq 9aa, and the mutant Taq Exo$^-$+9aa obtained by introducing a combination of said insertion mutation and the above-mentioned substitution mutation of the residues involved in 5'-3' exonuclease activity (Taq Exo$^-$), are both superior in extension activity to the wild-type Taq polymerase. Accordingly, the present invention provides Taq 9aa and homologues thereof, and polynucleotides encoding all of these and homologues of said polynucleotides ([1] to [5] noted above), as well as provides Taq Exo$^-$+9aa and homologues thereof, and polynucleotide encoding all of these and homologues of said polynucleotides ([7] to [10] noted above).

The amino acid sequence of Taq 9aa and the nucleotide sequence encoding the same are respectively shown in SEQ ID NOs: 12 and 11 in the Sequence Listing which constitutes a part of the present specification. The amino acid sequence of Taq Exo$^-$+9aa and the nucleotide sequence encoding the same are respectively shown in SEQ ID NOs: 14 and 13 in the Sequence Listing which constitutes a part of the specification.

In Taq 9aa or Taq Exo$^-$+9aa, the amino acid sequence consisting of nine amino acids, $-A_{737}-A_{738}-A_{739}-A_{740}-A_{741}-A_{742}-A_{743}-A_{744}-A_{745}-$, is inserted between an amino acid residue corresponding to position 736 and an amino acid residue corresponding to position 737 in the amino acid sequence (SEQ ID NO: 8) of the wild-type Taq polymerase or the amino acid sequence (SEQ ID) NO: 10) of Taq Exo$^-$.

In the inserted nine amino acid sequence:

$A_{737}$ is an amino acid residue having a non-polar aliphatic side chain, preferably an amino acid residue selected from the group consisting of a glycine residue, an alanine residue, a valine residue, a leucine residue, an isoleucine residue, and a proline residue, and more preferably a glycine residue;

$A_{738}$ is an amino acid residue having a non-polar aliphatic side chain, preferably an amino acid residue selected from the group consisting of a glycine residue, an alanine residue, a valine residue, a leucine residue, an isoleucine residue, and a proline residue, and more preferably a proline residue;

$A_{739}$ is an amino acid residue having a positively charged side chain, preferably an amino acid residue selected from the group consisting of a lysine residue, an arginine residue, and a histidine residue, and more preferably an arginine residue;

$A_{740}$ is an amino acid residue having a positively charged side chain, preferably an amino acid residue selected from the group consisting of a lysine residue, an arginine residue, and a histidine residue, and more preferably an arginine residue;

$A_{741}$ is an amino acid residue having a non-polar aliphatic side chain, preferably an amino acid residue selected from the group consisting of a glycine residue, an alanine residue, a valine residue, a leucine residue, an isoleucine residue, and a proline residue, and more preferably an alanine residue;

$A_{742}$ is an amino acid residue having a non-polar aliphatic side chain, preferably an amino acid residue selected from the group consisting of a glycine residue, an alanine residue, a valine residue, a leucine residue, an isoleucine residue, and a proline residue, and more preferably a proline residue;

$A_{743}$ is any given amino acid residue, preferably an amino acid residue selected from the group consisting of an arginine residue, a lysine residue, a histidine residue, an alanine residue, a glutamine residue, a glutamic acid residue, or a threonine residue, and more preferably an arginine residue;

$A_{744}$ is an amino acid residue having a positively charged side chain, preferably an amino acid residue selected from the group consisting of a lysine residue, an arginine residue, and a histidine residue, and more preferably an arginine residue; and $A_{745}$ is an amino acid residue having a non-polar aliphatic side chain, preferably an amino acid residue selected from the group consisting of a glycine residue, an alanine residue, a valine residue, a leucine residue, an isoleucine residue, and a proline residue, and more preferably a leucine residue.

The nine amino acids to be inserted are most preferably GPGQAPRAL (Gly Pro Gly Gln Ala Pro Arg Ala Leu: SEQ ID NO: 15) or GPRRAPRRL (Gly Pro Arg Arg Ala Pro Arg Ala Leu: SEQ ID NO: 16).

Taq 9aa, Taq Exo⁻+9aa and the homologues thereof have improved primer extension activity over the wild-type Taq polymerase. More specifically, their primer extension activities with DNA being used as a template are all at least 4.00 kb/U·min, preferably at least 8.00 kb/U·min, more preferably at least 9.00 kb/U·min, and still more preferably 10.0 kb/U·min.

1-3. Taq 9aa+R743X (9aa+R743X) and Taq Exo⁻+9aa+R743X (Taq Exo⁻+9aa R743X)

In addition, the present inventors found that Taq 9aa and Taq Exo⁻+9aa have a higher reaction rate than the wild-type Taq polymerase and are useful for rapid PCR. We also found that in the case where in the above-mentioned nine amino acids inserted between an amino acid residue corresponding to position 736 and an amino acid residue corresponding to position 737, $A_{743}$ is arginine, then peptide linkage cleavage may occur at a particular site(s) of Taq 9aa or Taq Exo⁻+9aa during their preparation process, and that the Taq 9aa or Taq Exo⁻+9aa in which peptide linkage cleavage has occurred at the particular site(s) has a lower reaction rate than they originally had. Furthermore, we found that this problem can be solved by substituting the arginine residue at position 743 of Taq 9aa or Taq Exo⁻+9aa by another amino acid residue. Accordingly, the present invention provides Taq 9aa+R743X and homologues thereof, and polynucleotides encoding all of these and homologues of said polynucleotides ([1] to [10] noted above).

Taq 9aa+R743X comprises the amino acid sequence of SEQ ID NO: 8 modified by inserting the amino acid sequence consisting of nine amino acids, -$A_{737}$-$A_{738}$-$A_{739}$-$A_{740}$-$A_{741}$-$A_{742}$-$A_{743}$-$A_{744}$-$A_{745}$-, between the amino acid residue at position 736 and the amino acid residue at position 737, and Taq Exo⁻+9aa R743X comprises the amino acid sequence of SEQ ID NO: 14 modified by inserting the same nine amino acid sequence between the amino acid residue at position 736 and the amino acid residue at position 737.

In the inserted nine amino acid sequence:

$A_{737}$ is an amino acid residue having a non-polar aliphatic side chain, preferably a glycine residue, an alanine residue, a valine residue, a leucine residue, an isoleucine residue, or a proline residue, and more preferably a glycine residue;

$A_{738}$ is an amino acid residue having a non-polar aliphatic side chain, preferably a glycine residue, an alanine residue, a valine residue, a leucine residue, an isoleucine residue, or a proline residue, and more preferably a proline residue;

$A_{739}$ is an amino acid residue having a positively charged side chain, preferably a lysine residue, an arginine residue, or a histidine residue, and more preferably an arginine residue;

$A_{740}$ is an amino acid residue having a positively charged side chain, preferably a lysine residue, an arginine residue, or a histidine residue, and more preferably an arginine residue;

$A_{741}$ is an amino acid residue having a non-polar aliphatic side chain, preferably a glycine residue, an alanine residue, a valine residue, a leucine residue, an isoleucine residue, or a proline residue, and more preferably an alanine residue;

$A_{742}$ is an amino acid residue having a non-polar aliphatic side chain, preferably a glycine residue, an alanine residue, a valine residue, a leucine residue, an isoleucine residue, or a proline residue, and more preferably a proline residue;

$A_{743}$ is any given amino acid residue, preferably an arginine residue, a lysine residue, a histidine residue, an alanine residue, a glutamine residue, a glutamic acid residue, or a threonine residue, more preferably a lysine residue, a histidine residue, an alanine residue, a glutamine residue, or a threonine residue, and still more preferably a threonine residue;

$A_{744}$ is an amino acid residue having a positively charged side chain, preferably a lysine residue, an arginine residue, or a histidine residue, and more preferably an arginine residue; and $A_{745}$ is an amino acid residue having a non-polar aliphatic side chain, preferably a glycine residue, an alanine residue, a valine residue, a leucine residue, an isoleucine residue, or a proline residue, and more preferably a leucine residue.

The homologues of Taq 9aa+R743X or Taq Exo⁻+9aa R743X are exemplified by: a DNA polymerase comprising an amino acid modified from the above-mentioned amino acid sequence of Taq 9aa+R743X or Taq Exo⁻+9aa R743X (SEQ ID NO: 24 or 26, respectively), by substituting, deleting, inserting and/or adding one to nine amino acid residues which exclude the amino acid sequence inserted between an amino acid residue corresponding to position 736 and an amino acid residue corresponding to position 737; and a DNA polymerase comprising an amino acid sequence that is modified from an amino acid sequence of a Family A DNA polymerase derived from a thermophilic eubacterium, by inserting -$A_{737}$-$A_{739}$-$A_{740}$-$A_{741}$-$A_{742}$-$A_{743}$-$A_{744}$-$A_{745}$- between an amino acid residue corresponding to the amino acid residue at position 736 and an amino acid residue corresponding to the amino acid residue at position 737 in the amino acid sequence of SEQ ID NO: 8 or SEQ ID NO: 10, and which has at least 80% sequence identity to the above-mentioned amino acid sequence of Taq 9aa+ R743X or Taq Exo⁻+9aa R743X.

Taq 9aa+R743X, Taq Exo⁻+9aa R743X, and the homologues thereof have a higher reaction rate than the wild-type DNA polymerase. The reaction rate of a DNA polymerase can typically be confirmed by the following method: a DNA polymerase whose reaction rate is to be confirmed is subjected to PCR targeting a nucleic acid sequence of about 600 bp by repeating cycles each consisting of denaturation for 5 seconds and annealing/extension for 8 seconds, while the PCR is monitored using an intercalating dye or the like to compare the number of reaction cycles performed until the time when the amount of amplified product exceeds a certain level with that of the case of using the wild-type DNA polymerase.

2. Definitions, Etc.

The "DNA polymerase" as referred to in the present invention, unless otherwise specified, means a protein having the activity of extending a complementary DNA strand to a template nucleic acid (DNA or RNA) using dideoxyribonucleoside triphosphate as a substrate. The "Taq polymerase" or "Taq DNA polymerase" as referred to in this invention, unless otherwise specified, means a DNA polymerase derived from *Thermus aquaticus*. The amino acid sequence of this DNA polymerase and the nucleotide sequence encoding the same are respectively shown in SEQ ID NOs: 8 and 7 in the Sequence Listing which constitutes a part of the present specification.

When the term "amino acid corresponding to position X" is used to in this invention in connection with a mutant, unless otherwise specified, it is intended that "X" represents an amino acid residue number starting from the N-terminal side of the originating wild-type amino acid sequence, i.e., the amino acid sequence of the wild-type Taq polymerase according to SEQ ID NO: 8, and that the "amino acid corresponding to" position X, when the amino acid sequence of the wild-type Taq polymerase according to SEQ ID NO: 8 and the amino acid sequence of a homologue (including a mutant) thereof are aligned, means an amino acid residue corresponding to the above-noted position X in the amino acid sequence of the homologue. In an exemplary case where a mutant lacks a segment consisting of 1-239 amino acids from the N terminus, the "amino acid corresponding to position 651" in a nucleotide means the amino acid at position 412 of its mutant. Such significance is obvious to those skilled in the art.

The "activity" as referred to in the present invention in connection with a DNA polymerase, unless otherwise specified, includes DNA synthesis activity and primer extension activity. The DNA synthesis activity includes the activity of synthesizing a DNA complementary to a DNA used as a template, and the activity of synthesizing a DNA complementary to a RNA used as a template. As known to those skilled in the art, the DNA synthesis activity can be determined as the activity of incorporating deoxyribonucleoside triphosphate (dNTP) as a substrate. More specifically, a calf thymus DNA, a salmon sperm DNA, or the like is partially digested with DNase I to provide a nicked or gapped double-strand DNA as a template, and a radioisotope-labeled dNTP is mixed with a substrate dNTP; then, the DNA polymerase of interest is caused to act, so that the amount of nucleotides incorporated into nicks by nick translation or into gaps by primer extension activity can be determined using radioactivity as an indicator. This determination method, which is called nucleotide incorporation assay, is a standard method for determining DNA polymerase activity.

The "DNA synthesis activity" or "basic DNA polymerase activity" as referred to in the present invention, unless otherwise specified, means the activity of incorporating dNTP using DNA as a template. When the "DNA synthesis activity" or "basic DNA polymerase activity" is represented by numerical value in this invention, unless otherwise specified, the amount of enzyme, i.e., DNA polymerase, required to incorporate 10 nmol of nucleotides at 72° C. for 30 minutes is defined as 1 unit (U), and such activity is expressed as a value for specific activity (activity per protein amount) in U/mg or the like. Unless otherwise specified, the conditions for this determination are set as disclosed in the Examples section of the present application.

The "reverse transcription activity" as referred to in the present invention, unless otherwise specified, means the activity of incorporating dNTP using RNA as a template. When the "reverse transcription activity" is represented by numerical value in this invention, unless otherwise specified, the amount of enzyme, i.e., DNA polymerase, required to incorporate 10 nmols of nucleotide at 72° C. for 30 minutes is defined as 1 unit (U), and such activity is expressed as a value for specific activity (activity per protein amount) in U/mg or the like. Unless otherwise specified, the conditions for this determination are set as disclosed in the Examples section of the present application.

The "primer extension activity" as referred to in the present invention, unless otherwise specified, means the length of strand extended per unit time when a DNA polymerase of interest is caused to act on a substrate dNTP using DNA or RNA as a template, and the length can be expressed in kb/U/min, bp/pmol/min, or the like. Unless otherwise specified, the conditions for this determination are set as disclosed in the Examples section of the present application.

When the phrase "substituting, deleting, inserting and/or adding one to nine amino acid residues" is used in the present invention, the number of amino acids to be substituted or otherwise modified is not particularly limited as long as the protein (DNA polymerase) having the modified amino acid sequence has a desired function, and 1-9 or about 1-4 amino acids may be substituted or otherwise modified, or even more amino acids may be substituted or otherwise modified if said substitution or the like is intended to encode the same or similar amino acid sequence. Means for obtaining a protein having such an amino acid sequence are well known to those skilled in the art.

The substitution or the like of amino acid residue may also be substitution or like that does not cause an electrostatic change, for example, substitution by an amino acid residues that is similar in electric charge and/or polarity. Examples of such a substitution include substitution between amino acid residues having such an aliphatic side chain that the side chain (also expressed as "R group") is non-polar around physiological pH (7.0) (e.g., glycine residues, alanine residues, valine residues, leucine residues, isoleucine residues, and proline residues), substitution between amino acids having a polar uncharged side chain (e.g., serine residues, threonine residues, cysteine residues, methionine residues, asparagine residues, and glutamine residues), substitution between amino acid residues having a side chain that is positively charged around physiological pH (e.g., lysine residues, arginine residues, and histidine residues), substitution between amino acid residues having a negatively charged side chain (e.g., asparatic acid residues, glutamic acid residues), substitution between polar amino acid residues, and substitution between non-polar amino acid residues.

The term "under stringent conditions" as used in the present invention, unless otherwise specified, means moderately or highly stringent conditions.

The moderately stringent conditions can be easily designed by those skilled in the art, typically on the basis of the length of a polynucleotide of interest. The basic conditions are described in Sambrook, et al., *Molecular Cloning: A Laboratory Manual*, 3rd Edition, Chapters 6-7, Cold Spring Harbor Laboratory Press, 2001. A typical example of the moderately stringent conditions comprises: the pre-washing conditions of 5×SSC, 0.5% SDS, 1.0 mM EDTA (pH 8.0) for a nitrocellulose filter; the hybridization conditions of about 50% formamide, 2-6×SSC at about 40-50° C. (or those conditions for other similar hybridization solutions such as Stark's solution in about 50% formamide at about 42° C.); and the washing conditions of 0.5-6×SSC, 0.1% SDS at about 40° C.-60° C. The moderately stringent conditions preferably comprise the hybridization conditions of 6×SSC at about 50° C., and may also comprise the above-mentioned pre-washing conditions and/or washing conditions.

The highly stringent conditions can also be easily designed by those skilled in the art, typically on the basis of the length of a polynucleotide of interest The highly stringent conditions comprise a higher temperature and/or a lower salt concentration than the moderately stringent conditions. The highly stringent conditions typically comprise the hybridization conditions of 0.2-6×SSC, preferably 6×SSC, more preferably 2×SSC, and still more preferably 0.2×SSC at about 65° C. In any case, the highly stringent conditions preferably comprise the washing conditions of 0.2×SSC, 0.1% SDS at about 65-68° C.

In any case, SSPE (1×SSPE=0.15 M NaCl, 10 mM NaH$_2$PO$_4$, and 1.25 mM EDTA, pH 7.4) can be used in place of SSC (1×SSC=0.15 M NaCl and 15 mM sodium citrate) as a buffer for hybridization, pre-washing and washing. In any case, washing can be performed for about 15 minutes after completion of hybridization.

When hybridization is performed under stringent conditions for the purpose of the present invention, use can be made of a commercially available hybridization kit that does not use a radioactive substance as a probe, for example, ECL direct labeling & detection system (Amersham). When such a kit is used, stringent hybridization can typically be performed as follows: a blocking reagent and NaCl are added to a hybridization buffer in the kit so as to give concentrations of 5% (w/v) and 0.5 M, respectively, and hybridization is performed at 42° C. for 4 hours and is followed by washing twice in 0.4% SDS and 0.5×SSC at 55° C. for 20 minutes and then washing once in 2×SSC at room temperature for 5 minutes.

The high identity as referred to in the present invention in connection with an amino acid sequence, unless otherwise specified, means a sequence identity of at least 80%, preferably at least 90%, more preferably at least 95%, still more preferably at least 96%, and most preferably at least 97%. The high identity as referred to in the present invention in connection with a nucleotide sequence, unless otherwise specified, also means a sequence identity of at least 80%, preferably at least 90%, more preferably at least 95%, still more preferably at least 96%, and most preferably 97%. Search and analysis of polynucleotide or amino acid sequence identity can be made using an algorithm or program well known to those skilled in the art (e.g., BLASTN, BLASTP, BLASTX, ClustalW). When the program is used, parameters can be appropriately set by those skilled in the art, or the default parameters of each program may also be used. Specific procedures for such analyses are also well known to those skilled in the art.

Of both amino acid and nucleotide sequences, an important site for performance of an intended function is described in the present specification. Accordingly, those skilled in the art can design, prepare and use different mutants in which the sequences of other segments than such an important site are modified as appropriate. Such mutants can also fall within the scope of the present invention.

The "thermophilic eubacteria" as referred to in the present specification means eubacteria having an optimum growth temperature of at least 45° C. or at least 60° C. The thermophilic eubacteria can be exemplified by bacteria of the genus *Thermus*, such as *Thermus aquaticus* and *Thermus thermophilus*, those of the genus *Thermotoga*, such as *Thermotoga maritima*, those of the genus *Aquifex*, such as *Aquifex aeolicus*, and those of the genus *Thermodesulfobacterium*, such as *Thermodesulfobacterium commune*.

The "rapid PCR" as referred to in the present specification means PCR performed through cycles under such conditions that it takes no longer than one minute, preferably no longer than 30 seconds, and more preferably no longer than 10 seconds to complete one cycle consisting of denaturation, annealing, and extension steps, or one cycle consisting of denaturation and annealing/extension steps. Among commercially available PCR systems, those which can be used for rapid PCR are exemplified by SmartCycler® manufactured by Chephid, and CFX96 Touch Real-Time PCR Detection System manufactured by Bio-Rad.

3. Preparation Methods, Applications, Etc.

The DNA polymerases of the present invention can be prepared by a method well known to those skilled in the art. In order to construct a recombinant vector, it is advisable to prepare as a first step a DNA fragment of an appropriate length which contains the coding region of a protein of interest. In the nucleotide sequence of the coding region of the protein of interest, nucleotides may be so substituted as to give optimal codons for expression in host cells. Next, the prepared DNA fragment is inserted downstream of a promoter in an appropriate expression vector to construct a recombinant vector. It is necessary that said DNA fragment be incorporated into the vector so as to perform its function. The vector may contain not only promoters but also cis elements such as enhancers, splicing signals, polyadenylation signals, selective markers (e.g., dihydrofolate reductase gene, ampicillin resistance gene, neomycin resistance gene), ribosome binding sequences (SD sequences), and/or the like. A transformant capable of producing a protein of interest can be obtained by introducing a recombinant vector into an appropriate host cell.

The expression vector is not particularly limited as long as it is capable of autonomous replication in a host cell, and examples of the vector that can be used include plasmid vectors, phage vectors, and viral vectors. Examples of the plasmid vectors that can be used include *E. coli*-derived plasmids (e.g., pRSET, pBR322, pBR325, pUC118, pUC119, pUC18, and pUC19), *Bacillus subtilis*-derived plasmids (e.g., pUB110 and pTP5), and yeast-derived plasmids (e.g., YEp13, YEp24, and YCp50). Examples of the phage vectors that can be used include λ phages (e.g., Charon4A, Charon21A, EMBL3, EMBL4, λgt10, λgt11, and λZAP). Examples of the viral vectors that can be used include animal viruses such as retroviruses and vaccinia viruses, and insect viruses such as baculoviruses.

As the host cell, use can be made of any of prokaryocytes, yeasts, animal cells, insect cells, plant cells, and other cells, as long as the cell is capable of expressing a DNA encoding a protein of interest. The transformant as referred to in the present invention can be any of these cells.

When a bacterium is used as a host cell, examples of the bacterium that can be used as a host cell include bacteria of the genus *Escherichia*, such as *Escherichia coli*, those of the genus *Bacillus*, such as *Bacillus subtilis*, those of the genus *Pseudomonas*, such as *Pseudomonas putida*, and those of the genus *Rhizobium*, such as *Rhizobium meliloti*. Specific examples of the bacterium that can be used as a host cell include *Escherichia coli* such as *Escherichia coli* BL21, *Echerichia coli* XL1-Blue, *Escherichia coli* XL2-Blue, *Escherichia coli* DH1, *Escherichia coli* K12, *Escherichia coli* JM109, and *Escherichia coli* HB101, and *Bacillus subtilis* such as *Bacillus subtilis* MI 114, and *Bacillus subtilis* 207-21. The promoter used in this case is not particularly limited as long as it is capable of expression in a bacterium such as *E. coli*, and examples of the promoter that can be use include those derived from *E. coli*, phages and the like, such as trp promoter, lac promoter, $P_L$ promoter, and $P_R$ promoter. Artificially designed and modified promoters such as tac promoter, lacT7 promoter, and let I promoter can also be used. When a yeast is used as a host cell, examples of the yeast that can be used as a host cell include *Saccharomyces cerevisiae*, *Schizosaccharomyces pombe*, and *Pichia pastoris*. The promoter used in this case is not particularly limited as long as it is capable of expression in a yeast, and examples of the promoter that can be use include gall promoter, gal 10 promoter, heat shock protein promoter, MFα1 promoter, PHO5 promoter, PGK promoter, GAP promoter, ADH promoter, and AOX1 promoter. When an insect cell is used as a host cell, examples of the insect cell that can be used as a host cell include *Spodoptera frugiperda* ovarian cells, *Trichoplusia ni* ovarian cells, and cultured cells derived from silkworm ovaries. Examples of the *Spodoptera frugiperda* ovarian cells that can be used include Sf9 and Sf21; examples of the *Trichoplusia ni* ovarian cells that can be used include High 5 and BTI-TN-5B1-4 (Invitrogen); and examples of the cultured cells derived from silkworm ovaries that can be used include *Bombyx mori* N4.

The method for introducing a recombinant vector into a host is not particularly limited, as long as the method can introduce DNA into the host, and examples of the method that can be used include a calcium ion method, electroporation, a spheroplast method, and a lithium acetate method. The method for introducing a recombinant vector into an insect cell is not particularly limited, as long as the method can introduce DNA into the insect cell, and examples of the method that can be used include a calcium phosphate method, lipofection, and electroporation.

A transformant having introduced therein a recombinant vector incorporating a DNA encoding a protein of interest is cultured. Culturing of the transformant can be carried out according to a conventional method used for culture of host cells.

The protein of interest can be obtained by collecting it from the culture of the transformant. The "culture" as referred to herein encompasses all of culture supernatants, cultured cells, cultured microorganisms, and disrupted products of cells or microorganisms. In order to produce the protein of interest, use may be made of not only cultured systems but also animal individuals, plant individual, silkworms, and the like.

In the case where the protein of interest is accumulated in transformant cells, the culture is centrifuged to collect the cells from the culture, and the collected cells are washed and disrupted to extract the protein of interest. In the case where the protein of interest is excreted outside the transformant cells, the culture supernatant is used as it is, or cells or microorganisms are removed from the culture supernatant by centrifugation or the like. The resulting protein can be purified by solvent extraction, salting-out/desalting with ammonium sulfate or the like, precipitation with an organic solvent, diethylaminoethyl (DEAE)-sepharose, ion exchange chromatography, hydrophobic chromatography, gel filtration, affinity chromatography, or the like.

The mutants of the present invention, which can be prepared as described above, are particularly useful in RT-PCR using RNA as a template. The inventive mutants which are superior in both basic DNA polymerase activity and reverse transcription activity display the advantage that both reverse transcription reaction and PCR can be performed using the same enzyme. Furthermore, the inventive mutants which have an improved reaction rate as compared with the wild type are useful in rapid PCR.

The mutants of the present invention can be used as a component of a nucleic acid amplification (particularly, PCR) kit. In addition to any of the inventive mutants, the DNA amplification (particularly, PCR) kit can contain reagents (e.g., four types of dNTPs, $Mg^{2+}$, buffer, additives), a vessel, an apparatus, and the like which are necessary for nucleic acid amplification. Such a kit is suitable for a variety of applications, including nucleic acid sequencing, gene diagnosis, individual identification, variety identification, SNP (single nucleotide polymorphism) analysis for constitutional study, and archaeological excavation.

EXAMPLES

Example 1

Construction of Mutants

1. Introduction of Mutations:

In order to construct each of amino acid substitution mutants of a Taq polymerase, a site-specific mutation was introduced in a primer dependent manner by PCR using a primer having a sequence designed such that a mutation(s) is(are) inserted at a position(s) of interest, with an expression plasmid having a Taq polymerase gene inserted therein being used as a template. The introduction of a site-specific mutation into a Taq polymerase was performed using any of the primers shown below. The amino acid substitution sites for the respective mutant constructions are underlined.

[Formula 1]
Exo⁻
Taq117119A-F
(SEQ ID NO: 1)
CTCGAGGTCCCGGGCTACGCGGCGGCCGACGTCCTGGCCAGCCTG Taq117119A-R
(SEQ ID NO: 2)
CAGGCTGGCCAGGACGTCGGCCGCCGCGTAGCCCGGGACCTCGAG Taq142144A-F
(SEQ ID NO: 3)
GTCCGCATCCTCACCGCCGCCAAAGCCCTTTACCAGCTCCTTTCC Taq142144A-R
(SEQ ID NO: 4)
GGAAAGGAGCTGGTAAAGGGCTTTGGCGGCGGTGAGGATGCGGAC

[Formula 2]
Exo⁻ + 9aa
Taq117119A-F
(SEQ ID NO: 1)
CTCGAGGTCCCGGGCTACGCGGCGGCCGACGTCCTGGCCAGCCTG Taq117119A-R
(SEQ ID NO: 2)
CAGGCTGGCCAGGACGTCGGCCGCCGCGTAGCCCGGGACCTCGAG Taq142144A-F
(SEQ ID NO: 3)
GTCCGCATCCTCACCGCCGCCAAAGCCCTTTACCAGCTCCTTTCC Taq142144A-R
(SEQ ID NO: 4)
GGAAAGGAGCTGGTAAAGGGCTTTGGCGGCGGTGAGGATGCGGAC Taq-9AAin-F R2
(SEQ ID NO: 7)
CAGACCTAGAGGCCCGGGGCCCGCGCCGGGCGCCGCGTCGTCTGGTGAA
GAGCGTGCGGGAG Taq-9AAin-R R2
(SEQ ID NO: 8)
CTCCCGCACGCTCTTCACCAGACGACGCGGCGCCCGGCGCGGGCCCCGG
GCCTCTAGGTCTG Fifty microliters of a PCR reaction mixture (20 ng of pTV-Taq plasmid DNA, 0.5 µM each primer set, 0.2 mM dNTP, and 1 U of Pyrobest DNA polymerase (Takara Bio)) was subjected to initial denaturation in a Pyrobest buffer at 98° C. for 10 seconds, which was followed by PCR under the conditions of 16 cycles (98° C. for 10 seconds, 55° C. for 30 seconds, and 72° C. for 8 minutes). 5 U of the restriction enzyme DpnI was added to the resulting PCR product, and the mixture was incubated at 37° C. for 2 hours. Then, the reaction mixture was introduced into the E. coli JM109 strain, and the resulting strain was cultured. By using the procedure described in the next section, a plasmid was extracted from the resulting transformant clone, and then it was confirmed that the mutation(s) was(were) introduced into the position(s) of interest.

2. Preparation of Plasmids and Confirmation of Nucleotide Sequences:

With a drug resistance gene in the plasmid being used as a marker, selection was made of an E. coli transformant that was seeded onto an LB plate medium containing 50 µg/mL of ampicillin and cultured at 37° C. for 15 hours. The colony that has grown was inoculated into 4 mL of an LB liquid medium containing 50 g/mL of ampicillin and cultured at 37° C. for 15 hours. A plasmid was extracted from the harvested microorganisms using a QIAprep Spin Miniprep Kit (QIAGEN) according to the kit's protocol. With the DNA of the resulting plasmid being used as a template, dideoxy reaction was performed using a DITCS Quick Start Master Mix (Beckman Coulter), so that the nucleotide sequence was confirmed using a multi-capillary DNA analysis system CEQ2000XL (BECKMAN COULTER).

The novel DNA polymerases constructed in the present study are listed in the following table.

TABLE 1

| DNA Polymerase | number of amino acids | Theoretical pI | Mw. | characteristics |
|---|---|---|---|---|
| Taq WT (SEQ ID NO: 8) | 832 | 6.04 | 93910.1 | Taq Pol wild type |
| 9aa-insertion | 841 | 6.16 | 94843.2 | insertion (737-G P G Q A P R A L) (SEQ ID NO: 15) |
| Exo⁻ WT (SEQ ID NO: 10) | 832 | 6.31 | 93720.0 | E117A, D119A, D142A, D144A |
| Taq 9aa (SEQ ID NO: 12) | 841 | 6.31 | 94970.4 | insertion (737-G P R R A P R A L) (SEQ ID NO: 16) |
| Taq 9aa+ Taq8 E742A | 841 | 6.23 | 94785.2 | insertion (737-G P G Q A P R A L), E742A |
| Exo⁻ +9aa (SEQ ID NO: 14) | 841 | 6.71 | 94785.2 | Exo⁻ WT + insertion (737-G P R R A P R A L) |

3. Expression and Purification of DNA Polymerases:

Production of each of wild-type and mutant Taq polymerases was performed under the following conditions: the JM109 strain was transformed by a standard method using a plasmid that incorporated the gene of each polymerase into the pTV-118N vector, and the resulting transformant was cultured in 500 ml of an LB liquid medium containing 50 µg/mL of ampicillin at 37° C. for 24 hours.

Then, the culture was centrifuged at 6,000 rpm for 15 minutes to harvest microorganisms, and the harvested microorganisms were suspended in 25 mL of Buffer A (50 mM Tris-HCl (pH 8.0), 0.1 mM EDTA, 0.5 mM DTT, 10% glycerol) supplemented with 1 mM PMSF, and were subjected to ultrasonication and centrifuged at 14,500 rpm for 15 minutes to obtain a crude cell extract. The crude extract was left to stand at 80° C. for 20-30 minutes to denature a non-thermostable protein, and was centrifuged at 14,500 rpm for 15 minutes to obtain a thermostable fraction in the supernatant. Polyethyleneimine was added to the fraction on ice so as to give a concentration of 0.15%, and the precipitate (nucleic acid) was removed by centrifugation at 14,500 rpm for 15 minutes.

Next, ammonium sulfate was added to the supernatant on ice so as to give 80% saturation, and the suspension was stirred for at least 1 hour to effect salting-out. The suspension was centrifuged at 14,500 rpm for 15 minutes to effect protein precipitation, and the precipitate was suspended in Buffer A supplemented with 0.8 M ammonium sulfate; thereafter, the suspension was subjected to chromatography by passing it through a Hi Trap Phenyl column (5 mL) using an ÄKTA Explorer (GE Healthcare). After passage of the sample, a gradient from 1 M to 0 M ammonium sulfate was created and ultrapure water was passed through the column to thereby elute an enzyme of interest. The fraction was recovered and passed through a Hi Trap Heparin column (1 mL). Elution was performed with a gradient from 0 M to 800 mM sodium chloride as dissolved in Buffer A. The enzymes of interest thus obtained were each analyzed by SDS-PAGE to confirm their purity.

Example 2

Evaluation of Mutants

1. DNA Synthesis Activity:

In order to determine the basic DNA polymerase activity of each of the purified enzymes, a world-wide standard method was used. More specifically, the intensity of the activity of incorporating deoxyribonucleotides on a DNA template strand was determined, and the activity per unit protein amount was calculated in units. To perform a nucleotide incorporation reaction, a reaction mixture was prepared by adding 0.2 mg/mL of activated DNA (obtained by treating a calf thymus DNA with DNase I to partially nick or gap a double-strand DNA), 0.2 mM dNTP, 440 nM [$^3$H]-dTTP, 50 mM Tris-HCl (pH 8.0), 1.5 mM $MgCl_2$, 50 mM KCl, 0.1% TritonX-100, 100 μg/mL of BSA, and 1 nM DNA polymerase, and the mixture was reacted at 72° C.; then, 10 μL of the mixture was spotted onto DE81 paper.

After air-dried for 10 minutes, the paper was washed with an aqueous 5% disodium hydrogenphosphate solution to remove unreacted nucleotides. The washing was repeated three times, each for 10 minutes. After the DE81 paper was dried, radiation was measured by a liquid scintillation counter, whereby the amount of [$^3$H]-dTMP incorporated into the activated DNA due to the DNA polymerase activity was calculated to determine enzyme activity (in unit). One unit is defined as the amount of enzyme, i.e., DNA polymerase, required to incorporate 10 nmol of nucleotides at 72° C. for 30 minutes. The specific activity was calculated for each enzyme.

2. Extension Activity (Extension Rate):

Primer extension activity per unit was determined based on each of the calculated specific activity values. The primer extension reaction was performed using a substrate (primed DNA) obtained by annealing a $^{32}$P-radiolabeled oligonucleotide to an M13 phage single-strand DNA (7 kb). After 10 μL of a reaction mixture (5 nM M13 primed DNA, 0.2 mM dNTP, 50 mM Tris-HCl (pH 8.0), 1.5 mM MgCl, 50 mM KCl, 0.1% TritonX-100, and 100 μg/mL BSA) was reacted at 72° C. for 5 minutes, the reaction was terminated by adding 2.5 μL of 6× loading buffer (300 nM NaOH, 6 mM EDTA, 18% Ficol 400, 0.15% BCG, and 0.25%×C). The reaction product was separated by agarose gel electrophoresis (agarose gel was prepared at a concentration of 1% in 50 mM NaOH and 1 mM EDTA) under alkaline conditions, and after the electrophoresis, the product was detected by autoradiography (using an image analyzer (FLA-5000, Fujifilm)).

The strand length of the reaction product was determined from the obtained image by comparing it with a size marker, whereby the strand length of the synthetic product obtained per unit time (1 min) was calculated. As a result, whereas the wild-type Taq polymerase had an extension rate of 3.89 kb/min, the mutant Exo⁻ whose 5'-3' exonuclease activity residues were substituted in a site-specific manner had a rate of 9.17 kb/min. Exo⁻+9aa having nine amino acids inserted therein had a rate of 11.3 kb/min.

3. Reverse Transcription Activity:

The intensity of the activity of incorporating deoxyribonucleotides on a RNA template strand was determined for each of the purified DNA polymerases. The reaction was performed by the following procedure. Each of the DNA polymerases was added to a solution containing 20 ng/μL of poly(rA)•p(dT), 10 μM dTTP, 440 nM [$^3$H]-dTTP, 50 mM Tris-HCl (pH 8.0), 1 mM $MnCl_2$, 50 mM KCl, 0.1% TritonX-100, and 100 μg/ml, of BSA, and the mixture was reacted at 60° C. for 10 minutes; then, 10 μL of the mixture was spotted onto DE81 paper. After air-dried for 10 minutes, the paper was washed with an aqueous 5% disodium hydrogenphosphate solution to remove unreacted nucleotides. The washing was repeated three times, each for 10 minutes.

After the DE81 paper was dried, radiation was measured by a liquid scintillation counter, whereby the amount of [$^3$H]-dTMP incorporated into the poly(rA)•p(dT) due to the DNA polymerase activity was calculated to determine enzyme activity (in unit). One unit is defined as the amount of enzyme, i.e., DNA polymerase, required to incorporate 10 nmol of nucleotides at 72° C. for 30 minutes. The specific activity was calculated for each enzyme.

It was revealed that the wild-type Taq DNA polymerase purified by the present inventors showed a reverse transcription activity of 4.24×10 U/mg.

The reverse transcription activity of the mutant constructed according to the present invention was determined using the same conditions on the basis of its nucleotide incorporation activity and, as a result, Taq 9aa showed a reverse transcription activity of 2.78×10 U/mg. This result means that the reverse transcription activity of Taq 9aa was 0.66 times that of the wild-type Taq DNA polymerase which is taken as 1.

The properties of the mutant Taq polymerases are summarized in the following table.

TABLE 2

| DNA Polymerase | Purified Protein from 500 mL culture (mg) | DNA-DNA Specific Activity (×10⁵ U/mg) | DNA-DNA Relative activity (%) | RNA-DNA Specific Activity (×10³ U/mg) | RNA-DNA Relative activity (%) | Extension rate DNA (kb/U · min) | Extension rate RNA (bp/pmol · min) |
|---|---|---|---|---|---|---|---|
| Taq WT (SEQ ID NO: 8) | 1.65 | 5.11 | 100 | 4.24 | 27.5 | 3.89 | 14.0 |
| 9aa-insertion | 1.66 | 7.13 | 140 | | | 3.89 | |
| Exo-WT(SEQ ID NO: 10) | 0.54 | 3.79 | 74.2 | | | 9.17 | |
| Taq 9aa (SEQ ID NO: 12) | 1.02 | 5.14 | 101 | 2.78 | 18.2 | 5.98 | 246 |
| Taq 9aa+ Taq8 AA | 0.94 | 7.22 | 141 | | | 6.59 | |
| Exo- + 9aa (SEQ ID NO: 14) | 0.22 | 4.76 | 93.2 | | | 11.3 | |

Example 3

Evaluation of the Reaction Rates of the Mutants

First, cDNA was synthesized with PrimeScript® RT Reagent Kit (Perfect Real Time) (Takara Bio) using 500 ng of Human HL60 Cell Total RNA as a template.

The reaction rate of Taq 9aa prepared in Example 1 was evaluated by real-time PCR that used a 10 ng RNA equivalent of the obtained cDNA as a template and that targeted 186 bp, 381 bp, and 533 bp beta-actin cDNA regions. The primer pair used for amplifying the 186 bp beta-actin cDNA region consisted of primers having the nucleotide sequences of SEQ ID NOs: 17 and 18, respectively, in the Sequence Listing. The primer pair used for amplifying the 381 bp beta-actin cDNA region consisted of primers having the nucleotide sequences of SEQ ID NOs: 17 and 19, respectively, in the Sequence Listing. The primer pair used for amplifying the 533 bp beta-actin cDNA region consisted of primers having the nucleotide sequences of SEQ ID NOs: 17 and 20, respectively, in the Sequence Listing.

A total of three types of 25 μL PCR reaction mixtures were prepared on ice, each of which contained a 10 ng RNA equivalent cDNA, 0.4 μM each primers, 1×PCR Buffer [prepared using 10×PCR Buffer supplied with TaKaRa Taq (Takara Bio)], 0.2 mM each dNTPs, 0.3×SYBR Green I (Invitrogen), and 1.25 U of Taq 9aa. Also, a total of three types of control reaction mixtures were prepared on ice, each of which contained the same components except that 1.25 U of TaKaRa Taq DNA polymerase (Takara Bio) was contained in place of 1.25 UL of Taq 9aa. Next, these PCR reaction solutions were subjected to initial denaturation at 95° C. for 30 seconds, which was followed by real-time PCR for 40 cycles each consisting of 95° C. for 5 seconds and 60° C. for 10 seconds. After completion of the real-time PCR, melting curve analysis was made to confirm the specificity in amplification reaction. Additionally speaking, the reaction system used to perform the above-mentioned real-time PCRs was Thermal Cycler Dice® Real Time System (Takara Bio).

The monitoring results and melting curve analysis results for the amplified products in the reaction mixtures are shown in FIG. 9. The Ct values calculated via real-time PCRs with the reaction mixtures are listed in Table 3.

TABLE 3

| DNA Polymerase | 186 bp | 381 bp | 533 bp |
|---|---|---|---|
| TaKaRa Taq | 18.63 | Non-specifically amplified | Non-specifically amplified |
| Taq 9aa | 18.95 | 18.07 | 18.49 |

As a result, in the case of using TaKaRa Taq DNA Polymerase, the PCRs targeting 381 bp and 533 bp sequences yielded amplified products having shorter strands than the target sequences, presumably non-specific primer dimers, while in the case of using Taq 9aa, even the PCRs targeting 381 bp and 533 bp sequences yielded specifically amplified products having the target sequences. In the case of using Taq 9aa, the Ct values calculated via the real-time PCRs targeting 381 bp and 533 bp sequences were comparable to that calculated via the real-time PCR targeting a 186 bp sequence. This indicates that Taq 9aa has a higher reaction rate (polymerase synthesis rate) than the wild-type Taq DNA Polymerase.

Example 4

Construction and Evaluation of Taq 9aa and Taq Exo⁻+9aa

Protein expression and purification were repeated several times using Taq 9aa and Taq Exo⁻+9aa by the same procedure as in section 3 under Example 1. The resulting purified enzymes were identified by production lot and respectively designated as Taq 9aa 1st lot, Taq 9aa 2nd lot, Taq 9aa 3rd lot, and Taq Exo⁻+9aa 1st lot. The purified enzymes were subjected to electrophoresis with a 15% SDS polyacrylamide gel and stained with CBB. The results are shown in FIG. 10. The results indicate that in some production lots of Taq 9aa and Taq Exo⁻+9aa, peptide linkages were cleaved so that two types of fragments (middle and small units) which were different from full-length polypeptide fragments (large units) were detected by SDS PAGE (lane Nos. 4, 5, 6, 7, 8 and 9).

Example 5

Evaluation of the Reaction Rates of the Purified Enzymes Obtained in Example 4

Among the purified enzymes obtained in Example 4, Taq 9aa 1st lot having a high proportion of large units and Taq 9aa 3rd lot having a low proportion of large units were compared with each other in terms of reaction rate. The reaction rate comparison was made by the same procedure as in Example 3, except that 1.25 U of Taq 9aa 1st lot or 1.25 U of Taq 9aa 3rd lot was used in place of 1.25 U of Taq 9aa prepared in Example 1, and that the only reaction mixtures prepared were those used for the PCR targeting a 533 bp beta-actin cDNA region.

The monitoring results and melting curve analysis results for the amplified products in the reaction mixtures are shown in FIG. 11. The Ct values calculated via real-time PCRs with the reaction mixtures are listed in Table 4.

TABLE 4

| DNA Polymerase | 533 bp |
|---|---|
| TaKaRa Taq | 30.2 |
| Taq 9aa 1st lot | 17.7 |
| Taq 9aa 3rd lot | 18.1 |

The results showed that Taq 9aa 1 st lot having a high proportion of large units showed a lower Ct value than Taq 9aa 3rd lot having a low proportion of large units. This indicates that Taq 9aa with no peptide linkages cleaved had a higher reaction rate (polymerase synthesis rate) than Taq 9aa with peptide linkages partially cleaved.

Example 6

Analysis of Middle and Small Units

Middle and small units were separated from Taq 9aa 3rd lot constructed in Example 4, and the separated polypeptides were subjected to N-terminal amino acid sequence analysis. This analysis revealed that the amino acid sequence at the N termini of the middle units was MRGML (SEQ ID NO: 21) and that of the small units was RLVKS (SEQ ID NO: 22). Comparison of these sequences with the amino acid sequence of SEQ ID NO: 12 in the Sequence Listing showed that the N-terminal amino acid sequence of the middle units corresponds to the sequence at the N terminus of Taq 9aa, and that the N-terminal amino acid residue of the small units, i.e., arginine residue, corresponds to the arginine residue at position 743 of Taq 9aa. The results indicate that in Taq 9aa and Taq Exo⁻+9aa, the peptide linkage between the proline residue at position 742 and the arginine residue at position 743 from the N terminus may be cleaved in their preparation process.

Example 7

Construction of Taq 9aa R743X

There were constructed expression plasmids for Taq 9aa R743K, Taq 9aa R7431H, Taq 9aa R743E, Taq 9aa R743A, Taq 9aa R743Q, and Taq 9aa R743T modified by substituting R (arginine residue) at position 743 of the amino acid sequence (SEQ ID NO: 12) of Taq 9aa by K (lysine), H (histidine), E (glutamic acid), A (alanine), Q (glutamine), and T (threonine), respectively. SEQ ID NO: 24 in the Sequence Listing shows the amino acid sequence modified by substituting the arginine residue at position 743 of the amino acid sequence of Taq 9aa by a certain amino acid residue. The nucleotide sequence encoding the same is shown in SEQ ID NO: 23 in the Sequence Listing.

By using each of the thus-constructed expression plasmids, and the expression plasmid for Taq 9aa constructed in Example 1, the *E. coli* JM109 was transformed to effect protein expression. The *E. coli* JM109 transformant showing protein expression was harvested and subjected to ultrasonication; thereafter, the homogenate was heated at 70° C. for 20 minutes and then fractionated by centrifugation, so that a supernatant fraction was used as a crudely purified DNA polymerase solution.

Example 8

Evaluation of Taq 9aa R743X

The crudely purified DNA polymerase solutions obtained in Example 7 were subjected to electrophoresis with a 15% SDS polyacrylamide gel and stained with CBB (FIG. 12). The results showed that peptide linkage cleavage occurring in the process of polymerase preparation can be avoided by substituting the arginine residue at position 743 of Taq 9aa by an amino acid residue other than glutamic acid. Next, comparison between the DNA polymerases in terms of reaction rate were made using the crudely purified DNA polymerase solutions obtained in Example 7. The reaction rate comparison was made by the same procedure as in Example 5, except that 1.25 U of Taq 9aa R743X obtained in the above-mentioned manner was used in place of 1.25 U of Taq 9aa 3rd lot.

The monitoring results and melting curve analysis results for the amplified products are shown in FIG. 13. The Ct values calculated via real-time PCRs with the reaction mixtures are listed in Table 5.

TABLE 5

| DNA Polymerase | 533 bp |
|---|---|
| TaKaRa Taq | 25.5 |
| Taq 9aa R743K | 14.2 |
| Taq 9aa R743H | 14.8 |
| Taq 9aa R743E | 14.4 |
| Taq 9aa R743A | 21.8 |
| Taq 9aa R743Q | 14.7 |
| Taq 9aa R743T | 14.0 |
| Taq 9aa | 14.0 |

As shown in FIG. 13 and Table 5, the reactions using any of the mutants showed a lower Ct value than the reaction using the wild-type Taq DNA Polymerase.

Example 9

Rapid PCR Using Taq 9aa R743T and Taq Exo⁻+9aa R743T

1. Expression and Purification of Taq 9aa R743T and Taq Exo⁻+9aa R743T

There was constructed an expression plasmid for Taq Exo⁻+9aa R743T modified by substituting R (arginine residue) at position 743 of the amino acid sequence (SEQ ID NO: 14) of Taq Exo⁻+9aa by T (threonine). By using the thus-constructed expression plasmid and the expression plasmid for Taq 9aa R743T constructed in Example 7, protein expression and purification of Taq 9aa R743T and Taq Exo⁻+Taq 9aa R743T were performed by the same procedure as in section 3 under Example 1.

2. Evaluation of the Rapid PCRs Using Taq 9aa R743T and Taq Exo⁻+9aa R743T

First, cDNA was synthesized with PrimeScript® RT Reagent Kit (Perfect Real Time) (Takara Bio) using 500 ng of Human HL60 Cell Total RNA as a template. A total of four types of 25 µL reaction mixtures for the PCR targeting a 186 bp beta-actin region were prepared on ice, each of which contained a 10 ng RNA equivalent cDNA of the obtained cDNA, a 0.4 µM primer having the nucleotide sequence of SEQ ID NO: 17 in the Sequence Listing, a 0.4 µM primer having the nucleotide sequence of SEQ ID NO: 18 in the Sequence Listing, 1×PCR Buffer [prepared using 10×PCR Buffer supplied with TaKaRa Taq (Takara Bio)], 0.2 mM each dNTPs, 0.3×SYBR Green I (Invitrogen), and 1.25 U each of Taq 9aa R743T, Taq Exo⁻+9aa R743T, Taq 9aa 3rd lot, Taq Exo⁻+9aa 1st lot, or TaKaRa Taq DNA polymerase (Takara Bio). By using a CFX96 Touch™ Real-time PCR Detection System (Bio-Rad), these PCR reaction solutions were subjected to initial denaturation at 95° C. for 30 seconds, which was followed by PCR for 40 cycles each consisting of 95° C. for 5 seconds and 60° C. for 1 second. After completion of the real-time PCR, melting curve analysis was made to confirm the specificity in amplification reaction.

The monitoring results and melting curve analysis results for the amplified products are shown in FIGS. 14 and 16. The Ct values calculated via real-time PCRs with the reaction mixtures are listed in Table 6.

TABLE 6

| DNA Polymerase | 186 bp |
|---|---|
| TaKaRa Taq | Non-specifically amplified |
| Taq 9aa 3rd lot | Non-specifically amplified |
| Taq 9aa R743T | 17.90 |
| Taq Exo⁻ + 9aa 1st lot | 17.19 |
| Taq Exo⁻ + 9aa R743T | 16.54 |

As a result, the PCR using Taq 9aa yielded amplified products having a shorter strand than the target sequence, presumably non-specific primer dimers, while the PCR using Taq 9aa R743T yielded amplified products having the target sequence. This indicates that Taq 9aa R743T has a higher reaction rate (polymerase synthesis rate) than Taq 9aa. It was also found that Taq Exo⁻+9aa R743T showed a lower Ct value than Taq Exo⁻+9aa; this indicates that Taq Exo⁻+9aa R743T has a higher reaction rate (polymerase synthesis rate) than Taq Exo⁻+9aa.

SEQUENCE LISTING FREE TEXT

SEQ ID NO: 1 PCR primer Taq117119A-F
SEQ ID NO: 2 PCR primer Taq 117119A-R

SEQ ID NO: 3 PCR primer Taq 142144A-F
SEQ ID NO: 4 PCR primer Taq142144A-R
SEQ ID NO: 5 PCR primer Taq-9AAin-F R2
SEQ ID NO: 6 PCR primer Taq-9AAin-R R2
SEQ ID NO: 7 Taq WT nucleotide sequence
SEQ ID NO: 8 Taq WT amino acid sequence
SEQ ID NO: 9 Taq Exo nucleotide sequence
SEQ ID NO: 10 Taq Exo⁻ amino acid sequence
SEQ ID NO: 11 Taq 9aa nucleotide sequence
SEQ ID NO: 12 Taq 9aa amino acid sequence
SEQ ID NO: 13 Taq Exo⁻+9aa nucleotide sequence
SEQ ID NO: 14 Taq Exo⁻+9aa amino acid sequence
SEQ ID NO: 15 Insertion sequence
SEQ ID NO: 16 Insertion sequence
SEQ ID NO: 17 PCR primer hACTB-F
SEQ ID NO: 18 PCR primer hACTB-R186
SEQ ID NO: 19 PCR primer hACTB-R381
SEQ ID NO: 20 PCR primer hACTB-R533
SEQ ID NO: 21 N-terminal amino acid sequence of middle unit
SEQ ID NO: 22 N-terminal amino acid sequence of small unit
SEQ ID NO: 23 Taq 9aa R743X nucleotide sequence
SEQ ID NO: 24 Taq 9aa R743X amino acid sequence
SEQ ID NO: 25 Taq Exo⁻+9aa R743X nucleotide sequence
SEQ ID NO: 26 Taq Exo⁻+9aa R743X amino acid sequence

The invention claimed is:

1. A DNA polymerase which is any one of (a1) to (c1) mentioned below:
   (a1) a DNA polymerase comprising an amino acid sequence modified from the amino acid sequence of SEQ ID NO: 8 by inserting -$A_{737}$-$A_{738}$-$A_{739}$-$A_{740}$-$A_{741}$-$A_{742}$-$A_{743}$-$A_{744}$-$A_{745}$- between the amino acid residue at position 736 and the amino acid residue at position 737,
   wherein:
   $A_{737}$ is an amino acid residue having a non-polar aliphatic side chain;
   $A_{738}$ is an amino acid residue having a non-polar aliphatic side chain;
   $A_{739}$ is an amino acid residue having a positively charged side chain;
   $A_{740}$ is an amino acid residue having a positively charged side chain;
   $A_{741}$ is an amino acid residue having a non-polar aliphatic side chain;
   $A_{742}$ is an amino acid residue having a non-polar aliphatic side chain;
   $A_{743}$ is any given amino acid residue;
   $A_{744}$ is an amino acid residue having a positively charged side chain; and
   $A_{745}$ is an amino acid residue having a non-polar aliphatic side chain;
   (b1) a DNA polymerase comprising an amino acid sequence modified from the amino acid sequence of the DNA polymerase as recited in (a1), by substituting, deleting, inserting and/or adding one to nine amino acid residues which exclude the amino acid sequence inserted between an amino acid residue corresponding to position 736 and an amino acid residue corresponding to position 737; and
   (c1) a DNA polymerase comprising an amino acid sequence that is modified from an amino acid sequence of a Family A DNA polymerase derived from a thermophilic eubacterium, by inserting -$A_{737}$-$A_{738}$-$A_{739}$-$A_{740}$-$A_{741}$-$A_{742}$-$A_{743}$-$A_{744}$-$A_{745}$- between amino acid residues corresponding to the amino acid residues at positions 736 and 737 in the amino acid sequence of SEQ ID NO: 8, and which has at least 80% sequence identity to the amino acid sequence of the DNA polymerase as recited in (a1).

2. The DNA polymerase as recited in claim 1, wherein in the amino acid sequence -$A_{737}$-$A_{738}$-$A_{739}$-$A_{740}$-$A_{741}$-$A_{742}$-$A_{743}$-$A_{744}$-$A_{745}$- contained in the DNA polymerase of (a1):
   $A_{737}$ is a glycine residue;
   $A_{738}$ is a proline residue;
   $A_{739}$ is an arginine residue;
   $A_{740}$ is an arginine residue;
   $A_{741}$ is an alanine residue;
   $A_{742}$ is a proline residue;
   $A_{743}$ is any given amino acid residue;
   $A_{744}$ is an arginine residue; and
   $A_{745}$ is a leucine residue.

3. The DNA polymerase as recited in claim 1 or 2, wherein $A_{743}$ is an arginine residue, a lysine residue, a histidine residue, an alanine residue, a glutamine residue, a glutamic acid residue, or a threonine residue.

4. The DNA polymerase as recited in claim 1, wherein the DNA polymerase comprises the amino acid sequence of SEQ ID NO: 24.

5. A polynucleotide which is any one of (A1) to (D1) mentioned below:
(A1) a polynucleotide comprising the nucleotide sequence of SEQ ID NO: 23;
(B1) a polynucleotide comprising a nucleotide sequence encoding the DNA polymerase as recited in claim 1;
(C1) a polynucleotide that hybridizes under stringent conditions with a polynucleotide comprising a complementary sequence to the nucleotide sequence of the polynucleotide as recited in (A1), and which encodes a DNA polymerase, with (with the proviso that a segment inserted between an amino acid residue corresponding to position 736 and an amino acid residue corresponding to position 737 is the same, in terms of respective segmental elements, as the segment inserted between an amino acid residue corresponding to position 736 and an amino acid residue corresponding to position 737 in the DNA polymerase as recited in (a1) under claim 1; and
(D1) a polynucleotide that comprises a sequence at least 95% identical to the nucleotide sequence of the polynucleotide as recited in (A1), and which encodes a DNA polymerase, with the proviso that a segment inserted between an amino acid residue corresponding to position 736 and an amino acid residue corresponding to position 737 is the same, in terms of respective segmental elements, as the segment inserted between an amino acid residue corresponding to position 736 and an amino acid residue corresponding to position 737 in the DNA polymerase as recited in (a1) under claim 1.

6. A DNA polymerase which is any one of (a2) to (c2) mentioned below:
(a2) a DNA polymerase comprising an amino acid sequence modified from the amino acid sequence of SEQ ID NO: 8 by substituting at least one selected from the glutamic acid residue at position 117, the aspartic acid residue at position 119, the aspartic acid residue at position 142, and the aspartic acid residue at position 144 by an amino acid residue having a non-polar aliphatic side chain, and by inserting $-A_{737}-A_{738}-A_{739}-A_{740}-A_{741}-A_{742}-A_{743}-A_{744}-A_{745}-$ between the amino acid residue at position 736 and the amino acid residue at position 737,
wherein:
$A_{737}$ is an amino acid residue having a non-polar aliphatic side chain;
$A_{738}$ is an amino acid residue having a non-polar aliphatic side chain;
$A_{739}$ is an amino acid residue having a positively charged side chain;
$A_{740}$ is an amino acid residue having a positively charged side chain;
$A_{741}$ is an amino acid residue having a non-polar aliphatic side chain;
$A_{742}$ is an amino acid residue having a non-polar aliphatic side chain;
$A_{743}$ is any given amino acid residue;
$A_{744}$ is an amino acid residue having a positively charged side chain; and
$A_{745}$ is an amino acid residue having a non-polar aliphatic side chain;
(b2) a DNA polymerase comprising an amino acid sequence modified from the amino acid sequence of the DNA polymerase as recited in (a2), by substituting, deleting, inserting and/or adding one to nine amino acid residues which exclude amino acid residues corresponding to positions 117, 119, 142 and 144 and the segment inserted between the amino acid residue at position 736 and the amino acid residue at position 737; and
(c2) a DNA polymerase comprising a sequence that is at least 95% identical, and also identical in terms of the amino acid residues corresponding to positions 117, 119, 142 and 144 and the segment inserted between the amino acid residue at position 736 and the amino acid residue at position 737, to the amino acid sequence of the DNA polymerase as recited in (a2).

7. The DNA polymerase as recited in claim 6, wherein in the amino acid sequence $-A_{737}-A_{738}-A_{739}-A_{740}-A_{741}-A_{742}-A_{743}-A_{744}-A_{745}-$ contained in the DNA polymerase of (a2):
$A_{737}$ is a glycine residue;
$A_{738}$ is a proline residue;
$A_{739}$ is an arginine residue;
$A_{740}$ is an arginine residue;
$A_{741}$ is an alanine residue;
$A_{742}$ is a proline residue;
$A_{743}$ is any given amino acid residue;
$A_{744}$ is an arginine residue; and
$A_{745}$ is a leucine residue.

8. The DNA polymerase as recited in claim 6 or 7, wherein $A_{743}$ is an arginine residue, a lysine residue, a histidine residue, an alanine residue, a glutamine residue, a glutamic acid residue, or a threonine residue.

9. The DNA polymerase as recited in claim 6, wherein the DNA polymerase comprises the amino acid sequence of SEQ ID NO: 14.

10. A polynucleotide which is any one of (A2) to (D2) mentioned below:
(A2) a polynucleotide comprising the nucleotide sequence of SEQ ID NO: 13;
(B2) a polynucleotide comprising a nucleotide sequence encoding the DNA polymerase as recited in claim 6;
(C2) a polynucleotide that hybridizes under stringent conditions with a polynucleotide comprising a complementary sequence to the nucleotide sequence of the polynucleotide as recited in (A2), and which encodes a DNA polymerase, with the proviso that amino acid residues corresponding to positions 117, 119, 142 and 144 and a segment inserted between the amino acid residue at position 736 and the amino acid residue at position 737 are each the same as the amino acid residues corresponding to positions 117, 119, 142 and 144 and the segment inserted between the amino acid residue at position 736 and the amino acid residue at position 737 in the DNA polymerase as recited in (a1) under claim 6; and
(D2) a polynucleotide that comprises a sequence at least 95% identical to the nucleotide sequence of the polynucleotide as recited in (A2), and which encodes a DNA polymerase whose primer extension activity with DNA being used as a template is at least 4.00 kb/U·min, with the proviso that amino acid residues corresponding to positions 117, 119, 142 and 144 and a segment inserted between the amino acid residue at position 736 and the amino acid residue at position 737 are each the same as the amino acid residues corresponding to positions 117, 119, 142 and 144 and the segment inserted between the amino acid residue at position 736 and the amino acid residue at position 737 in the DNA polymerase as recited in (a2) under claim 6.

11. A recombinant vector comprising the polynucleotide as recited in claim 5 or 10.

12. A transformant comprising the recombinant vector as recited in claim 11.

13. A process for preparing the DNA polymerase as recited in claim 1, the process comprising a step of culturing a transformant which comprises a recombinant vector,
   wherein the recombinant vector is comprising a polynucleotide which is any one of (A1) to (D1) mentioned below:
   (A1) a polynucleotide comprising the nucleotide sequence of SEQ ID NO: 23;
   (B1) a polynucleotide comprising a nucleotide sequence encoding the DNA polymerase as recited in claim 1;
   (C1) a polynucleotide that hybridizes under stringent conditions with a polynucleotide comprising a complementary sequence to the nucleotide sequence of the polynucleotide as recited in (A1), and which encodes a DNA polymerase, with the proviso that a segment inserted between an amino acid residue corresponding to position 736 and an amino acid residue corresponding to position 737 is the same, in terms of respective segmental elements, as the segment inserted between an amino acid residue corresponding to position 736 and an amino acid residue corresponding to position 737 in the DNA polymerase as recited in (a1) under claim 1; and
   (D1) a polynucleotide that comprises a sequence at least 95% identical to the nucleotide sequence of the polynucleotide as recited in (A1), and which encodes a DNA polymerase, with the proviso that a segment inserted between an amino acid residue corresponding to position 736 and an amino acid residue corresponding to position 737 is the same, in terms of respective segmental elements, as the segment inserted between an amino acid residue corresponding to position 736 and an amino acid residue corresponding to position 737 in the DNA polymerase as recited in (a1) under claim 1.

14. A process for preparing the DNA polymerase as recited in claim 6, the process comprising a step of culturing a transformant which comprises a recombinant vector,
   wherein the recombinant vector is comprising a polynucleotide which is any one of (A2) to (D2) mentioned below:
   (A2) a polynucleotide comprising the nucleotide sequence of SEQ ID NO: 13;
   (B2) a polynucleotide comprising a nucleotide sequence encoding the DNA polymerase as recited in claim 6;
   (C2) a polynucleotide that hybridizes under stringent conditions with a polynucleotide comprising a complementary sequence to the nucleotide sequence of the polynucleotide as recited in (A2), and which encodes a DNA polymerase, with the proviso that amino acid residues corresponding to positions 117, 119, 142 and 144 and a segment inserted between the amino acid residue at position 736 and the amino acid residue at position 737 are each the same as the amino acid residues corresponding to positions 117, 119, 142 and 144 and the segment inserted between the amino acid residue at position 736 and the amino acid residue at position 737 in the DNA polymerase as recited in (a1) under claim 6; and
   (D2) a polynucleotide that comprises a sequence at least 95% identical to the nucleotide sequence of the polynucleotide as recited in (A2), and which encodes a DNA polymerase whose primer extension activity with DNA being used as a template is at least 4.00 kb/U·min, with the proviso that amino acid residues corresponding to positions 117, 119, 142 and 144 and a segment inserted between the amino acid residue at position 736 and the amino acid residue at position 737 are each the same as the amino acid residues corresponding to positions 117, 119, 142 and 144 and the segment inserted between the amino acid residue at position 736 and the amino acid residue at position 737 in the DNA polymerase as recited in (a2) under claim 6.

\* \* \* \* \*

```
                           SEQUENCE LISTING

<160> NUMBER OF SEQ ID NOS: 26

<210> SEQ ID NO 1
<211> LENGTH: 45
<212> TYPE: DNA
<213> ORGANISM: Artificial sequence
<220> FEATURE:
<223> OTHER INFORMATION: Taq117119A-F primer

<400> SEQUENCE: 1
ctcgaggtcc cgggctacgc ggcggccgac gtcctggcca gcctg          45

<210> SEQ ID NO 2
<211> LENGTH: 45
<212> TYPE: DNA
<213> ORGANISM: Artificial sequence
<220> FEATURE:
<223> OTHER INFORMATION: Taq117119A-R primer

<400> SEQUENCE: 2
caggctggcc aggacgtcgg ccgccgcgta gcccgggacc tcgag          45

<210> SEQ ID NO 3
<211> LENGTH: 45
<212> TYPE: DNA
<213> ORGANISM: Artificial sequence
<220> FEATURE:
<223> OTHER INFORMATION: Taq142144A-F primer

<400> SEQUENCE: 3
gtccgcatcc tcaccgccgc caaagcccct taccagctcc tttcc          45

<210> SEQ ID NO 4
<211> LENGTH: 45
<212> TYPE: DNA
<213> ORGANISM: Artificial sequence
<220> FEATURE:
<223> OTHER INFORMATION: Taq142144A-R primer

<400> SEQUENCE: 4
ggaaaggagc tggtaaaggg ctttggcggc ggtgaggatg cggac          45

<210> SEQ ID NO 5
<211> LENGTH: 62
<212> TYPE: DNA
<213> ORGANISM: Artificial sequence
<220> FEATURE:
<223> OTHER INFORMATION: Taq-9AAin-F R2 primer

<400> SEQUENCE: 5
cagacctaga ggcccggggc ccgcgccggg cgccgcgtcg tctggtgaag agcgtgcggg    60
```

-continued ag                                                                62

<210> SEQ ID NO 6
<211> LENGTH: 62
<212> TYPE: DNA
<213> ORGANISM: Artificial sequence
<220> FEATURE:
<223> OTHER INFORMATION: Taq-9AAin-R R2 primer

<400> SEQUENCE: 6
ctcccgcacg ctcttcacca gacgacgcgg cgcccggcgc gggccccggg cctctaggtc    60
tg                                                                62

<210> SEQ ID NO 7
<211> LENGTH: 2499
<212> TYPE: DNA
<213> ORGANISM: Thermus aquaticus
<220> FEATURE:
<221> NAME/KEY: CDS
<222> LOCATION: (1)..(2499)

<400> SEQUENCE: 7

```
atg agg ggg atg ctg ccc ctc ttt gag ccc aag ggc cgg gtc ctc ctg      48
Met Arg Gly Met Leu Pro Leu Phe Glu Pro Lys Gly Arg Val Leu Leu
1               5                   10                  15 gtg gac ggc cac cac ctg gcc tac cgc acc ttc cac gcc ctg aag ggc      96
Val Asp Gly His His Leu Ala Tyr Arg Thr Phe His Ala Leu Lys Gly
            20                  25                  30 ctc acc acc agc cgg ggg gag ccg gtg cag gcg gtc tac ggc ttc gcc     144
Leu Thr Thr Ser Arg Gly Glu Pro Val Gln Ala Val Tyr Gly Phe Ala
        35                  40                  45 aag agc ctc ctc aag gcc ctc aag gag gac ggg gac gcg gtg atc gtg     192
Lys Ser Leu Leu Lys Ala Leu Lys Glu Asp Gly Asp Ala Val Ile Val
    50                  55                  60 gtc ttt gac gcc aag gcc ccc tcc ttc gcc cac gag gcc tac ggg ggg     240
Val Phe Asp Ala Lys Ala Pro Ser Phe Arg His Glu Ala Tyr Gly Gly
65                  70                  75                  80 tac aag gcg ggc cgg gcc ccc acg ccg gag gac ttt ccc cgg caa ctc     288
Tyr Lys Ala Gly Arg Ala Pro Thr Pro Glu Asp Phe Pro Arg Gln Leu
                85                  90                  95 gcc ctc atc aag gag ctg gtg gac ctc ctg ggg ctg gcg cgc ctc gag     336
Ala Leu Ile Lys Glu Leu Val Asp Leu Leu Gly Leu Ala Arg Leu Glu
            100                 105                 110 gtc ccg ggc tac gag gcg gac gac gtc ctg gcc agc ctg gcc aag aag     384
Val Pro Gly Tyr Glu Ala Asp Asp Val Leu Ala Ser Leu Ala Lys Lys
        115                 120                 125 gcg gaa aag gag ggc tac gag gtc cgc atc ctc acc gcc gac aaa gac     432
Ala Glu Lys Glu Gly Tyr Glu Val Arg Ile Leu Thr Ala Asp Lys Asp
    130                 135                 140 ctt tac cag ctc ctt tcc gac cgc atc cac gtc ctc cac ccc gag ggg     480
Leu Tyr Gln Leu Leu Ser Asp Arg Ile His Val Leu His Pro Glu Gly
145                 150                 155                 160 tac ctc atc acc ccg gcc tgg ctt tgg gaa aag tac ggc ctg agg ccc     528
Tyr Leu Ile Thr Pro Ala Trp Leu Trp Glu Lys Tyr Gly Leu Arg Pro
                165                 170                 175 gac cag tgg gcc gac tac cgg gcc ctg acc ggg gac gag tcc gac aac     576
Asp Gln Trp Ala Asp Tyr Arg Ala Leu Thr Gly Asp Glu Ser Asp Asn
            180                 185                 190 ctt ccc ggg gtc aag ggc atc ggg gag aag acg gcg agg aag ctt ctg     624
Leu Pro Gly Val Lys Gly Ile Gly Glu Lys Thr Ala Arg Lys Leu Leu
        195                 200                 205
```

```
gag gag tgg ggg agc ctg gaa gcc ctc ctc aag aac ctg gac cgg ctg      672
Glu Glu Trp Gly Ser Leu Glu Ala Leu Leu Lys Asn Leu Asp Arg Leu
    210                 215                 220 aag ccc gcc atc cgg gag aag atc ctg gcc cac atg gac gat ctg aag      720
Lys Pro Ala Ile Arg Glu Lys Ile Leu Ala His Met Asp Asp Leu Lys
225                 230                 235                 240 ctc tcc tgg gac ctg gcc aag gtg cgc acc gac ctg ccc ctg gag gtg      768
Leu Ser Trp Asp Leu Ala Lys Val Arg Thr Asp Leu Pro Leu Glu Val
                245                 250                 255 gac ttc gcc aaa agg cgg gag ccc gac cgg gag agg ctt agg gcc ttt      816
Asp Phe Ala Lys Arg Arg Glu Pro Asp Arg Glu Arg Leu Arg Ala Phe
            260                 265                 270 ctg gag agg ctt gag ttt ggc agc ctc ctc cac gag ttc ggc ctt ctg      864
Leu Glu Arg Leu Glu Phe Gly Ser Leu Leu His Glu Phe Gly Leu Leu
        275                 280                 285 gaa agc ccc aag gcc ctg gag gag gcc ccc tgg ccc ccg ccg gaa ggg      912
Glu Ser Pro Lys Ala Leu Glu Glu Ala Pro Trp Pro Pro Pro Glu Gly
    290                 295                 300 gcc ttc gtg ggc ttt gtg ctt tcc cgc aag gag ccc atg tgg gcc gat      960
Ala Phe Val Gly Phe Val Leu Ser Arg Lys Glu Pro Met Trp Ala Asp
305                 310                 315                 320 ctt ctg gcc ctg gcc gcc gcc agg ggg ggc cgg gtc cac cgg gcc ccc     1008
Leu Leu Ala Leu Ala Ala Ala Arg Gly Gly Arg Val His Arg Ala Pro
                325                 330                 335 gag cct tat aaa gcc ctc agg gac ctg aag gag gcg cgg ggg ctt ctc     1056
Glu Pro Tyr Lys Ala Leu Arg Asp Leu Lys Glu Ala Arg Gly Leu Leu
            340                 345                 350 gcc aaa gac ctg agc gtt ctg gcc ctg agg gaa ggc ctt ggc ctc ccg     1104
Ala Lys Asp Leu Ser Val Leu Ala Leu Arg Glu Gly Leu Gly Leu Pro
        355                 360                 365 ccc ggc gac gac ccc atg ctc ctc gcc tac ctc ctg gac cct tcc aac     1152
Pro Gly Asp Asp Pro Met Leu Leu Ala Tyr Leu Leu Asp Pro Ser Asn
    370                 375                 380 acc acc ccc gag ggg gtg gcc cgg cgc tac ggc ggg gag tgg acg gag     1200
Thr Thr Pro Glu Gly Val Ala Arg Arg Tyr Gly Gly Glu Trp Thr Glu
385                 390                 395                 400 gag gcg ggg gag cgg gcc gcc ctt tcc gag agg ctc ttc gcc aac ctg     1248
Glu Ala Gly Glu Arg Ala Ala Leu Ser Glu Arg Leu Phe Ala Asn Leu
                405                 410                 415 tgg ggg agg ctt gag ggg gag gag agg ctc ctt tgg ctt tac cgg gag     1296
Trp Gly Arg Leu Glu Gly Glu Glu Arg Leu Leu Trp Leu Tyr Arg Glu
            420                 425                 430 gtg gag agg ccc ctt tcc gct gtc ctg gcc cac atg gag gcc acg ggg     1344
Val Glu Arg Pro Leu Ser Ala Val Leu Ala His Met Glu Ala Thr Gly
        435                 440                 445 gtg cgc ctg gac gtg gcc tat ctc agg gcc ttg tcc ctg gag gtg gcc     1392
Val Arg Leu Asp Val Ala Tyr Leu Arg Ala Leu Ser Leu Glu Val Ala
    450                 455                 460 gag gag atc gcc cgc ctc gag gcc gag gtc ttc cgc ctg gcc ggc cac     1440
Glu Glu Ile Ala Arg Leu Glu Ala Glu Val Phe Arg Leu Ala Gly His
465                 470                 475                 480 ccc ttc aac ctc aac tcc cgg gac cag ctg gaa agg gtc ctc ttt gac     1488
Pro Phe Asn Leu Asn Ser Arg Asp Gln Leu Glu Arg Val Leu Phe Asp
                485                 490                 495 gag cta ggg ctt ccc gcc atc ggc aag acg gag aag acc ggc aag cgc     1536
Glu Leu Gly Leu Pro Ala Ile Gly Lys Thr Glu Lys Thr Gly Lys Arg
            500                 505                 510 tcc acc agc gcc gcc gtc ctg gag gcc ctc cgc gag gcc cac ccc atc     1584
Ser Thr Ser Ala Ala Val Leu Glu Ala Leu Arg Glu Ala His Pro Ile
```

-continued

| | |
|---|---|
| gtg gag aag atc ctg cag tac cgg gag ctc acc aag ctg aag agc acc<br>Val Glu Lys Ile Leu Gln Tyr Arg Glu Leu Thr Lys Leu Lys Ser Thr<br>530                    535                    540 | 1632 |
| tac att gac ccc ttg ccg gac ctc atc cac ccc agg acg ggc cgc ctc<br>Tyr Ile Asp Pro Leu Pro Asp Leu Ile His Pro Arg Thr Gly Arg Leu<br>545                    550                    555                    560 | 1680 |
| cac acc cgc ttc aac cag acg gcc acg gcc acg ggc agg cta agt agc<br>His Thr Arg Phe Asn Gln Thr Ala Thr Ala Thr Gly Arg Leu Ser Ser<br>                    565                    570                    575 | 1728 |
| tcc gat ccc aac ctc cag aac atc ccc gtc cgc acc ccg ctt ggg cag<br>Ser Asp Pro Asn Leu Gln Asn Ile Pro Val Arg Thr Pro Leu Gly Gln<br>            580                    585                    590 | 1776 |
| agg atc cgc cgg gcc ttc atc gcc gag gag ggg tgg cta ttg gtg gcc<br>Arg Ile Arg Arg Ala Phe Ile Ala Glu Glu Gly Trp Leu Leu Val Ala<br>                    595                    600                    605 | 1824 |
| ctg gac tat agc cag ata gag ctc agg gtg ctg gcc cac ctc tcc ggc<br>Leu Asp Tyr Ser Gln Ile Glu Leu Arg Val Leu Ala His Leu Ser Gly<br>610                    615                    620 | 1872 |
| gac gag aac ctg atc cgg gtc ttc cag gag ggg cgg gac atc cac acg<br>Asp Glu Asn Leu Ile Arg Val Phe Gln Glu Gly Arg Asp Ile His Thr<br>625                    630                    635                    640 | 1920 |
| gag acc gcc agc tgg atg ttc ggc gtc ccc cgg gag gcc gtg gac ccc<br>Glu Thr Ala Ser Trp Met Phe Gly Val Pro Arg Glu Ala Val Asp Pro<br>                    645                    650                    655 | 1968 |
| ctg atg cgc cgg gcg gcc aag acc atc aac ttc ggg gtc ctc tac ggc<br>Leu Met Arg Arg Ala Ala Lys Thr Ile Asn Phe Gly Val Leu Tyr Gly<br>            660                    665                    670 | 2016 |
| atg tcg gcc cac cgc ctc tcc cag gag cta gcc atc cct tac gag gag<br>Met Ser Ala His Arg Leu Ser Gln Glu Leu Ala Ile Pro Tyr Glu Glu<br>                    675                    680                    685 | 2064 |
| gcc cag gcc ttc att gag cgc tac ttt cag agc ttc ccc aag gtg cgg<br>Ala Gln Ala Phe Ile Glu Arg Tyr Phe Gln Ser Phe Pro Lys Val Arg<br>690                    695                    700 | 2112 |
| gcc tgg att gag aag acc ctg gag gag ggc agg agg cgg ggg tac gtg<br>Ala Trp Ile Glu Lys Thr Leu Glu Glu Gly Arg Arg Arg Gly Tyr Val<br>705                    710                    715                    720 | 2160 |
| gag acc ctc ttc ggc cgc cgc cgc tac gtg cca gac cta gag gcc cgg<br>Glu Thr Leu Phe Gly Arg Arg Arg Tyr Val Pro Asp Leu Glu Ala Arg<br>                    725                    730                    735 | 2208 |
| gtg aag agc gtg cgg gag gcg gcc gag cgc atg gcc ttc aac atg ccc<br>Val Lys Ser Val Arg Glu Ala Ala Glu Arg Met Ala Phe Asn Met Pro<br>            740                    745                    750 | 2256 |
| gtc cag ggc acc gcc gcc gac ctc atg aag ctg gct atg gtg aag ctc<br>Val Gln Gly Thr Ala Ala Asp Leu Met Lys Leu Ala Met Val Lys Leu<br>                    755                    760                    765 | 2304 |
| ttc ccc agg ctg gag gaa atg ggg gcc agg atg ctc ctt cag gtc cac<br>Phe Pro Arg Leu Glu Glu Met Gly Ala Arg Met Leu Leu Gln Val His<br>770                    775                    780 | 2352 |
| gac gag ctg gtc ctc gag gcc cca aaa gag agg gcg gag gcc gtg gcc<br>Asp Glu Leu Val Leu Glu Ala Pro Lys Glu Arg Ala Glu Ala Val Ala<br>785                    790                    795                    800 | 2400 |
| cgg ctg gcc aag gag gtc atg gag ggg gtg tat ccc ctg gcc gtg ccc<br>Arg Leu Ala Lys Glu Val Met Glu Gly Val Tyr Pro Leu Ala Val Pro<br>                    805                    810                    815 | 2448 |
| ctg gag gtg gag gtg ggg ata ggg gag gac tgg ctc tcc gcc aag gag<br>Leu Glu Val Glu Val Gly Ile Gly Glu Asp Trp Leu Ser Ala Lys Glu<br>820                    825                    830 | 2496 |
| tga | 2499 |

<210> SEQ ID NO 8
<211> LENGTH: 832
<212> TYPE: PRT
<213> ORGANISM: Thermus aquaticus

<400> SEQUENCE: 8

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
```

-continued

```
            370                 375                 380
Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800
```

```
Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 9
<211> LENGTH: 2499
<212> TYPE: DNA
<213> ORGANISM: Artificial sequence
<220> FEATURE:
<223> OTHER INFORMATION: Taq Exo-
<220> FEATURE:
<221> NAME/KEY: CDS
<222> LOCATION: (1)..(2499)

<400> SEQUENCE: 9 atg agg ggg atg ctg ccc ctc ttt gag ccc aag ggc cgg gtc ctc ctg      48
Met Arg Gly Met Leu Pro Leu Phe Glu Pro Lys Gly Arg Val Leu Leu
1               5                   10                  15 gtg gac ggc cac cac ctg gcc tac cgc acc ttc cac gcc ctg aag ggc      96
Val Asp Gly His His Leu Ala Tyr Arg Thr Phe His Ala Leu Lys Gly
            20                  25                  30 ctc acc acc agc cgg ggg gag ccg gtg cag gcg gtc tac ggc ttc gcc     144
Leu Thr Thr Ser Arg Gly Glu Pro Val Gln Ala Val Tyr Gly Phe Ala
        35                  40                  45 aag agc ctc ctc aag gcc ctc aag gag gac ggg gac gcg gtg atc gtg     192
Lys Ser Leu Leu Lys Ala Leu Lys Glu Asp Gly Asp Ala Val Ile Val
    50                  55                  60 gtc ttt gac gcc aag gcc ccc tcc ttc cgc cac gag gcc tac ggg ggg     240
Val Phe Asp Ala Lys Ala Pro Ser Phe Arg His Glu Ala Tyr Gly Gly
65                  70                  75                  80 tac aag gcg ggc cgg gcc ccc acg ccg gag gac ttt ccc cgg caa ctc     288
Tyr Lys Ala Gly Arg Ala Pro Thr Pro Glu Asp Phe Pro Arg Gln Leu
                85                  90                  95 gcc ctc atc aag gag ctg gtg gac ctc ctg ggg ctg gcg cgc ctc gag     336
Ala Leu Ile Lys Glu Leu Val Asp Leu Leu Gly Leu Ala Arg Leu Glu
            100                 105                 110 gtc ccg ggc tac gcg gcg gcc gac gtc ctg gcc agc ctg gcc aag aag     384
Val Pro Gly Tyr Ala Ala Ala Asp Val Leu Ala Ser Leu Ala Lys Lys
        115                 120                 125 gcg gaa aag gag ggc tac gag gtc cgc atc ctc acc gcc gcc aaa gcc     432
Ala Glu Lys Glu Gly Tyr Glu Val Arg Ile Leu Thr Ala Ala Lys Ala
    130                 135                 140 ctt tac cag ctc ctt tcc gac cgc atc cac gtc ctc cac ccc gag ggg     480
Leu Tyr Gln Leu Leu Ser Asp Arg Ile His Val Leu His Pro Glu Gly
145                 150                 155                 160 tac ctc atc acc ccg gcc tgg ctt tgg gaa aag tac ggc ctg agg ccc     528
Tyr Leu Ile Thr Pro Ala Trp Leu Trp Glu Lys Tyr Gly Leu Arg Pro
                165                 170                 175 gac cag tgg gcc gac tac cgg gcc ctg acc ggg gac gag tcc gac aac     576
Asp Gln Trp Ala Asp Tyr Arg Ala Leu Thr Gly Asp Glu Ser Asp Asn
            180                 185                 190 ctt ccc ggg gtc aag ggc atc ggg gag aag acg gcg agg aag ctt ctg     624
Leu Pro Gly Val Lys Gly Ile Gly Glu Lys Thr Ala Arg Lys Leu Leu
        195                 200                 205 gag gag tgg ggg agc ctg gaa gcc ctc ctc aag aac ctg gac cgg ctg     672
Glu Glu Trp Gly Ser Leu Glu Ala Leu Leu Lys Asn Leu Asp Arg Leu
    210                 215                 220 aag ccc gcc atc cgg gag aag atc ctg gcc cac atg gac gat ctg aag     720
Lys Pro Ala Ile Arg Glu Lys Ile Leu Ala His Met Asp Asp Leu Lys
225                 230                 235                 240
```

| | | |
|---|---|---|
| ctc tcc tgg gac ctg gcc aag gtg cgc acc gac ctg ccc ctg gag gtg<br>Leu Ser Trp Asp Leu Ala Lys Val Arg Thr Asp Leu Pro Leu Glu Val<br>              245                  250                  255 | 768 |
| gac ttc gcc aaa agg cgg gag ccc gac cgg gag agg ctt agg gcc ttt<br>Asp Phe Ala Lys Arg Arg Glu Pro Asp Arg Glu Arg Leu Arg Ala Phe<br>            260                      265                270 | 816 |
| ctg gag agg ctt gag ttt ggc agc ctc ctc cac gag ttc ggc ctt ctg<br>Leu Glu Arg Leu Glu Phe Gly Ser Leu Leu His Glu Phe Gly Leu Leu<br>        275                      280                  285 | 864 |
| gaa agc ccc aag gcc ctg gag gag gcc ccc tgg ccc ccg ccg gaa ggg<br>Glu Ser Pro Lys Ala Leu Glu Glu Ala Pro Trp Pro Pro Pro Glu Gly<br>290                      295                  300 | 912 |
| gcc ttc gtg ggc ttt gtg ctt tcc cgc aag gag ccc atg tgg gcc gat<br>Ala Phe Val Gly Phe Val Leu Ser Arg Lys Glu Pro Met Trp Ala Asp<br>305                  310                  315              320 | 960 |
| ctt ctg gcc ctg gcc gcc gcc agg ggg ggc cgg gtc cac cgg gcc ccc<br>Leu Leu Ala Leu Ala Ala Ala Arg Gly Gly Arg Val His Arg Ala Pro<br>                325                  330              335 | 1008 |
| gag cct tat aaa gcc ctc agg gac ctg aag gag gcg cgg ggg ctt ctc<br>Glu Pro Tyr Lys Ala Leu Arg Asp Leu Lys Glu Ala Arg Gly Leu Leu<br>            340                  345                  350 | 1056 |
| gcc aaa gac ctg agc gtt ctg gcc ctg agg gaa ggc ctt ggc ctc ccg<br>Ala Lys Asp Leu Ser Val Leu Ala Leu Arg Glu Gly Leu Gly Leu Pro<br>        355                      360                  365 | 1104 |
| ccc ggc gac gac ccc atg ctc ctc gcc tac ctc ctg gac cct tcc aac<br>Pro Gly Asp Asp Pro Met Leu Leu Ala Tyr Leu Leu Asp Pro Ser Asn<br>370                      375                  380 | 1152 |
| acc acc ccc gag ggg gtg gcc cgg cgc tac ggc ggg gag tgg acg gag<br>Thr Thr Pro Glu Gly Val Ala Arg Arg Tyr Gly Gly Glu Trp Thr Glu<br>385                390                  395              400 | 1200 |
| gag gcg ggg gag cgg gcc gcc ctt tcc gag agg ctc ttc gcc aac ctg<br>Glu Ala Gly Glu Arg Ala Ala Leu Ser Glu Arg Leu Phe Ala Asn Leu<br>                405                  410              415 | 1248 |
| tgg ggg agg ctt gag ggg gag gag agg ctc ctt tgg ctt tac cgg gag<br>Trp Gly Arg Leu Glu Gly Glu Glu Arg Leu Leu Trp Leu Tyr Arg Glu<br>            420                  425                  430 | 1296 |
| gtg gag agg ccc ctt tcc gct gtc ctg gcc cac atg gag gcc acg ggg<br>Val Glu Arg Pro Leu Ser Ala Val Leu Ala His Met Glu Ala Thr Gly<br>        435                      440                  445 | 1344 |
| gtg cgc ctg gac gtg gcc tat ctc agg gcc ttg tcc ctg gag gtg gcc<br>Val Arg Leu Asp Val Ala Tyr Leu Arg Ala Leu Ser Leu Glu Val Ala<br>450                      455                  460 | 1392 |
| gag gag atc gcc cgc ctc gag gcc gag gtc ttc cgc ctg gcc ggc cac<br>Glu Glu Ile Ala Arg Leu Glu Ala Glu Val Phe Arg Leu Ala Gly His<br>465                  470                  475              480 | 1440 |
| ccc ttc aac ctc aac tcc cgg gac cag ctg gaa agg gtc ctc ttt gac<br>Pro Phe Asn Leu Asn Ser Arg Asp Gln Leu Glu Arg Val Leu Phe Asp<br>                485                  490              495 | 1488 |
| gag cta ggg ctt ccc gcc atc ggc aag acg gag aag acc ggc aag cgc<br>Glu Leu Gly Leu Pro Ala Ile Gly Lys Thr Glu Lys Thr Gly Lys Arg<br>            500                  505                  510 | 1536 |
| tcc acc agc gcc gcc gtc ctg gag gcc ctc cgc gag gcc cac ccc atc<br>Ser Thr Ser Ala Ala Val Leu Glu Ala Leu Arg Glu Ala His Pro Ile<br>        515                      520                  525 | 1584 |
| gtg gag aag atc ctg cag tac cgg gag ctc acc aag ctg aag agc acc<br>Val Glu Lys Ile Leu Gln Tyr Arg Glu Leu Thr Lys Leu Lys Ser Thr<br>530                      535                  540 | 1632 |
| tac att gac ccc ttg ccg gac ctc atc cac ccc agg acg ggc cgc ctc<br>Tyr Ile Asp Pro Leu Pro Asp Leu Ile His Pro Arg Thr Gly Arg Leu | 1680 |

```
                  545                 550                 555                 560
cac acc cgc ttc aac cag acg gcc acg gcc acg ggc agg cta agt agc         1728
His Thr Arg Phe Asn Gln Thr Ala Thr Ala Thr Gly Arg Leu Ser Ser
                565                 570                 575 tcc gat ccc aac ctc cag aac atc ccc gtc cgc acc ccg ctt ggg cag         1776
Ser Asp Pro Asn Leu Gln Asn Ile Pro Val Arg Thr Pro Leu Gly Gln
            580                 585                 590 agg atc cgc cgg gcc ttc atc gcc gag gag ggg tgg cta ttg gtg gcc         1824
Arg Ile Arg Arg Ala Phe Ile Ala Glu Glu Gly Trp Leu Leu Val Ala
        595                 600                 605 ctg gac tat agc cag ata gag ctc agg gtg ctg gcc cac ctc tcc ggc         1872
Leu Asp Tyr Ser Gln Ile Glu Leu Arg Val Leu Ala His Leu Ser Gly
    610                 615                 620 gac gag aac ctg atc cgg gtc ttc cag gag ggg cgg gac atc cac acg         1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc         1968
Glu Thr Ala Ser Trp Met Phe Gly Val Pro Arg Glu Ala Val Asp Pro
                645                 650                 655 ctg atg cgc cgg gcg gcc aag acc atc aac ttc ggg gtc ctc tac ggc         2016
Leu Met Arg Arg Ala Ala Lys Thr Ile Asn Phe Gly Val Leu Tyr Gly
            660                 665                 670 atg tcg gcc cac cgc ctc tcc cag gag cta gcc atc cct tac gag gag         2064
Met Ser Ala His Arg Leu Ser Gln Glu Leu Ala Ile Pro Tyr Glu Glu
        675                 680                 685 gcc cag gcc ttc att gag cgc tac ttt cag agc ttc ccc aag gtg cgg         2112
Ala Gln Ala Phe Ile Glu Arg Tyr Phe Gln Ser Phe Pro Lys Val Arg
    690                 695                 700 gcc tgg att gag aag acc ctg gag gag ggc agg agg cgg ggg tac gtg         2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg         2208
Glu Thr Leu Phe Gly Arg Arg Arg Tyr Val Pro Asp Leu Glu Ala Arg
                725                 730                 735 gtg aag agc gtg cgg gag gcg gcc gag cgc atg gcc ttc aac atg ccc         2256
Val Lys Ser Val Arg Glu Ala Ala Glu Arg Met Ala Phe Asn Met Pro
            740                 745                 750 gtc cag ggc acc gcc gcc gac ctc atg aag ctg gct atg gtg aag ctc         2304
Val Gln Gly Thr Ala Ala Asp Leu Met Lys Leu Ala Met Val Lys Leu
        755                 760                 765 ttc ccc agg ctg gag gaa atg ggg gcc agg atg ctc ctt cag gtc cac         2352
Phe Pro Arg Leu Glu Glu Met Gly Ala Arg Met Leu Leu Gln Val His
    770                 775                 780 gac gag ctg gtc ctc gag gcc cca aaa gag agg gcg gag gcc gtg gcc         2400
Asp Glu Leu Val Leu Glu Ala Pro Lys Glu Arg Ala Glu Ala Val Ala
785                 790                 795                 800 cgg ctg gcc aag gag gtc atg gag ggg gtg tat ccc ctg gcc gtg ccc         2448
Arg Leu Ala Lys Glu Val Met Glu Gly Val Tyr Pro Leu Ala Val Pro
                805                 810                 815 ctg gag gtg gag gtg ggg ata ggg gag gac tgg ctc tcc gcc aag gag         2496
Leu Glu Val Glu Val Gly Ile Gly Glu Asp Trp Leu Ser Ala Lys Glu
            820                 825                 830 tga                                                                      2499
```

<210> SEQ ID NO 10
<211> LENGTH: 832
<212> TYPE: PRT
<213> ORGANISM: Artificial sequence
<220> FEATURE:
<223> OTHER INFORMATION: Synthetic Construct

<400> SEQUENCE: 10

| Met | Arg | Gly | Met | Leu | Pro | Leu | Phe | Glu | Pro | Lys | Gly | Arg | Val | Leu | Leu |
|---|---|---|---|---|---|---|---|---|---|---|---|---|---|---|---|
| 1 | | | | 5 | | | | | 10 | | | | | 15 | |

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Gly Leu Ala Arg Leu Glu
                100                 105                 110

Val Pro Gly Tyr Ala Ala Asp Val Leu Ala Ser Leu Ala Lys Lys
            115                 120                 125

Ala Glu Lys Glu Gly Tyr Glu Val Arg Ile Leu Thr Ala Ala Lys Ala
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu

```
                405                 410                 415
Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

<210> SEQ ID NO 11
<211> LENGTH: 2526
<212> TYPE: DNA
<213> ORGANISM: Artificial sequence
<220> FEATURE:
<223> OTHER INFORMATION: Taq 9aa
<220> FEATURE:
<221> NAME/KEY: CDS
<222> LOCATION: (1)..(2526)

<400> SEQUENCE: 11

| | | | | | | | | | | | | | | | | |
|---|---|---|---|---|---|---|---|---|---|---|---|---|---|---|---|---|
| atg | agg | ggg | atg | ctg | ccc | ctc | ttt | gag | ccc | aag | ggc | cgg | gtc | ctc | ctg | 48 |
| Met | Arg | Gly | Met | Leu | Pro | Leu | Phe | Glu | Pro | Lys | Gly | Arg | Val | Leu | Leu | |
| 1 | | | | 5 | | | | | 10 | | | | | 15 | | |
| gtg | gac | ggc | cac | cac | ctg | gcc | tac | cgc | acc | ttc | cac | gcc | ctg | aag | ggc | 96 |
| Val | Asp | Gly | His | His | Leu | Ala | Tyr | Arg | Thr | Phe | His | Ala | Leu | Lys | Gly | |
| | | | 20 | | | | | 25 | | | | | 30 | | | |
| ctc | acc | acc | agc | cgg | ggg | gag | ccg | gtg | cag | gcg | gtc | tac | ggc | ttc | gcc | 144 |
| Leu | Thr | Thr | Ser | Arg | Gly | Glu | Pro | Val | Gln | Ala | Val | Tyr | Gly | Phe | Ala | |
| | | 35 | | | | | 40 | | | | | 45 | | | | |
| aag | agc | ctc | ctc | aag | gcc | ctc | aag | gag | gac | ggg | gac | gcg | gtg | atc | gtg | 192 |
| Lys | Ser | Leu | Leu | Lys | Ala | Leu | Lys | Glu | Asp | Gly | Asp | Ala | Val | Ile | Val | |
| | 50 | | | | | 55 | | | | | 60 | | | | | |
| gtc | ttt | gac | gcc | aag | gcc | ccc | tcc | ttc | cgc | cac | gag | gcc | tac | ggg | ggg | 240 |
| Val | Phe | Asp | Ala | Lys | Ala | Pro | Ser | Phe | Arg | His | Glu | Ala | Tyr | Gly | Gly | |
| 65 | | | | | 70 | | | | | 75 | | | | | 80 | |
| tac | aag | gcg | ggc | cgg | gcc | ccc | acg | ccg | gag | gac | ttt | ccc | cgg | caa | ctc | 288 |
| Tyr | Lys | Ala | Gly | Arg | Ala | Pro | Thr | Pro | Glu | Asp | Phe | Pro | Arg | Gln | Leu | |
| | | | | 85 | | | | | 90 | | | | | 95 | | |
| gcc | ctc | atc | aag | gag | ctg | gtg | gac | ctc | ctg | ggg | ctg | gcg | cgc | ctc | gag | 336 |
| Ala | Leu | Ile | Lys | Glu | Leu | Val | Asp | Leu | Leu | Gly | Leu | Ala | Arg | Leu | Glu | |
| | | | 100 | | | | | 105 | | | | | 110 | | | |
| gtc | ccg | ggc | tac | gag | gcg | gac | gac | gtc | ctg | gcc | agc | ctg | gcc | aag | aag | 384 |
| Val | Pro | Gly | Tyr | Glu | Ala | Asp | Asp | Val | Leu | Ala | Ser | Leu | Ala | Lys | Lys | |
| | | 115 | | | | | 120 | | | | | 125 | | | | |
| gcg | gaa | aag | gag | ggc | tac | gag | gtc | cgc | atc | ctc | acc | gcc | gac | aaa | gac | 432 |
| Ala | Glu | Lys | Glu | Gly | Tyr | Glu | Val | Arg | Ile | Leu | Thr | Ala | Asp | Lys | Asp | |
| | 130 | | | | | 135 | | | | | 140 | | | | | |
| ctt | tac | cag | ctc | ctt | tcc | gac | cgc | atc | cac | gtc | ctc | cac | ccc | gag | ggg | 480 |
| Leu | Tyr | Gln | Leu | Leu | Ser | Asp | Arg | Ile | His | Val | Leu | His | Pro | Glu | Gly | |
| 145 | | | | | 150 | | | | | 155 | | | | | 160 | |
| tac | ctc | atc | acc | ccg | gcc | tgg | ctt | tgg | gaa | aag | tac | ggc | ctg | agg | ccc | 528 |
| Tyr | Leu | Ile | Thr | Pro | Ala | Trp | Leu | Trp | Glu | Lys | Tyr | Gly | Leu | Arg | Pro | |
| | | | | 165 | | | | | 170 | | | | | 175 | | |
| gac | cag | tgg | gcc | gac | tac | cgg | gcc | ctg | acc | ggg | gac | gag | tcc | gac | aac | 576 |
| Asp | Gln | Trp | Ala | Asp | Tyr | Arg | Ala | Leu | Thr | Gly | Asp | Glu | Ser | Asp | Asn | |
| | | | 180 | | | | | 185 | | | | | 190 | | | |
| ctt | ccc | ggg | gtc | aag | ggc | atc | ggg | gag | aag | acg | gcg | agg | aag | ctt | ctg | 624 |
| Leu | Pro | Gly | Val | Lys | Gly | Ile | Gly | Glu | Lys | Thr | Ala | Arg | Lys | Leu | Leu | |
| | | 195 | | | | | 200 | | | | | 205 | | | | |
| gag | gag | tgg | ggg | agc | ctg | gaa | gcc | ctc | ctc | aag | aac | ctg | gac | cgg | ctg | 672 |
| Glu | Glu | Trp | Gly | Ser | Leu | Glu | Ala | Leu | Leu | Lys | Asn | Leu | Asp | Arg | Leu | |
| | 210 | | | | | 215 | | | | | 220 | | | | | |
| aag | ccc | gcc | atc | cgg | gag | aag | atc | ctg | gcc | cac | atg | gac | gat | ctg | aag | 720 |
| Lys | Pro | Ala | Ile | Arg | Glu | Lys | Ile | Leu | Ala | His | Met | Asp | Asp | Leu | Lys | |
| 225 | | | | | 230 | | | | | 235 | | | | | 240 | |
| ctc | tcc | tgg | gac | ctg | gcc | aag | gtg | cgc | acc | gac | ctg | ccc | ctg | gag | gtg | 768 |
| Leu | Ser | Trp | Asp | Leu | Ala | Lys | Val | Arg | Thr | Asp | Leu | Pro | Leu | Glu | Val | |
| | | | | 245 | | | | | 250 | | | | | 255 | | |
| gac | ttc | gcc | aaa | agg | cgg | gag | ccc | gac | cgg | gag | agg | ctt | agg | gcc | ttt | 816 |

```
                Asp Phe Ala Lys Arg Arg Glu Pro Asp Arg Glu Arg Leu Arg Ala Phe
                            260                 265                 270 ctg gag agg ctt gag ttt ggc agc ctc ctc cac gag ttc ggc ctt ctg        864
Leu Glu Arg Leu Glu Phe Gly Ser Leu Leu His Glu Phe Gly Leu Leu
            275                 280                 285 gaa agc ccc aag gcc ctg gag gag gcc ccc tgg ccc ccg ccg gaa ggg        912
Glu Ser Pro Lys Ala Leu Glu Glu Ala Pro Trp Pro Pro Pro Glu Gly
        290                 295                 300 gcc ttc gtg ggc ttt gtg ctt tcc cgc aag gag ccc atg tgg gcc gat        960
Ala Phe Val Gly Phe Val Leu Ser Arg Lys Glu Pro Met Trp Ala Asp
305                 310                 315                 320 ctt ctg gcc ctg gcc gcc gcc agg ggg ggc cgg gtc cac cgg gcc ccc       1008
Leu Leu Ala Leu Ala Ala Ala Arg Gly Gly Arg Val His Arg Ala Pro
                325                 330                 335 gag cct tat aaa gcc ctc agg gac ctg aag gag gcg cgg ggg ctt ctc       1056
Glu Pro Tyr Lys Ala Leu Arg Asp Leu Lys Glu Ala Arg Gly Leu Leu
            340                 345                 350 gcc aaa gac ctg agc gtt ctg gcc ctg agg gaa ggc ctt ggc ctc ccg       1104
Ala Lys Asp Leu Ser Val Leu Ala Leu Arg Glu Gly Leu Gly Leu Pro
        355                 360                 365 ccc ggc gac gac ccc atg ctc ctc gcc tac ctc ctg gac cct tcc aac       1152
Pro Gly Asp Asp Pro Met Leu Leu Ala Tyr Leu Leu Asp Pro Ser Asn
370                 375                 380 acc acc ccc gag ggg gtg gcc cgg cgc tac ggc ggg gag tgg acg gag       1200
Thr Thr Pro Glu Gly Val Ala Arg Arg Tyr Gly Gly Glu Trp Thr Glu
385                 390                 395                 400 gag gcg ggg gag cgg gcc gcc ctt tcc gag agg ctc ttc gcc aac ctg       1248
Glu Ala Gly Glu Arg Ala Ala Leu Ser Glu Arg Leu Phe Ala Asn Leu
                405                 410                 415 tgg ggg agg ctt gag ggg gag gag agg ctc ctt tgg ctt tac cgg gag       1296
Trp Gly Arg Leu Glu Gly Glu Glu Arg Leu Leu Trp Leu Tyr Arg Glu
            420                 425                 430 gtg gag agg ccc ctt tcc gct gtc ctg gcc cac atg gag gcc acg ggg       1344
Val Glu Arg Pro Leu Ser Ala Val Leu Ala His Met Glu Ala Thr Gly
        435                 440                 445 gtg cgc ctg gac gtg gcc tat ctc agg gcc ttg tcc ctg gag gtg gcc       1392
Val Arg Leu Asp Val Ala Tyr Leu Arg Ala Leu Ser Leu Glu Val Ala
450                 455                 460 gag gag atc gcc cgc ctc gag gcc gag gtc ttc cgc ctg gcc ggc cac       1440
Glu Glu Ile Ala Arg Leu Glu Ala Glu Val Phe Arg Leu Ala Gly His
465                 470                 475                 480 ccc ttc aac ctc aac tcc cgg gac cag ctg gaa agg gtc ctc ttt gac       1488
Pro Phe Asn Leu Asn Ser Arg Asp Gln Leu Glu Arg Val Leu Phe Asp
                485                 490                 495 gag cta ggg ctt ccc gcc atc ggc aag acg gag aag acc ggc aag cgc       1536
Glu Leu Gly Leu Pro Ala Ile Gly Lys Thr Glu Lys Thr Gly Lys Arg
            500                 505                 510 tcc acc agc gcc gcc gtc ctg gag gcc ctc cgc gag gcc cac ccc atc       1584
Ser Thr Ser Ala Ala Val Leu Glu Ala Leu Arg Glu Ala His Pro Ile
        515                 520                 525 gtg gag aag atc ctg cag tac cgg gag ctc acc aag ctg aag agc acc       1632
Val Glu Lys Ile Leu Gln Tyr Arg Glu Leu Thr Lys Leu Lys Ser Thr
530                 535                 540 tac att gac ccc ttg ccg gac ctc atc cac ccc agg acg ggc cgc ctc       1680
Tyr Ile Asp Pro Leu Pro Asp Leu Ile His Pro Arg Thr Gly Arg Leu
545                 550                 555                 560 cac acc cgc ttc aac cag acg gcc acg gcc acg ggc agg cta agt agc       1728
His Thr Arg Phe Asn Gln Thr Ala Thr Ala Thr Gly Arg Leu Ser Ser
                565                 570                 575
```

| | | | | | | | | | | | | | | | |
|---|---|---|---|---|---|---|---|---|---|---|---|---|---|---|---|
| tcc | gat | ccc | aac | ctc | cag | aac | atc | ccc | gtc | cgc | acc | ccg | ctt | ggg | cag | 1776 |
| Ser | Asp | Pro | Asn | Leu | Gln | Asn | Ile | Pro | Val | Arg | Thr | Pro | Leu | Gly | Gln | |
| | | | 580 | | | | 585 | | | | | 590 | | | | |

```
tcc gat ccc aac ctc cag aac atc ccc gtc cgc acc ccg ctt ggg cag    1776
Ser Asp Pro Asn Leu Gln Asn Ile Pro Val Arg Thr Pro Leu Gly Gln
            580                 585                 590 agg atc cgc cgg gcc ttc atc gcc gag gag ggg tgg cta ttg gtg gcc    1824
Arg Ile Arg Arg Ala Phe Ile Ala Glu Glu Gly Trp Leu Leu Val Ala
            595                 600                 605 ctg gac tat agc cag ata gag ctc agg gtg ctg gcc cac ctc tcc ggc    1872
Leu Asp Tyr Ser Gln Ile Glu Leu Arg Val Leu Ala His Leu Ser Gly
            610                 615                 620 gac gag aac ctg atc cgg gtc ttc cag gag ggg cgg gac atc cac acg    1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc    1968
Glu Thr Ala Ser Trp Met Phe Gly Val Pro Arg Glu Ala Val Asp Pro
            645                 650                 655 ctg atg cgc cgg gcg gcc aag acc atc aac ttc ggg gtc ctc tac ggc    2016
Leu Met Arg Arg Ala Ala Lys Thr Ile Asn Phe Gly Val Leu Tyr Gly
            660                 665                 670 atg tcg gcc cac cgc ctc tcc cag gag cta gcc atc cct tac gag gag    2064
Met Ser Ala His Arg Leu Ser Gln Glu Leu Ala Ile Pro Tyr Glu Glu
            675                 680                 685 gcc cag gcc ttc att gag cgc tac ttt cag agc ttc ccc aag gtg cgg    2112
Ala Gln Ala Phe Ile Glu Arg Tyr Phe Gln Ser Phe Pro Lys Val Arg
690                 695                 700 gcc tgg att gag aag acc ctg gag gag ggc agg agg cgg ggg tac gtg    2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg    2208
Glu Thr Leu Phe Gly Arg Arg Arg Tyr Val Pro Asp Leu Glu Ala Arg
            725                 730                 735 ggc ccg cgc cgg gcg ccg cgt cgt ctg gtg aag agc gtg cgg gag gcg    2256
Gly Pro Arg Arg Ala Pro Arg Arg Leu Val Lys Ser Val Arg Glu Ala
            740                 745                 750 gcc gag cgc atg gcc ttc aac atg ccc gtc cag ggc acc gcc gcc gac    2304
Ala Glu Arg Met Ala Phe Asn Met Pro Val Gln Gly Thr Ala Ala Asp
            755                 760                 765 ctc atg aag ctg gct atg gtg aag ctc ttc ccc agg ctg gag gaa atg    2352
Leu Met Lys Leu Ala Met Val Lys Leu Phe Pro Arg Leu Glu Glu Met
770                 775                 780 ggg gcc agg atg ctc ctt cag gtc cac gac gag ctg gtc ctc gag gcc    2400
Gly Ala Arg Met Leu Leu Gln Val His Asp Glu Leu Val Leu Glu Ala
785                 790                 795                 800 cca aaa gag agg gcg gag gcc gtg gcc cgg ctg gcc aag gag gtc atg    2448
Pro Lys Glu Arg Ala Glu Ala Val Ala Arg Leu Ala Lys Glu Val Met
            805                 810                 815 gag ggg gtg tat ccc ctg gcc gtg ccc ctg gag gtg gag gtg ggg ata    2496
Glu Gly Val Tyr Pro Leu Ala Val Pro Leu Glu Val Glu Val Gly Ile
            820                 825                 830 ggg gag gac tgg ctc tcc gcc aag gag tga                            2526
Gly Glu Asp Trp Leu Ser Ala Lys Glu
            835                 840
```

<210> SEQ ID NO 12
<211> LENGTH: 841
<212> TYPE: PRT
<213> ORGANISM: Artificial sequence
<220> FEATURE:
<223> OTHER INFORMATION: Synthetic Construct

<400> SEQUENCE: 12

Met Arg Gly Met Leu Pro Leu Phe Glu Pro Lys Gly Arg Val Leu Leu

-continued

```
1               5                   10                  15
Val Asp Gly His His Leu Ala Tyr Arg Thr Phe His Ala Leu Lys Gly
            20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Asp Ala Val Ile Val
        50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
            115                 120                 125
Ala Glu Lys Glu Gly Tyr Glu Val Arg Ile Leu Thr Ala Asp Lys Asp
        130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Pro Glu Gly
        290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
```

```
Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Gly Pro Arg Arg Ala Pro Arg Arg Leu Val Lys Ser Val Arg Glu Ala
            740                 745                 750

Ala Glu Arg Met Ala Phe Asn Met Pro Val Gln Gly Thr Ala Ala Asp
            755                 760                 765

Leu Met Lys Leu Ala Met Val Lys Leu Phe Pro Arg Leu Glu Glu Met
            770                 775                 780

Gly Ala Arg Met Leu Leu Gln Val His Asp Glu Leu Val Leu Glu Ala
785                 790                 795                 800

Pro Lys Glu Arg Ala Glu Ala Val Ala Arg Leu Ala Lys Glu Val Met
                805                 810                 815

Glu Gly Val Tyr Pro Leu Ala Val Pro Leu Glu Val Glu Val Gly Ile
            820                 825                 830

Gly Glu Asp Trp Leu Ser Ala Lys Glu
            835                 840
```

<210> SEQ ID NO 13
<211> LENGTH: 2526
<212> TYPE: DNA
<213> ORGANISM: Artificial Sequence
<220> FEATURE:
<223> OTHER INFORMATION: Taq Exo- 9aa
<220> FEATURE:
<221> NAME/KEY: CDS
<222> LOCATION: (1)..(2526)

<400> SEQUENCE: 13

| | | | | | | | | | | | | | | | | |
|---|---|---|---|---|---|---|---|---|---|---|---|---|---|---|---|---|
| atg | agg | ggg | atg | ctg | ccc | ctc | ttt | gag | ccc | aag | ggc | cgg | gtc | ctc | ctg | 48 |
| Met | Arg | Gly | Met | Leu | Pro | Leu | Phe | Glu | Pro | Lys | Gly | Arg | Val | Leu | Leu | |
| 1 | | | | 5 | | | | | 10 | | | | | 15 | | |
| gtg | gac | ggc | cac | cac | ctg | gcc | tac | cgc | acc | ttc | cac | gcc | ctg | aag | ggc | 96 |
| Val | Asp | Gly | His | His | Leu | Ala | Tyr | Arg | Thr | Phe | His | Ala | Leu | Lys | Gly | |
| | | | 20 | | | | | 25 | | | | | 30 | | | |
| ctc | acc | acc | agc | cgg | ggg | gag | ccg | gtg | cag | gcg | gtc | tac | ggc | ttc | gcc | 144 |
| Leu | Thr | Thr | Ser | Arg | Gly | Glu | Pro | Val | Gln | Ala | Val | Tyr | Gly | Phe | Ala | |
| | | | | 35 | | | | | 40 | | | | | 45 | | |
| aag | agc | ctc | ctc | aag | gcc | ctc | aag | gag | gac | ggg | gac | gcg | gtg | atc | gtg | 192 |
| Lys | Ser | Leu | Leu | Lys | Ala | Leu | Lys | Glu | Asp | Gly | Asp | Ala | Val | Ile | Val | |
| | 50 | | | | | 55 | | | | | 60 | | | | | |
| gtc | ttt | gac | gcc | aag | gcc | ccc | tcc | ttc | cgc | cac | gag | gcc | tac | ggg | ggg | 240 |
| Val | Phe | Asp | Ala | Lys | Ala | Pro | Ser | Phe | Arg | His | Glu | Ala | Tyr | Gly | Gly | |
| 65 | | | | | 70 | | | | | 75 | | | | | 80 | |
| tac | aag | gcg | ggc | cgg | gcc | ccc | acg | ccg | gag | gac | ttt | ccc | cgg | caa | ctc | 288 |
| Tyr | Lys | Ala | Gly | Arg | Ala | Pro | Thr | Pro | Glu | Asp | Phe | Pro | Arg | Gln | Leu | |
| | | | | 85 | | | | | 90 | | | | | 95 | | |
| gcc | ctc | atc | aag | gag | ctg | gtg | gac | ctc | ctg | ggg | ctg | gcg | cgc | ctc | gag | 336 |
| Ala | Leu | Ile | Lys | Glu | Leu | Val | Asp | Leu | Leu | Gly | Leu | Ala | Arg | Leu | Glu | |
| | | | | 100 | | | | | 105 | | | | | 110 | | |
| gtc | ccg | ggc | tac | gcg | gcg | gac | gtc | ctg | gcc | agc | ctg | gcc | aag | aag | | 384 |
| Val | Pro | Gly | Tyr | Ala | Ala | Asp | Val | Leu | Ala | Ser | Leu | Ala | Lys | Lys | | |
| | | | 115 | | | | | 120 | | | | | 125 | | | |
| gcg | gaa | aag | gag | ggc | tac | gag | gtc | cgc | atc | ctc | acc | gcc | gcc | aaa | gcc | 432 |
| Ala | Glu | Lys | Glu | Gly | Tyr | Glu | Val | Arg | Ile | Leu | Thr | Ala | Ala | Lys | Ala | |
| | 130 | | | | | 135 | | | | | 140 | | | | | |
| ctt | tac | cag | ctc | ctt | tcc | gac | cgc | atc | cac | gtc | ctc | cac | ccc | gag | ggg | 480 |
| Leu | Tyr | Gln | Leu | Leu | Ser | Asp | Arg | Ile | His | Val | Leu | His | Pro | Glu | Gly | |
| 145 | | | | | 150 | | | | | 155 | | | | | 160 | |
| tac | ctc | atc | acc | ccg | gcc | tgg | ctt | tgg | gaa | aag | tac | ggc | ctg | agg | ccc | 528 |
| Tyr | Leu | Ile | Thr | Pro | Ala | Trp | Leu | Trp | Glu | Lys | Tyr | Gly | Leu | Arg | Pro | |
| | | | | 165 | | | | | 170 | | | | | 175 | | |
| gac | cag | tgg | gcc | gac | tac | cgg | gcc | ctg | acc | ggg | gac | gag | tcc | gac | aac | 576 |
| Asp | Gln | Trp | Ala | Asp | Tyr | Arg | Ala | Leu | Thr | Gly | Asp | Glu | Ser | Asp | Asn | |
| | | | 180 | | | | | 185 | | | | | 190 | | | |
| ctt | ccc | ggg | gtc | aag | ggc | atc | ggg | gag | aag | acg | gcg | agg | aag | ctt | ctg | 624 |
| Leu | Pro | Gly | Val | Lys | Gly | Ile | Gly | Glu | Lys | Thr | Ala | Arg | Lys | Leu | Leu | |
| | | | | 195 | | | | | 200 | | | | | 205 | | |
| gag | gag | tgg | ggg | agc | ctg | gaa | gcc | ctc | ctc | aag | aac | ctg | gac | cgg | ctg | 672 |
| Glu | Glu | Trp | Gly | Ser | Leu | Glu | Ala | Leu | Leu | Lys | Asn | Leu | Asp | Arg | Leu | |
| | 210 | | | | | 215 | | | | | 220 | | | | | |
| aag | ccc | gcc | atc | cgg | gag | aag | atc | ctg | gcc | cac | atg | gac | gat | ctg | aag | 720 |
| Lys | Pro | Ala | Ile | Arg | Glu | Lys | Ile | Leu | Ala | His | Met | Asp | Asp | Leu | Lys | |
| 225 | | | | | 230 | | | | | 235 | | | | | 240 | |
| ctc | tcc | tgg | gac | ctg | gcc | aag | gtg | cgc | acc | gac | ctg | ccc | ctg | gag | gtg | 768 |
| Leu | Ser | Trp | Asp | Leu | Ala | Lys | Val | Arg | Thr | Asp | Leu | Pro | Leu | Glu | Val | |
| | | | | 245 | | | | | 250 | | | | | 255 | | |
| gac | ttc | gcc | aaa | agg | cgg | gag | ccc | gac | cgg | gag | agg | ctt | agg | gcc | ttt | 816 |
| Asp | Phe | Ala | Lys | Arg | Arg | Glu | Pro | Asp | Arg | Glu | Arg | Leu | Arg | Ala | Phe | |

-continued

|  |  |  |  |  |  |  |  |  |  |  |  |  |  |  |  |
|---|---|---|---|---|---|---|---|---|---|---|---|---|---|---|---|
|  |  | 260 |  |  |  | 265 |  |  |  | 270 |  |  |  |  |  |
| ctg | gag | agg | ctt | gag | ttt | ggc | agc | ctc | ctc | cac | gag | ttc | ggc | ctt | ctg | 864 |
| Leu | Glu | Arg | Leu | Glu | Phe | Gly | Ser | Leu | Leu | His | Glu | Phe | Gly | Leu | Leu |  |
|  |  | 275 |  |  |  | 280 |  |  |  | 285 |  |  |  |  |  |
| gaa | agc | ccc | aag | gcc | ctg | gag | gag | gcc | ccc | tgg | ccc | ccg | gaa | ggg | | 912 |
| Glu | Ser | Pro | Lys | Ala | Leu | Glu | Glu | Ala | Pro | Trp | Pro | Pro | Glu | Gly |  |
| 290 |  |  |  |  | 295 |  |  |  |  | 300 |  |  |  |  |  |
| gcc | ttc | gtg | ggc | ttt | gtg | ctt | tcc | cgc | aag | gag | ccc | atg | tgg | gcc | gat | 960 |
| Ala | Phe | Val | Gly | Phe | Val | Leu | Ser | Arg | Lys | Glu | Pro | Met | Trp | Ala | Asp |  |
| 305 |  |  |  |  | 310 |  |  |  |  | 315 |  |  |  |  | 320 |
| ctt | ctg | gcc | ctg | gcc | gcc | gcc | agg | ggg | ggc | cgg | gtc | cac | cgg | gcc | ccc | 1008 |
| Leu | Leu | Ala | Leu | Ala | Ala | Ala | Arg | Gly | Gly | Arg | Val | His | Arg | Ala | Pro |  |
|  |  |  |  | 325 |  |  |  |  | 330 |  |  |  |  | 335 |  |
| gag | cct | tat | aaa | gcc | ctc | agg | gac | ctg | aag | gag | gcg | cgg | ggg | ctt | ctc | 1056 |
| Glu | Pro | Tyr | Lys | Ala | Leu | Arg | Asp | Leu | Lys | Glu | Ala | Arg | Gly | Leu | Leu |  |
|  |  |  | 340 |  |  |  |  | 345 |  |  |  |  | 350 |  |  |
| gcc | aaa | gac | ctg | agc | gtt | ctg | gcc | ctg | agg | gaa | ggc | ctt | ggc | ctc | ccg | 1104 |
| Ala | Lys | Asp | Leu | Ser | Val | Leu | Ala | Leu | Arg | Glu | Gly | Leu | Gly | Leu | Pro |  |
|  |  |  |  | 355 |  |  |  |  | 360 |  |  |  |  | 365 |  |
| ccc | ggc | gac | gac | ccc | atg | ctc | ctc | gcc | tac | ctc | ctg | gac | cct | tcc | aac | 1152 |
| Pro | Gly | Asp | Asp | Pro | Met | Leu | Leu | Ala | Tyr | Leu | Leu | Asp | Pro | Ser | Asn |  |
| 370 |  |  |  |  | 375 |  |  |  |  | 380 |  |  |  |  |  |
| acc | acc | ccc | gag | ggg | gtg | gcc | cgg | cgc | tac | ggc | ggg | gag | tgg | acg | gag | 1200 |
| Thr | Thr | Pro | Glu | Gly | Val | Ala | Arg | Arg | Tyr | Gly | Gly | Glu | Trp | Thr | Glu |  |
| 385 |  |  |  |  | 390 |  |  |  |  | 395 |  |  |  |  | 400 |
| gag | gcg | ggg | gag | cgg | gcc | gcc | ctt | tcc | gag | agg | ctc | ttc | gcc | aac | ctg | 1248 |
| Glu | Ala | Gly | Glu | Arg | Ala | Ala | Leu | Ser | Glu | Arg | Leu | Phe | Ala | Asn | Leu |  |
|  |  |  |  | 405 |  |  |  |  | 410 |  |  |  |  | 415 |  |
| tgg | ggg | agg | ctt | gag | ggg | gag | gag | agg | ctc | ctt | tgg | ctt | tac | cgg | gag | 1296 |
| Trp | Gly | Arg | Leu | Glu | Gly | Glu | Glu | Arg | Leu | Leu | Trp | Leu | Tyr | Arg | Glu |  |
|  |  |  | 420 |  |  |  |  | 425 |  |  |  |  | 430 |  |  |
| gtg | gag | agg | ccc | ctt | tcc | gct | gtc | ctg | gcc | cac | atg | gag | gcc | acg | ggg | 1344 |
| Val | Glu | Arg | Pro | Leu | Ser | Ala | Val | Leu | Ala | His | Met | Glu | Ala | Thr | Gly |  |
|  |  | 435 |  |  |  |  | 440 |  |  |  |  | 445 |  |  |  |
| gtg | cgc | ctg | gac | gtg | gcc | tat | ctc | agg | gcc | ttg | tcc | ctg | gag | gtg | gcc | 1392 |
| Val | Arg | Leu | Asp | Val | Ala | Tyr | Leu | Arg | Ala | Leu | Ser | Leu | Glu | Val | Ala |  |
|  | 450 |  |  |  |  | 455 |  |  |  |  | 460 |  |  |  |  |
| gag | gag | atc | gcc | cgc | ctc | gag | gcc | gag | gtc | ttc | cgc | ctg | gcc | ggc | cac | 1440 |
| Glu | Glu | Ile | Ala | Arg | Leu | Glu | Ala | Glu | Val | Phe | Arg | Leu | Ala | Gly | His |  |
| 465 |  |  |  |  | 470 |  |  |  |  | 475 |  |  |  |  | 480 |
| ccc | ttc | aac | ctc | aac | tcc | cgg | gac | cag | ctg | gaa | agg | gtc | ctc | ttt | gac | 1488 |
| Pro | Phe | Asn | Leu | Asn | Ser | Arg | Asp | Gln | Leu | Glu | Arg | Val | Leu | Phe | Asp |  |
|  |  |  |  | 485 |  |  |  |  | 490 |  |  |  |  | 495 |  |
| gag | cta | ggg | ctt | ccc | gcc | atc | ggc | aag | acg | gag | aag | acc | ggc | aag | cgc | 1536 |
| Glu | Leu | Gly | Leu | Pro | Ala | Ile | Gly | Lys | Thr | Glu | Lys | Thr | Gly | Lys | Arg |  |
|  |  |  | 500 |  |  |  |  | 505 |  |  |  |  | 510 |  |  |
| tcc | acc | agc | gcc | gcc | gtc | ctg | gag | gcc | ctc | cgc | gag | gcc | cac | ccc | atc | 1584 |
| Ser | Thr | Ser | Ala | Ala | Val | Leu | Glu | Ala | Leu | Arg | Glu | Ala | His | Pro | Ile |  |
|  |  | 515 |  |  |  |  | 520 |  |  |  |  | 525 |  |  |  |
| gtg | gag | aag | atc | ctg | cag | tac | cgg | gag | ctc | acc | aag | ctg | aag | agc | acc | 1632 |
| Val | Glu | Lys | Ile | Leu | Gln | Tyr | Arg | Glu | Leu | Thr | Lys | Leu | Lys | Ser | Thr |  |
|  | 530 |  |  |  |  | 535 |  |  |  |  | 540 |  |  |  |  |
| tac | att | gac | ccc | ttg | ccg | gac | ctc | atc | cac | ccc | agg | acg | ggc | cgc | ctc | 1680 |
| Tyr | Ile | Asp | Pro | Leu | Pro | Asp | Leu | Ile | His | Pro | Arg | Thr | Gly | Arg | Leu |  |
| 545 |  |  |  |  | 550 |  |  |  |  | 555 |  |  |  |  | 560 |
| cac | acc | cgc | ttc | aac | cag | acg | gcc | acg | gcc | acg | ggc | agg | cta | agt | agc | 1728 |
| His | Thr | Arg | Phe | Asn | Gln | Thr | Ala | Thr | Ala | Thr | Gly | Arg | Leu | Ser | Ser |  |
|  |  |  |  | 565 |  |  |  |  | 570 |  |  |  |  | 575 |  |
| tcc | gat | ccc | aac | ctc | cag | aac | atc | ccc | gtc | cgc | acc | ccg | ctt | ggg | cag | 1776 |

```
Ser Asp Pro Asn Leu Gln Asn Ile Pro Val Arg Thr Pro Leu Gly Gln
            580                 585                 590 agg atc cgc cgg gcc ttc atc gcc gag gag ggg tgg cta ttg gtg gcc       1824
Arg Ile Arg Arg Ala Phe Ile Ala Glu Glu Gly Trp Leu Leu Val Ala
        595                 600                 605 ctg gac tat agc cag ata gag ctc agg gtg ctg gcc cac ctc tcc ggc       1872
Leu Asp Tyr Ser Gln Ile Glu Leu Arg Val Leu Ala His Leu Ser Gly
610                 615                 620 gac gag aac ctg atc cgg gtc ttc cag gag ggg cgg gac atc cac acg       1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc       1968
Glu Thr Ala Ser Trp Met Phe Gly Val Pro Arg Glu Ala Val Asp Pro
                645                 650                 655 ctg atg cgc cgg gcg gcc aag acc atc aac ttc ggg gtc ctc tac ggc       2016
Leu Met Arg Arg Ala Ala Lys Thr Ile Asn Phe Gly Val Leu Tyr Gly
            660                 665                 670 atg tcg gcc cac cgc ctc tcc cag gag cta gcc atc cct tac gag gag       2064
Met Ser Ala His Arg Leu Ser Gln Glu Leu Ala Ile Pro Tyr Glu Glu
        675                 680                 685 gcc cag gcc ttc att gag cgc tac ttt cag agc ttc ccc aag gtg cgg       2112
Ala Gln Ala Phe Ile Glu Arg Tyr Phe Gln Ser Phe Pro Lys Val Arg
690                 695                 700 gcc tgg att gag aag acc ctg gag gag ggc agg agg cgg ggg tac gtg       2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg       2208
Glu Thr Leu Phe Gly Arg Arg Arg Tyr Val Pro Asp Leu Glu Ala Arg
                725                 730                 735 ggc ccg cgc cgg gcg ccg cgt cgt ctg gtg aag agc gtg cgg gag gcg       2256
Gly Pro Arg Arg Ala Pro Arg Arg Leu Val Lys Ser Val Arg Glu Ala
            740                 745                 750 gcc gag cgc atg gcc ttc aac atg ccc gtc cag ggc acc gcc gcc gac       2304
Ala Glu Arg Met Ala Phe Asn Met Pro Val Gln Gly Thr Ala Ala Asp
        755                 760                 765 ctc atg aag ctg gct atg gtg aag ctc ttc ccc agg ctg gag gaa atg       2352
Leu Met Lys Leu Ala Met Val Lys Leu Phe Pro Arg Leu Glu Glu Met
770                 775                 780 ggg gcc agg atg ctc ctt cag gtc cac gac gag ctg gtc ctc gag gcc       2400
Gly Ala Arg Met Leu Leu Gln Val His Asp Glu Leu Val Leu Glu Ala
785                 790                 795                 800 cca aaa gag agg gcg gag gcc gtg gcc cgg ctg gcc aag gag gtc atg       2448
Pro Lys Glu Arg Ala Glu Ala Val Ala Arg Leu Ala Lys Glu Val Met
                805                 810                 815 gag ggg gtg tat ccc ctg gcc gtg ccc ctg gag gtg gag gtg ggg ata       2496
Glu Gly Val Tyr Pro Leu Ala Val Pro Leu Glu Val Glu Val Gly Ile
            820                 825                 830 ggg gag gac tgg ctc tcc gcc aag gag tga                               2526
Gly Glu Asp Trp Leu Ser Ala Lys Glu
        835                 840

<210> SEQ ID NO 14
<211> LENGTH: 841
<212> TYPE: PRT
<213> ORGANISM: Artificial Sequence
<220> FEATURE:
<223> OTHER INFORMATION: Synthetic Construct

<400> SEQUENCE: 14

Met Arg Gly Met Leu Pro Leu Phe Glu Pro Lys Gly Arg Val Leu Leu
1               5                   10                  15
```

```
Val Asp Gly His His Leu Ala Tyr Arg Thr Phe His Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
            100                 105                 110

Val Pro Gly Tyr Ala Ala Asp Val Leu Ala Ser Leu Ala Lys Lys
            115                 120                 125

Ala Glu Lys Glu Gly Tyr Glu Val Arg Ile Leu Thr Ala Ala Lys Ala
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430
```

```
Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Gly Pro Arg Arg Ala Pro Arg Arg Leu Val Lys Ser Val Arg Glu Ala
            740                 745                 750

Ala Glu Arg Met Ala Phe Asn Met Pro Val Gln Gly Thr Ala Ala Asp
        755                 760                 765

Leu Met Lys Leu Ala Met Val Lys Leu Phe Pro Arg Leu Glu Glu Met
    770                 775                 780

Gly Ala Arg Met Leu Leu Gln Val His Asp Glu Leu Val Leu Glu Ala
785                 790                 795                 800

Pro Lys Glu Arg Ala Glu Ala Val Ala Arg Leu Ala Lys Glu Val Met
                805                 810                 815

Glu Gly Val Tyr Pro Leu Ala Val Pro Leu Glu Val Glu Val Gly Ile
            820                 825                 830

Gly Glu Asp Trp Leu Ser Ala Lys Glu
            835                 840
```

-continued

```
<210> SEQ ID NO 15
<211> LENGTH: 9
<212> TYPE: PRT
<213> ORGANISM: Artificial sequence
<220> FEATURE:
<223> OTHER INFORMATION: insertion (737)

<400> SEQUENCE: 15

Gly Pro Gly Gln Ala Pro Arg Ala Leu
1               5

<210> SEQ ID NO 16
<211> LENGTH: 9
<212> TYPE: PRT
<213> ORGANISM: Artificial sequence
<220> FEATURE:
<223> OTHER INFORMATION: insertion (737)

<400> SEQUENCE: 16

Gly Pro Arg Arg Ala Pro Arg Ala Leu
1               5

<210> SEQ ID NO 17
<211> LENGTH: 19
<212> TYPE: DNA
<213> ORGANISM: Artificial Sequence
<220> FEATURE:
<223> OTHER INFORMATION: hACTB-F primer

<400> SEQUENCE: 17
tggcacccag cacaatgaa                                                   19

<210> SEQ ID NO 18
<211> LENGTH: 25
<212> TYPE: DNA
<213> ORGANISM: Artificial Sequence
<220> FEATURE:
<223> OTHER INFORMATION: hACTB-R186 primer

<400> SEQUENCE: 18
ctaagtcata gtccgcctag aagca                                            25

<210> SEQ ID NO 19
<211> LENGTH: 20
<212> TYPE: DNA
<213> ORGANISM: Artificial Sequence
<220> FEATURE:
<223> OTHER INFORMATION: hACTB-R381 primer

<400> SEQUENCE: 19
cggccacatt gtgaactttg                                                  20

<210> SEQ ID NO 20
<211> LENGTH: 20
<212> TYPE: DNA
<213> ORGANISM: Artificial Sequence
<220> FEATURE:
<223> OTHER INFORMATION: hACTB-R533 primer

<400> SEQUENCE: 20
atcacctccc ctgtgtggac                                                  20

<210> SEQ ID NO 21
<211> LENGTH: 5
<212> TYPE: PRT
<213> ORGANISM: Artificial Sequence
<220> FEATURE:
```

<223> OTHER INFORMATION: Amino acid sequnece of N-terminal of middle
      unit

<400> SEQUENCE: 21

Met Arg Gly Met Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Amino acid sequnece of N-terminal of small
      unit

<400> SEQUENCE: 22

Arg Leu Val Lys Ser
1               5

<210> SEQ ID NO 23
<211> LENGTH: 2526
<212> TYPE: DNA
<213> ORGANISM: Artificial Sequence
<220> FEATURE:
<223> OTHER INFORMATION: Taq 9aa R743X
<220> FEATURE:
<221> NAME/KEY: CDS
<222> LOCATION: (1)..(2526)
<220> FEATURE:
<221> NAME/KEY: misc_feature
<222> LOCATION: (2227)..(2229)
<223> OTHER INFORMATION: n is a, c, g, or t

<400> SEQUENCE: 23

```
atg aga gga atg tta cca tta ttc gaa ccc aag ggc cgg gtc ctc ctg      48
Met Arg Gly Met Leu Pro Leu Phe Glu Pro Lys Gly Arg Val Leu Leu
1               5                   10                  15 gtg gac ggc cac cac ctg gcc tac cgc acc ttc cac gcc ctg aag ggc      96
Val Asp Gly His His Leu Ala Tyr Arg Thr Phe His Ala Leu Lys Gly
                20                  25                  30 ctc acc acc agc cgg ggg gag ccg gtg cag gcg gtc tac ggc ttc gcc     144
Leu Thr Thr Ser Arg Gly Glu Pro Val Gln Ala Val Tyr Gly Phe Ala
            35                  40                  45 aag agc ctc ctc aag gcc ctc aag gag gac ggg gac gcg gtg atc gtg     192
Lys Ser Leu Leu Lys Ala Leu Lys Glu Asp Gly Asp Ala Val Ile Val
        50                  55                  60 gtc ttt gac gcc aag gcc ccc tcc ttc cgc cac gag gcc tac ggg ggg     240
Val Phe Asp Ala Lys Ala Pro Ser Phe Arg His Glu Ala Tyr Gly Gly
65                  70                  75                  80 tac aag gcg ggc cgg gcc ccc acg ccg gag gac ttt ccc cgg caa ctc     288
Tyr Lys Ala Gly Arg Ala Pro Thr Pro Glu Asp Phe Pro Arg Gln Leu
                85                  90                  95 gcc ctc atc aag gag ctg gtg gac ctc ctg ggg ctg gcg cgc ctc gag     336
Ala Leu Ile Lys Glu Leu Val Asp Leu Leu Gly Leu Ala Arg Leu Glu
                100                 105                 110 gtc ccg ggc tac gag gcg gac gac gtc ctg gcc agc ctg gcc aag aag     384
Val Pro Gly Tyr Glu Ala Asp Asp Val Leu Ala Ser Leu Ala Lys Lys
            115                 120                 125 gcg gaa aag gag ggc tac gag gtc cgc atc ctc acc gcc gac aaa gac     432
Ala Glu Lys Glu Gly Tyr Glu Val Arg Ile Leu Thr Ala Asp Lys Asp
        130                 135                 140 ctt tac cag ctc ctt tcc gac cgc atc cac tcc ctc cac ccc gag ggg     480
Leu Tyr Gln Leu Leu Ser Asp Arg Ile His Ser Leu His Pro Glu Gly
145                 150                 155                 160
```

-continued

| | | |
|---|---|---|
| tac ctc atc acc ccg gcc tgg ctt tgg gaa aag tac ggc ctg agg ccc<br>Tyr Leu Ile Thr Pro Ala Trp Leu Trp Glu Lys Tyr Gly Leu Arg Pro<br>165                  170                 175 | 528 |
| gac cag tgg gcc gac tac cgg gcc ctg acc ggg gac gag tcc gac aac<br>Asp Gln Trp Ala Asp Tyr Arg Ala Leu Thr Gly Asp Glu Ser Asp Asn<br>        180                 185                 190 | 576 |
| ctt ccc ggg gtc aag ggc atc ggg gag aag acg gcg agg aag ctt ctg<br>Leu Pro Gly Val Lys Gly Ile Gly Glu Lys Thr Ala Arg Lys Leu Leu<br>            195                 200                 205 | 624 |
| gag gag tgg ggg agc ctg gaa gcc ctc ctc aag aac ctg gac cgg ctg<br>Glu Glu Trp Gly Ser Leu Glu Ala Leu Leu Lys Asn Leu Asp Arg Leu<br>210                 215                 220 | 672 |
| aag ccc gcc atc cgg gag aag atc ctg gcc cac atg gac gat ctg aag<br>Lys Pro Ala Ile Arg Glu Lys Ile Leu Ala His Met Asp Asp Leu Lys<br>225                 230                 235                 240 | 720 |
| ctc tcc tgg gac ctg gcc aag gtg cgc acc gac ctg ccc ctg gag gtg<br>Leu Ser Trp Asp Leu Ala Lys Val Arg Thr Asp Leu Pro Leu Glu Val<br>                245                 250                 255 | 768 |
| gac ttc gcc aaa agg cgg gag ccc gac cgg gag agg ctt agg gcc ttt<br>Asp Phe Ala Lys Arg Arg Glu Pro Asp Arg Glu Arg Leu Arg Ala Phe<br>                260                 265                 270 | 816 |
| ctg gag agg ctt gag ttt ggc agc ctc ctc cac gag ttc ggc ctt ctg<br>Leu Glu Arg Leu Glu Phe Gly Ser Leu Leu His Glu Phe Gly Leu Leu<br>            275                 280                 285 | 864 |
| gaa agc ccc aag gcc ctg gag gag gcc ccc tgg ccc ccg ccg gaa ggg<br>Glu Ser Pro Lys Ala Leu Glu Glu Ala Pro Trp Pro Pro Pro Glu Gly<br>290                 295                 300 | 912 |
| gcc ttc gtg ggc ttt gtg ctt tcc cgc aag gag ccc atg tgg gcc gat<br>Ala Phe Val Gly Phe Val Leu Ser Arg Lys Glu Pro Met Trp Ala Asp<br>305                 310                 315                 320 | 960 |
| ctt ctg gcc ctg gcc gcc gcc agg ggg ggc cgg gtc cac cgg gcc ccc<br>Leu Leu Ala Leu Ala Ala Ala Arg Gly Gly Arg Val His Arg Ala Pro<br>                325                 330                 335 | 1008 |
| gag cct tat aaa gcc ctc agg gac ctg aag gag gcg cgg ggg ctt ctc<br>Glu Pro Tyr Lys Ala Leu Arg Asp Leu Lys Glu Ala Arg Gly Leu Leu<br>                340                 345                 350 | 1056 |
| gcc aaa gac ctg agc gtt ctg gcc ctg agg gaa ggc ctt ggc ctc ccg<br>Ala Lys Asp Leu Ser Val Leu Ala Leu Arg Glu Gly Leu Gly Leu Pro<br>            355                 360                 365 | 1104 |
| ccc ggc gac gac ccc atg ctc ctc gcc tac ctc ctg gac cct tcc aac<br>Pro Gly Asp Asp Pro Met Leu Leu Ala Tyr Leu Leu Asp Pro Ser Asn<br>370                 375                 380 | 1152 |
| acc acc ccc gag ggg gtg gcc cgg cgc tac ggc ggg gag tgg acg gag<br>Thr Thr Pro Glu Gly Val Ala Arg Arg Tyr Gly Gly Glu Trp Thr Glu<br>385                 390                 395                 400 | 1200 |
| gag gcg ggg gag cgg gcc gcc ctt tcc gag agg ctc ttc gcc aac ctg<br>Glu Ala Gly Glu Arg Ala Ala Leu Ser Glu Arg Leu Phe Ala Asn Leu<br>                405                 410                 415 | 1248 |
| tgg ggg agg ctt gag ggg gag gag agg ctc ctt tgg ctt tac cgg gag<br>Trp Gly Arg Leu Glu Gly Glu Glu Arg Leu Leu Trp Leu Tyr Arg Glu<br>            420                 425                 430 | 1296 |
| gtg gag agg ccc ctt tcc gct gtc ctg gcc cac atg gag gcc acg ggg<br>Val Glu Arg Pro Leu Ser Ala Val Leu Ala His Met Glu Ala Thr Gly<br>                435                 440                 445 | 1344 |
| gtg cgc ctg gac gtg gcc tat ctc agg gcc ttg tcc ctg gag gtg gcc<br>Val Arg Leu Asp Val Ala Tyr Leu Arg Ala Leu Ser Leu Glu Val Ala<br>            450                 455                 460 | 1392 |
| gag gag atc gcc cgc ctc gag gcc gag gtc ttc cgc ctg gcc ggc cac<br>Glu Glu Ile Ala Arg Leu Glu Ala Glu Val Phe Arg Leu Ala Gly His<br>465                 470                 475                 480 | 1440 |

```
ccc ttc aac ctc aac tcc cgg gac cag ctg gaa agg gtc ctc ttt gac    1488
Pro Phe Asn Leu Asn Ser Arg Asp Gln Leu Glu Arg Val Leu Phe Asp
                485                 490                 495 gag cta ggg ctt ccc gcc atc ggc aag acg gag aag acc ggc aag cgc    1536
Glu Leu Gly Leu Pro Ala Ile Gly Lys Thr Glu Lys Thr Gly Lys Arg
        500                 505                 510 tcc acc agc gcc gcc gtc ctg gag gcc ctc cgc gag gcc cac ccc atc    1584
Ser Thr Ser Ala Ala Val Leu Glu Ala Leu Arg Glu Ala His Pro Ile
            515                 520                 525 gtg gag aag atc ctg cag tac cgg gag ctc acc aag ctg aag agc acc    1632
Val Glu Lys Ile Leu Gln Tyr Arg Glu Leu Thr Lys Leu Lys Ser Thr
        530                 535                 540 tac att gac ccc ttg ccg gac ctc atc cac ccc agg acg ggc cgc ctc    1680
Tyr Ile Asp Pro Leu Pro Asp Leu Ile His Pro Arg Thr Gly Arg Leu
545                 550                 555                 560 cac acc cgc ttc aac cag acg gcc acg gcc acg ggc agg cta agt agc    1728
His Thr Arg Phe Asn Gln Thr Ala Thr Ala Thr Gly Arg Leu Ser Ser
                565                 570                 575 tcc gat ccc aac ctc cag aac atc ccc gtc cgc acc ccg ctt ggg cag    1776
Ser Asp Pro Asn Leu Gln Asn Ile Pro Val Arg Thr Pro Leu Gly Gln
        580                 585                 590 agg atc cgc cgg gcc ttc atc gcc gag gag ggg tgg cta ttg gtg gcc    1824
Arg Ile Arg Arg Ala Phe Ile Ala Glu Glu Gly Trp Leu Leu Val Ala
            595                 600                 605 ctg gac tat agc cag ata gag ctc agg gtg ctg gcc cac ctc tcc ggc    1872
Leu Asp Tyr Ser Gln Ile Glu Leu Arg Val Leu Ala His Leu Ser Gly
        610                 615                 620 gac gag aac ctg atc cgg gtc ttc cag gag ggg cgg gac atc cac acg    1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc    1968
Glu Thr Ala Ser Trp Met Phe Gly Val Pro Arg Glu Ala Val Asp Pro
                645                 650                 655 ctg atg cgc cgg gcg gcc aag acc atc aac ttc ggg gtc ctc tac ggc    2016
Leu Met Arg Arg Ala Ala Lys Thr Ile Asn Phe Gly Val Leu Tyr Gly
        660                 665                 670 atg tcg gcc cac cgc ctc tcc cag gag cta gcc atc cct tac gag gag    2064
Met Ser Ala His Arg Leu Ser Gln Glu Leu Ala Ile Pro Tyr Glu Glu
            675                 680                 685 gcc cag gcc ttc att gag cgc tac ttt cag agc ttc ccc aag gtg cgg    2112
Ala Gln Ala Phe Ile Glu Arg Tyr Phe Gln Ser Phe Pro Lys Val Arg
        690                 695                 700 gcc tgg att gag aag acc ctg gag gag ggc agg agg cgg ggg tac gtg    2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg    2208
Glu Thr Leu Phe Gly Arg Arg Arg Tyr Val Pro Asp Leu Glu Ala Arg
                725                 730                 735 ggc ccg cgc cgg gcg ccg nnn cgt ctg gtg aag agc gtg cgg gag gcg    2256
Gly Pro Arg Arg Ala Pro Xaa Arg Leu Val Lys Ser Val Arg Glu Ala
        740                 745                 750 gcc gag cgc atg gcc ttc aac atg ccc gtc cag ggc acc gcc gcc gac    2304
Ala Glu Arg Met Ala Phe Asn Met Pro Val Gln Gly Thr Ala Ala Asp
            755                 760                 765 ctc atg aag ctg gct atg gtg aag ctc ttc ccc agg ctg gag gaa atg    2352
Leu Met Lys Leu Ala Met Val Lys Leu Phe Pro Arg Leu Glu Glu Met
        770                 775                 780 ggg gcc agg atg ctc ctt cag gtc cac gac gag ctg gtc ctc gag gcc    2400
Gly Ala Arg Met Leu Leu Gln Val His Asp Glu Leu Val Leu Glu Ala
```

```
                785                 790                 795                 800
cca aaa gag agg gcg gag gcc gtg gcc cgg ctg gcc aag gag gtc atg          2448
Pro Lys Glu Arg Ala Glu Ala Val Ala Arg Leu Ala Lys Glu Val Met
            805                 810                 815 gag ggg gtg tat ccc ctg gcc gtg ccc ctg gag gtg gag gtg ggg ata          2496
Glu Gly Val Tyr Pro Leu Ala Val Pro Leu Glu Val Glu Val Gly Ile
        820                 825                 830 ggg gag gac tgg ctc tcc gcc aag gag tga                                  2526
Gly Glu Asp Trp Leu Ser Ala Lys Glu
        835                 840

<210> SEQ ID NO 24
<211> LENGTH: 841
<212> TYPE: PRT
<213> ORGANISM: Artificial Sequence
<220> FEATURE:
<221> NAME/KEY: misc_feature
<222> LOCATION: (743)..(743)
<223> OTHER INFORMATION: The 'Xaa' at location 743 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 24

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Ser Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
```

-continued

```
              260                 265                 270
Leu Glu Arg Leu Glu Phe Gly Ser Leu Leu His Glu Phe Gly Leu Leu
            275                 280                 285
Glu Ser Pro Lys Ala Leu Glu Ala Pro Trp Pro Pro Glu Gly
        290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
        370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
        530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
```

```
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Gly Tyr Val
705                 710                 715                 720
Glu Thr Leu Phe Gly Arg Arg Tyr Val Pro Asp Leu Glu Ala Arg
                725                 730                 735
Gly Pro Arg Arg Ala Pro Xaa Arg Leu Val Lys Ser Val Arg Glu Ala
                740                 745                 750
Ala Glu Arg Met Ala Phe Asn Met Pro Val Gln Gly Thr Ala Ala Asp
            755                 760                 765
Leu Met Lys Leu Ala Met Val Lys Leu Phe Pro Arg Leu Glu Glu Met
    770                 775                 780
Gly Ala Arg Met Leu Leu Gln Val His Asp Glu Leu Val Leu Glu Ala
785                 790                 795                 800
Pro Lys Glu Arg Ala Glu Ala Val Ala Arg Leu Ala Lys Glu Val Met
                805                 810                 815
Glu Gly Val Tyr Pro Leu Ala Val Pro Leu Glu Val Glu Val Gly Ile
            820                 825                 830
Gly Glu Asp Trp Leu Ser Ala Lys Glu
            835                 840
```

<210> SEQ ID NO 25
<211> LENGTH: 2526
<212> TYPE: DNA
<213> ORGANISM: Artificial Sequence
<220> FEATURE:
<223> OTHER INFORMATION: Taq Exo- + 9aa R743X
<220> FEATURE:
<221> NAME/KEY: CDS
<222> LOCATION: (1)..(2526)
<220> FEATURE:
<221> NAME/KEY: misc_feature
<222> LOCATION: (2227)..(2229)
<223> OTHER INFORMATION: n is a, c, g, or t

<400> SEQUENCE: 25

```
atg agg ggg atg ctg ccc ctc ttt gag ccc aag ggc cgg gtc ctc ctg      48
Met Arg Gly Met Leu Pro Leu Phe Glu Pro Lys Gly Arg Val Leu Leu
1               5                   10                  15 gtg gac ggc cac cac ctg gcc tac cgc acc ttc cac gcc ctg aag ggc      96
Val Asp Gly His His Leu Ala Tyr Arg Thr Phe His Ala Leu Lys Gly
                20                  25                  30 ctc acc acc agc cgg ggg gag ccg gtg cag gcg gtc tac ggc ttc gcc     144
Leu Thr Thr Ser Arg Gly Glu Pro Val Gln Ala Val Tyr Gly Phe Ala
            35                  40                  45 aag agc ctc ctc aag gcc ctc aag gag gac ggg gac gcg gtg atc gtg     192
Lys Ser Leu Leu Lys Ala Leu Lys Glu Asp Gly Asp Ala Val Ile Val
        50                  55                  60 gtc ttt gac gcc aag gcc ccc tcc ttc cgc cac gag gcc tac ggg ggg     240
Val Phe Asp Ala Lys Ala Pro Ser Phe Arg His Glu Ala Tyr Gly Gly
65                  70                  75                  80 tac aag gcg ggc cgg gcc ccc acg ccg gag gac ttt ccc cgg caa ctc     288
Tyr Lys Ala Gly Arg Ala Pro Thr Pro Glu Asp Phe Pro Arg Gln Leu
                85                  90                  95 gcc ctc atc aag gag ctg gtg gac ctc ctg ggg ctg gcg cgc ctc gag     336
Ala Leu Ile Lys Glu Leu Val Asp Leu Leu Gly Leu Ala Arg Leu Glu
                100                 105                 110 gtc ccg ggc tac gcg gcg gcc gac gtc ctg gcc agc ctg gcc aag aag     384
Val Pro Gly Tyr Ala Ala Ala Asp Val Leu Ala Ser Leu Ala Lys Lys
            115                 120                 125
```

| | | | | | | | | | | | | | | | | |
|---|---|---|---|---|---|---|---|---|---|---|---|---|---|---|---|---|
| gcg | gaa | aag | gag | ggc | tac | gag | gtc | cgc | atc | ctc | acc | gcc | gcc | aaa | gcc | 432 |
| Ala | Glu | Lys | Glu | Gly | Tyr | Glu | Val | Arg | Ile | Leu | Thr | Ala | Ala | Lys | Ala | |
| | 130 | | | | 135 | | | | 140 | | | | | | | |
| ctt | tac | cag | ctc | ctt | tcc | gac | cgc | atc | cac | gtc | ctc | cac | ccc | gag | ggg | 480 |
| Leu | Tyr | Gln | Leu | Leu | Ser | Asp | Arg | Ile | His | Val | Leu | His | Pro | Glu | Gly | |
| 145 | | | | | 150 | | | | | 155 | | | | | 160 | |
| tac | ctc | atc | acc | ccg | gcc | tgg | ctt | tgg | gaa | aag | tac | ggc | ctg | agg | ccc | 528 |
| Tyr | Leu | Ile | Thr | Pro | Ala | Trp | Leu | Trp | Glu | Lys | Tyr | Gly | Leu | Arg | Pro | |
| | | | | 165 | | | | | 170 | | | | | 175 | | |
| gac | cag | tgg | gcc | gac | tac | cgg | gcc | ctg | acc | ggg | gac | gag | tcc | gac | aac | 576 |
| Asp | Gln | Trp | Ala | Asp | Tyr | Arg | Ala | Leu | Thr | Gly | Asp | Glu | Ser | Asp | Asn | |
| | | 180 | | | | | 185 | | | | | 190 | | | | |
| ctt | ccc | ggg | gtc | aag | ggc | atc | ggg | gag | aag | acg | gcg | agg | aag | ctt | ctg | 624 |
| Leu | Pro | Gly | Val | Lys | Gly | Ile | Gly | Glu | Lys | Thr | Ala | Arg | Lys | Leu | Leu | |
| | | 195 | | | | | 200 | | | | | 205 | | | | |
| gag | gag | tgg | ggg | agc | ctg | gaa | gcc | ctc | ctc | aag | aac | ctg | gac | cgg | ctg | 672 |
| Glu | Glu | Trp | Gly | Ser | Leu | Glu | Ala | Leu | Leu | Lys | Asn | Leu | Asp | Arg | Leu | |
| | 210 | | | | 215 | | | | 220 | | | | | | | |
| aag | ccc | gcc | atc | cgg | gag | aag | atc | ctg | gcc | cac | atg | gac | gat | ctg | aag | 720 |
| Lys | Pro | Ala | Ile | Arg | Glu | Lys | Ile | Leu | Ala | His | Met | Asp | Asp | Leu | Lys | |
| 225 | | | | | 230 | | | | | 235 | | | | | 240 | |
| ctc | tcc | tgg | gac | ctg | gcc | aag | gtg | cgc | acc | gac | ctg | ccc | ctg | gag | gtg | 768 |
| Leu | Ser | Trp | Asp | Leu | Ala | Lys | Val | Arg | Thr | Asp | Leu | Pro | Leu | Glu | Val | |
| | | | | 245 | | | | | 250 | | | | | 255 | | |
| gac | ttc | gcc | aaa | agg | cgg | gag | ccc | gac | cgg | gag | agg | ctt | agg | gcc | ttt | 816 |
| Asp | Phe | Ala | Lys | Arg | Arg | Glu | Pro | Asp | Arg | Glu | Arg | Leu | Arg | Ala | Phe | |
| | | | 260 | | | | | 265 | | | | | 270 | | | |
| ctg | gag | agg | ctt | gag | ttt | ggc | agc | ctc | ctc | cac | gag | ttc | ggc | ctt | ctg | 864 |
| Leu | Glu | Arg | Leu | Glu | Phe | Gly | Ser | Leu | Leu | His | Glu | Phe | Gly | Leu | Leu | |
| | 275 | | | | | 280 | | | | | 285 | | | | | |
| gaa | agc | ccc | aag | gcc | ctg | gag | gag | gcc | ccc | tgg | ccc | ccg | ccg | gaa | ggg | 912 |
| Glu | Ser | Pro | Lys | Ala | Leu | Glu | Glu | Ala | Pro | Trp | Pro | Pro | Pro | Glu | Gly | |
| | | 290 | | | | | 295 | | | | | 300 | | | | |
| gcc | ttc | gtg | ggc | ttt | gtg | ctt | tcc | cgc | aag | gag | ccc | atg | tgg | gcc | gat | 960 |
| Ala | Phe | Val | Gly | Phe | Val | Leu | Ser | Arg | Lys | Glu | Pro | Met | Trp | Ala | Asp | |
| 305 | | | | | 310 | | | | | 315 | | | | | 320 | |
| ctt | ctg | gcc | ctg | gcc | gcc | gcc | agg | ggg | ggc | cgg | gtc | cac | cgg | gcc | ccc | 1008 |
| Leu | Leu | Ala | Leu | Ala | Ala | Ala | Arg | Gly | Gly | Arg | Val | His | Arg | Ala | Pro | |
| | | | | 325 | | | | | 330 | | | | | 335 | | |
| gag | cct | tat | aaa | gcc | ctc | agg | gac | ctg | aag | gag | gcg | cgg | ggg | ctt | ctc | 1056 |
| Glu | Pro | Tyr | Lys | Ala | Leu | Arg | Asp | Leu | Lys | Glu | Ala | Arg | Gly | Leu | Leu | |
| | | | 340 | | | | | 345 | | | | | 350 | | | |
| gcc | aaa | gac | ctg | agc | gtt | ctg | gcc | ctg | agg | gaa | ggc | ctt | ggc | ctc | ccg | 1104 |
| Ala | Lys | Asp | Leu | Ser | Val | Leu | Ala | Leu | Arg | Glu | Gly | Leu | Gly | Leu | Pro | |
| | | 355 | | | | | 360 | | | | | 365 | | | | |
| ccc | ggc | gac | gac | ccc | atg | ctc | ctc | gcc | tac | ctc | ctg | gac | cct | tcc | aac | 1152 |
| Pro | Gly | Asp | Asp | Pro | Met | Leu | Leu | Ala | Tyr | Leu | Leu | Asp | Pro | Ser | Asn | |
| | 370 | | | | | 375 | | | | | 380 | | | | | |
| acc | acc | ccc | gag | ggg | gtg | gcc | cgg | cgc | tac | ggc | ggg | gag | tgg | acg | gag | 1200 |
| Thr | Thr | Pro | Glu | Gly | Val | Ala | Arg | Arg | Tyr | Gly | Gly | Glu | Trp | Thr | Glu | |
| 385 | | | | | 390 | | | | | 395 | | | | | 400 | |
| gag | gcg | ggg | gag | cgg | gcc | gcc | ctt | tcc | gag | agg | ctc | ttc | gcc | aac | ctg | 1248 |
| Glu | Ala | Gly | Glu | Arg | Ala | Ala | Leu | Ser | Glu | Arg | Leu | Phe | Ala | Asn | Leu | |
| | | | | 405 | | | | | 410 | | | | | 415 | | |
| tgg | ggg | agg | ctt | gag | ggg | gag | gag | agg | ctc | ctt | tgg | ctt | tac | cgg | gag | 1296 |
| Trp | Gly | Arg | Leu | Glu | Gly | Glu | Glu | Arg | Leu | Leu | Trp | Leu | Tyr | Arg | Glu | |
| | | | 420 | | | | | 425 | | | | | 430 | | | |
| gtg | gag | agg | ccc | ctt | tcc | gct | gtc | ctg | gcc | cac | atg | gag | gcc | acg | ggg | 1344 |
| Val | Glu | Arg | Pro | Leu | Ser | Ala | Val | Leu | Ala | His | Met | Glu | Ala | Thr | Gly | |

```
              435                 440                 445
gtg cgc ctg gac gtg gcc tat ctc agg gcc ttg tcc ctg gag gtg gcc    1392
Val Arg Leu Asp Val Ala Tyr Leu Arg Ala Leu Ser Leu Glu Val Ala
    450                 455                 460 gag gag atc gcc cgc ctc gag gcc gag gtc ttc cgc ctg gcc ggc cac    1440
Glu Glu Ile Ala Arg Leu Glu Ala Glu Val Phe Arg Leu Ala Gly His
465                 470                 475                 480 ccc ttc aac ctc aac tcc cgg gac cag ctg gaa agg gtc ctc ttt gac    1488
Pro Phe Asn Leu Asn Ser Arg Asp Gln Leu Glu Arg Val Leu Phe Asp
                485                 490                 495 gag cta ggg ctt ccc gcc atc ggc aag acg gag aag acc ggc aag cgc    1536
Glu Leu Gly Leu Pro Ala Ile Gly Lys Thr Glu Lys Thr Gly Lys Arg
            500                 505                 510 tcc acc agc gcc gcc gtc ctg gag gcc ctc cgc gag gcc cac ccc atc    1584
Ser Thr Ser Ala Ala Val Leu Glu Ala Leu Arg Glu Ala His Pro Ile
        515                 520                 525 gtg gag aag atc ctg cag tac cgg gag ctc acc aag ctg aag agc acc    1632
Val Glu Lys Ile Leu Gln Tyr Arg Glu Leu Thr Lys Leu Lys Ser Thr
    530                 535                 540 tac att gac ccc ttg ccg gac ctc atc cac ccc agg acg ggc cgc ctc    1680
Tyr Ile Asp Pro Leu Pro Asp Leu Ile His Pro Arg Thr Gly Arg Leu
545                 550                 555                 560 cac acc cgc ttc aac cag acg gcc acg gcc acg ggc agg cta agt agc    1728
His Thr Arg Phe Asn Gln Thr Ala Thr Ala Thr Gly Arg Leu Ser Ser
                565                 570                 575 tcc gat ccc aac ctc cag aac atc ccc gtc cgc acc ccg ctt ggg cag    1776
Ser Asp Pro Asn Leu Gln Asn Ile Pro Val Arg Thr Pro Leu Gly Gln
            580                 585                 590 agg atc cgc cgg gcc ttc atc gcc gag gag ggg tgg cta ttg gtg gcc    1824
Arg Ile Arg Arg Ala Phe Ile Ala Glu Glu Gly Trp Leu Leu Val Ala
        595                 600                 605 ctg gac tat agc cag ata gag ctc agg gtg ctg gcc cac ctc tcc ggc    1872
Leu Asp Tyr Ser Gln Ile Glu Leu Arg Val Leu Ala His Leu Ser Gly
    610                 615                 620 gac gag aac ctg atc cgg gtc ttc cag gag ggg cgg gac atc cac acg    1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc    1968
Glu Thr Ala Ser Trp Met Phe Gly Val Pro Arg Glu Ala Val Asp Pro
                645                 650                 655 ctg atg cgc cgg gcg gcc aag acc atc aac ttc ggg gtc ctc tac ggc    2016
Leu Met Arg Arg Ala Ala Lys Thr Ile Asn Phe Gly Val Leu Tyr Gly
            660                 665                 670 atg tcg gcc cac cgc ctc tcc cag gag cta gcc atc cct tac gag gag    2064
Met Ser Ala His Arg Leu Ser Gln Glu Leu Ala Ile Pro Tyr Glu Glu
        675                 680                 685 gcc cag gcc ttc att gag cgc tac ttt cag agc ttc ccc aag gtg cgg    2112
Ala Gln Ala Phe Ile Glu Arg Tyr Phe Gln Ser Phe Pro Lys Val Arg
    690                 695                 700 gcc tgg att gag aag acc ctg gag gag ggc agg agg cgg ggg tac gtg    2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg    2208
Glu Thr Leu Phe Gly Arg Arg Arg Tyr Val Pro Asp Leu Glu Ala Arg
                725                 730                 735 ggc ccg cgc cgg gcg ccg nnn cgt ctg gtg aag agc gtg cgg gag gcg    2256
Gly Pro Arg Arg Ala Pro Xaa Arg Leu Val Lys Ser Val Arg Glu Ala
            740                 745                 750 gcc gag cgc atg gcc ttc aac atg ccc gtc cag ggc acc gcc gcc gac    2304
```

```
                Ala Glu Arg Met Ala Phe Asn Met Pro Val Gln Gly Thr Ala Ala Asp
                        755                 760                 765 ctc atg aag ctg gct atg gtg aag ctc ttc ccc agg ctg gag gaa atg            2352
Leu Met Lys Leu Ala Met Val Lys Leu Phe Pro Arg Leu Glu Glu Met
        770                 775                 780 ggg gcc agg atg ctc ctt cag gtc cac gac gag ctg gtc ctc gag gcc            2400
Gly Ala Arg Met Leu Leu Gln Val His Asp Glu Leu Val Leu Glu Ala
785                 790                 795                 800 cca aaa gag agg gcg gag gcc gtg gcc cgg ctg gcc aag gag gtc atg            2448
Pro Lys Glu Arg Ala Glu Ala Val Ala Arg Leu Ala Lys Glu Val Met
                805                 810                 815 gag ggg gtg tat ccc ctg gcc gtg ccc ctg gag gtg gag gtg ggg ata            2496
Glu Gly Val Tyr Pro Leu Ala Val Pro Leu Glu Val Glu Val Gly Ile
        820                 825                 830 ggg gag gac tgg ctc tcc gcc aag gag tga                                    2526
Gly Glu Asp Trp Leu Ser Ala Lys Glu
        835                 840
```

<210> SEQ ID NO 26
<211> LENGTH: 841
<212> TYPE: PRT
<213> ORGANISM: Artificial Sequence
<220> FEATURE:
<221> NAME/KEY: misc_feature
<222> LOCATION: (743)..(743)
<223> OTHER INFORMATION: The 'Xaa' at location 743 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 26

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Ala Ala Asp Val Leu Ala Ser Leu Ala Lys Lys
        115                 120                 125

Ala Glu Lys Glu Gly Tyr Glu Val Arg Ile Leu Thr Ala Ala Lys Ala
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
```

```
                210                 215                 220
Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640
```

```
Glu Thr Ala Ser Trp Met Phe Gly Val Pro Arg Glu Ala Val Asp Pro
              645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Gly Pro Arg Arg Ala Pro Xaa Arg Leu Val Lys Ser Val Arg Glu Ala
            740                 745                 750

Ala Glu Arg Met Ala Phe Asn Met Pro Val Gln Gly Thr Ala Ala Asp
        755                 760                 765

Leu Met Lys Leu Ala Met Val Lys Leu Phe Pro Arg Leu Glu Glu Met
    770                 775                 780

Gly Ala Arg Met Leu Leu Gln Val His Asp Glu Leu Val Leu Glu Ala
785                 790                 795                 800

Pro Lys Glu Arg Ala Glu Ala Val Ala Arg Leu Ala Lys Glu Val Met
            805                 810                 815

Glu Gly Val Tyr Pro Leu Ala Val Pro Leu Glu Val Glu Val Gly Ile
                820                 825                 830

Gly Glu Asp Trp Leu Ser Ala Lys Glu
            835                 840
```